(12) United States Patent
Wehner et al.

(10) Patent No.: US 6,620,820 B2
(45) Date of Patent: Sep. 16, 2003

(54) INHIBITORS OF BONE REABSORPTION AND ANTAGONISTS OF VITRONECTIN RECEPTORS

(75) Inventors: Volkmar Wehner, Sandberg (DE); Jochen Knolle, Kriftel (DE); Hans Ulrich Stilz, Frankfurt (DE); Denis Carniato, Marcoussis (FR); Jean-Francois Gourvest, Claye Souilly (FR); Tom Gadek, Oakland, CA (US); Robert McDowell, San Francisco, CA (US)

(73) Assignees: Hoechst Aktiengesellschaft, Frankfurt am Main (DE); Genentech, Inc., S. San Francisco, CA (US)

( * ) Notice: Subject to any disclaimer, the term of this patent is extended or adjusted under 35 U.S.C. 154(b) by 0 days.

(21) Appl. No.: 10/078,398

(22) Filed: Feb. 21, 2002

(65) Prior Publication Data

US 2002/0119999 A1 Aug. 29, 2002

Related U.S. Application Data

(63) Continuation of application No. 09/798,955, filed on Mar. 6, 2001, now abandoned, which is a continuation of application No. 08/821,253, filed on Mar. 20, 1997, now Pat. No. 6,218,415.

(30) Foreign Application Priority Data

| Mar. 20, 1996 | (DE) | 196 10 919 |
| Jul. 3, 1996 | (DE) | 196 26 701 |
| Sep. 2, 1996 | (DE) | 196 35 522 |

(51) Int. Cl.[7] ................... A61K 31/4747; C07D 471/10
(52) U.S. Cl. ........................... 514/278; 546/16; 546/20
(58) Field of Search ................ 546/16, 20; 514/278; 544/332; 548/306.1

(56) References Cited

U.S. PATENT DOCUMENTS

| 4,344,949 | A | 8/1982 | Hoefle et al. |
| 4,350,704 | A | 9/1982 | Hoefle et al. |
| 4,374,847 | A | 2/1983 | Gruenfeld |
| 5,389,614 | A | 2/1995 | König et al. |
| 5,397,796 | A | 3/1995 | Zoller et al. |
| 5,424,293 | A | 6/1995 | Zoller et al. |
| 5,554,594 | A | 9/1996 | Zoller et al. |
| 5,658,935 | A | 8/1997 | Klingler et al. |
| 6,218,415 | B1 | 4/2001 | Wehner et al. |
| 6,294,556 | B1 * | 9/2001 | Schnorrenberg et al. .... 514/331 |

FOREIGN PATENT DOCUMENTS

| DE | 43 01 747 | 7/1994 |
| EP | 0 029 488 | 6/1981 |
| EP | 0 031 741 | 7/1981 |
| EP | 0 046 953 | 3/1982 |
| EP | 0 049 605 | 4/1982 |
| EP | 0 049 658 | 4/1982 |
| EP | 0 050 800 | 5/1982 |
| EP | 0 051 020 | 5/1982 |
| EP | 0 052 870 | 6/1982 |
| EP | 0 079 022 | 5/1983 |
| EP | 0 084 164 | 7/1983 |
| EP | 0 089 637 | 9/1983 |
| EP | 0 090 341 | 10/1983 |
| EP | 0 090 362 | 10/1983 |
| EP | 0 105 102 | 4/1984 |
| EP | 0 109 020 | 5/1984 |
| EP | 0 111 873 | 6/1984 |
| EP | 0 271 865 | 6/1988 |
| EP | 0 344 682 | 12/1989 |
| EP | 0 449 079 | 10/1991 |
| EP | 0 528 586 | 2/1993 |
| EP | 0 528 587 | 2/1993 |
| EP | 0 530 505 | 3/1993 |
| EP | 0 566 919 | 10/1993 |
| EP | 0 584 694 | 3/1994 |
| WO | 93/18057 | 9/1993 |
| WO | 94/08577 | 4/1994 |
| WO | 94/12181 | 6/1994 |
| WO | 95/14008 | 5/1995 |
| WO | 95/28426 | 10/1995 |
| WO | 95/32710 | 12/1995 |
| WO | 96/00574 | 1/1996 |
| WO | 96/00730 | 1/1996 |

OTHER PUBLICATIONS

English language abstract of EP 46953 (Mar. 10, 1982), Derwent Publications Ltd., p. 20124.
Alves, et al., *Eur. J. Med. Chem—Chim. Ther.* 21:297–304 (1986) (with English–language summary).
Birtwell, et al., *J. Chem. Soc.* pp. 491–494 (1946).
Brooks, et al., *Cell* 79:1157–1164 (1994).
Büllesbach, *Kontakte* 1:23–25 (1980).
Dennis, et al., *Proc. Natl. Acad. Sci. USA* 87:2471–2475 (1989).
Dennis, et al., *Proteins: Structure, Function and Genetics* 15:312–321 (1993).

(List continued on next page.)

*Primary Examiner*—Joseph K. McKane
*Assistant Examiner*—Ebenezer Sackey
(74) *Attorney, Agent, or Firm*—Foley & Lardner

(57) ABSTRACT

The present invention relates to 5-membered ring heterocycles of the formula I, $$\underset{Z\text{---}Y}{\overset{W}{\underset{|}{\text{---}}}}\overset{\overset{O}{\overset{\|}{C}}}{\underset{|}{\text{---}}}\overset{N}{\underset{|}{\text{---}}}\text{E---F---G} \quad (I)$$

in which E, F, G, W, Y and Z have the meaning given in the patent claims, to their preparation and to their use as medicaments.

The novel compounds are used as vitronectin receptor antagonists and as inhibitors of bone reabsorption.

3 Claims, No Drawings

OTHER PUBLICATIONS

Desideri, et al., *Arch Pharm.* 325:773–777 (1992).
Fisher, et al., *Endocrinology* 132:1411–1413 (1993).
Goldschmidt, et al., *Liebigs Ann. Chem.* 575:217–231 (1952).
English language abstract of Goldschmidt et al., Ann. 575:217–31 (1952), *Chemical Abstracts*, vol. 47, Col. 3795.
Garratt, et al., *Tetrahedron* 49:165–176 (1993).
Horton, et al., *Exp. Cell. Res.* 195:368–375 (1991).
Hubbuch, *Kontakte* 3:14–23 (1979).
Jung, et al., *J. Med. Chem.* 34:1110–1116 (1991).
Kobiro, et al., *Tetrahedron Lett.* 28(33):3825–3826 (1987).
Lettre, et al., *Berichte* 84:719–729 (1951).
English language abstract of Lettre et al., Chem. Ber. 84:719–29 (1951), *Organic Chemistry Abstracts*, vol. 10, Col. 3045.
March, *Advanced Organic Chemistry*, Third Ed., J. Wiley & Sons, pp. 350–351 (1985).
McKay, et al., *J. Am. Chem. Soc.* 71:766–770 (1949).
McKay, et al., *J. Med. Chem.* 6:587–595 (1963).
Purkayastha, et al., *Indian J. Chem.* 30B:646–650 (1991).
Sato, et al., *J. Cell Biol.* 111:1713–1723 (1990).
Sorba, et al., *Eur. J. Med. Chem.* 21:391–395 (1986).
Staab, *Angew. Chemie. Int. Ed.* 1:351–367 (1962).
Takahata, et al., *Synthesis* pp. 703–708 (1984).
Webb, et al., *J. Heterocyclic Chem.* 24:275–278 (1987).
Weiss, et al., *Chemiker Zeitung* 98:617–618 (1974).
English language abstract of Weiss et al., Chem.–Ztg. 98:617–18 (1974), *Chemical Abstracts*, Abstract No. 82:111547.
Wulfman, et al., *Synthesis* pp. 924–925 (1978).

* cited by examiner

INHIBITORS OF BONE REABSORPTION AND ANTAGONISTS OF VITRONECTIN RECEPTORS

This application is a continuation of application of U.S. application Ser. No. 09/798,955, filed on Mar. 6, 2001, now abandoned, which in turn is a continuation of U.S. application No. 08/821,253, filed on Mar. 20, 1997, now U.S. Pat. No. 6,218,415. The entirety of the applications is hereby incorporated by reference.

BACKGROUND OF THE INVENTION

Human bones are subject to a continuous dynamic process of reconstruction which involves bone reabsorption and bone synthesis. These processes are controlled by cell types which are specialised for this purpose. Bone synthesis is based on the deposition of bone matrix by osteoblasts, while bone reabsorption is based on the breakdown of bone matrix by osteoclasts. The majority of bone diseases are due to the balance between bone formation and bone reabsorption being disturbed. Osteoporosis is characterised by a loss of bone matrix. Activated osteoclasts are multinuclear cells, having a diameter of up to 400 $\mu$m which demolish bone matrix. Activated osteoclasts attach themselves to the surface of the bone matrix and secrete proteolytic enzymes and acids into the so-called sealing zone, the region between their cell membrane and the bone matrix. The acid environment and the proteases bring about the breakdown of the bone.

Studies have demonstrated that the attachment of osteoclasts to the bones is regulated by integrin receptors on the cell surface of osteoclasts.

Integrins are a superfamily of receptors which includes, inter alia, the fibrinogen receptor $\alpha_{IIb}\beta_3$ on the blood platelets and the vitronectin receptor $\alpha_V\beta_3$. The vitronectin receptor, $\alpha_V\beta_3$, is a membrane glycoprotein which is expressed on the cell surface of a number of cells such as endothelial cells, cells of the smooth blood vessel musculature, osteoclasts and tumor cells. The $\alpha_V\beta_3$ vitronectin receptor which is expressed on the osteoclast membrane regulates the process of attachment to the bones and of bone reabsorption and consequently contributes to osteoporosis.

In this context, $\alpha_V\beta_3$ binds to bone matrix proteins, such as osteopontin, bone sialoprotein and thrombospondin, which contain the tripeptide motif Arg-Gly-Asp (or RGD).

Horton and coworkers describe RGD peptides and an anti-vitronectin receptor antibody (23C6) which inhibit tooth breakdown by osteoclasts and the migration of osteoclasts (Horton et al., Exp. Cell. Res. 1991, 195, 368). In J. Cell Biol. 1990, 111, 1713, Sato et al. report that echistatin, an RGD peptide from snake venom, is a potent inhibitor of bone reabsorption in a tissue culture and an inhibitor of the attachment of osteoclasts to bones. Fischer et al. (Endocrinology, 1993, 132, 1411) were able to demonstrate that, in the rat, echistatin also inhibits bone reabsorption in vivo.

The $\alpha_V\beta_3$ vitronectin receptor on human cells of the smooth blood vessel musculature of the aorta stimulates migration of these cells into the neointima, a process which finally leads to arteriosclerosis and restenosis following angioplasty (Brown et al., Cardiovascular Res. 1994, 28, 1815).

Brooks et al. (Cell 1994, 79, 1157) have demonstrated that antibodies against $\alpha_V\beta_3$ or $\alpha_V\beta_3$ antagonists are able to shrink tumors by inducing the apoptosis of blood vessel cells during angiogenesis. Chersh et al. (Science 1995, 270, 1500) describe anti-$\alpha_V\beta_3$ antibodies or $\alpha_V\beta_3$ antagonists which inhibit bFGF-induced angiogenesis processes in the rat eye, something which might be of therapeutic value in the treatment of retinopathies.

EP-A 449 079, EP-A 530 505, EP-A 566 919 and WO 93/18057 describe hydantoin derivatives, and WO 95/14008 describes substituted 5-membered ring heterocycles, both of which sets of compounds exhibit thrombocyte aggregation-inhibiting effects. Patent Application WO 94/12181 describes substituted aromatic or non-aromatic ring systems, and WO 94/08577 describes substituted heterocycles, both of which sets of compounds act as fibrinogen receptor antagonists and inhibitors of platelet aggregation. EP-A-528 586 and EP-A-528 587 disclose aminoalkyl-substituted or heterocyclyl-substituted phenylalanine derivatives, and WO 95/32710 describes aryl derivatives, all of which sets of compounds act as inhibitors of bone reabsorption by osteoclasts. WO 95/28426 describes RGD peptides which act as inhibitors of bone reabsorption, angiogenesis and restenosis. WO 96/00574 describes benzodiazepines, and WO 96/00730 describes fibrinogen receptor antagonist templates, in particular benzodiazepines which are linked to a 5-membered ring carrying a nitrogen, both of which sets of compounds act as vitronectin receptor antagonists.

SUMMARY OF THE INVENTION

It is therefore an object of the instant invention to provide the compounds of formula I. It is a further object to provide pharmaceutical compositions of the compounds of formula I, and methods of treating with these compositions diseases associated with vitronectin receptor binding. It is a further object to provide methods for preparing the compounds of formula I. It is a further object to provide an in vitro method of inhibiting the activation of vitronectin receptor using the compounds of formula I.

DETAILED DESCRIPTION OF PREFERRED EMBODIMENTS

The present invention relates to compounds of the formula I and their physiologically tolerated salts, to pharmaceutical preparations comprising these compounds and to their preparation and use as medicaments, in particular as inhibitors of bone reabsorption by osteoclasts, as inhibitors of tumor growth and tumor metastasis, as inflammation inhibitors, for the treatment or prophylaxis of cardiovascular diseases such as arteriosclerosis or restenosis, for the treatment or prophylaxis of nephropathies and retinopathies, for example diabetic retinopathy, and also as vitronectin receptor antagonists for the treatment and prophylaxis of diseases which are based on the interaction between vitronectin receptors and their ligands in cell—cell or cell-matrix interaction processes. The invention furthermore relates to the use of the compounds of the formula I, and their physiologically tolerated salts and pharmaceutical preparations comprising these compounds, as medicaments for alleviating or curing diseases which are associated, at least in part, with an undesirable degree of bone reabsorption, angiogenesis or proliferation of cells of the smooth blood vessel musculature.

The novel compounds of the formula I inhibit bone reabsorption by osteoclasts. Bone diseases against which the novel compounds can be employed are, in particular, osteoporosis, hypercalcemia, osteopenia, e.g. elicited by metastases, dental diseases, hyperparathyroidism, periarticular erosions in rheumatoid arthritis and Paget's disease.

In addition, the compounds of the formula I can be employed for the alleviation, avoidance or therapy of bone diseases which are provoked by glucocorticoid therapy, steroid therapy or corticosteroid therapy, or by a lack of sexual hormone(s). All these diseases are characterized by bone loss which is due to the imbalance between bone synthesis and bone breakdown.

Moreover, the compounds of formula I can be used as carrier of agents which are effective in the treatment of the afore-mentioned diseases thus allowing the specific transfer of said agents to the desired target (=Drug Targeting, see e.g. Targeted Drug Delivery, R. C. Juliano, Handbook of Experimental Pharmacology, Vol. 100, Ed. Born, G. V. R. et al, Springer Verlag), herein incorporated by reference.

The present invention relates to 5-membered ring heterocycles of the formula I, $$\underset{Z \underline{\qquad} Y}{\overset{\overset{O}{\underset{\|}{C}}}{W \underset{\|}{\bigwedge}} N-E-F-G} \qquad (I)$$

in which:

W is $R^1$—A—B—D—C($R^{16}$), $R^1$—A—B—D—C($R^{16}$)=C, $$R^1-A-B-D-L\overset{(A)_m}{\underset{\phantom{X}}{\bigtriangleup}}C$$

or $$R^1-A-B-D-L\overset{(A)_m}{\underset{\phantom{X}}{\bigtriangleup}}C\mathord{=}\mathord{=}C$$

with it being possible for the ring systems $$L\overset{(A)_m}{\underset{\phantom{X}}{\bigtriangleup}}C$$

to contain 1 or 2 heteroatoms from the group N, O and S, to be saturated or unsaturated, once or more than once, and be substituted by 1–3 substituents from $R^{16}$ or substituted, once or twice, by doubly bonded O or S;

Y is C=O, C=S or —CH$_2$—;

Z is N($R^O$), O, S or —CH$_2$—;

A is a direct linkage, (C$_1$–C$_8$)-alkanediyl, —NR$^2$—N=CR$^2$—, —NR$^2$—C(O)—NR$^2$—, —NR$^2$—C(O)O—, —NR$^2$—C(O)S—, —NR$^2$—C(S)—NR$^2$—, —NR$^2$—C(S)—O—, —NR$^2$—C(S)—S—, —NR$^2$—S(O)$_n$—NR$^2$—, —NR$^2$—S(O)$_n$—O—, —NR$^2$—S(O)$_n$—, (C$_3$–C$_{12}$)-cycloalkanediyl, —C≡C—, —NR$^2$—C(O)—, —C(O)—NR$^2$—, —(C$_5$–C$_{14}$)-arylene-C(O)—NR$^2$—, —O—, —S(O)$_n$—, (C$_5$–C$_{14}$)-arylene-, —CO—, (C$_5$–C$_{14}$)-arylene-CO—, —NR$^2$—, —SO$_2$—NR$^2$, —O—C(O)—, —C(O)O—, —N=CR$^2$—, —R$^2$C=N—, —CR$^2$=CR$^3$— or —(C$_5$–C$_{14}$)-arylene-S(O)$_n$—, which in each case can be substituted by NR$^2$ and/or substituted, once or twice, by (C$_1$–C$_8$)-alkanediyl, such as —(C$_1$–C$_8$)-alkanediyl-CO—NR$^2$—(C$_1$–C$_8$)-alkanediyl, —(C$_1$–C$_8$)-alkanediyl-CO—NR$^2$— or —CO—NR$^2$—(C$_1$–C$_8$)-alkanediyl;

B is a direct linkage, (C$_1$–C$_8$)-alkanediyl, (C$_5$–C$_{10}$)-arylene, (C$_3$–C$_8$)-cycloalkanediyl, —C≡C—, —NR$^2$—, —C(O)—, NR$^2$—C(O)—, —C(O)—NR$^2$—, —NR$^2$—C(O)—NR$^2$, —NR$^2$—C(S)—NR$^2$—, —OC(O)—, —C(O)O—, —S(O)—, —S(O)$_2$—, —S(O)—NR$^2$—, —S(O)$_2$—NR$^2$—, —NR$^2$—S(O)—, —NR$^2$—S(O)$_2$—, —O—, —S— or —CR$^2$=CR$^3$—, which in each case can be substituted once or twice by (C$_1$–C$_6$)-alkanediyl, such as

—CH$_2$—⌬—CH$_2$— or —(CH$_2$)$_2$—NR$^2$—C(O)—; or is a divalent radical of a 5- or 6-membered saturated or unsaturated ring which contains 1 or 2 nitrogen atoms and can be substituted, once or twice, by (C$_1$–C$_6$)-alkyl or doubly bonded oxygen or sulfur;

D is a direct linkage, (C$_1$–C$_8$)-alkanediyl, (C$_5$–C$_{10}$)-arylene, —O—, —NR$^2$—, —CO—NR$^2$—, —NR$^2$—CO—, —NR$^2$—C(O)—NR$^2$—, —NR$^2$—C(S)—NR$^2$—, —OC(O)—, —C(O)O—, —CO—, —CS—, —S(O)—, —S(O)$_2$—, —S(O)$_2$—NR$^2$—, —NR$^2$—S(O)—, —NR$^2$—S(O)$_2$—, —S—, —CR$^2$=CR$^3$—, —C≡C—, —NR$^2$—N=CR$^2$—, —N=CR$^2$, —R$^2$C=N— or —CH(OH)—, which in each case can be substituted, once or twice, by (C$_1$–C$_8$)-alkanediyl, —CR$^2$=CR$^3$— or (C$_5$–C$_6$)-arylene, such as

—CH$_2$—⌬—CH$_2$—;

-phenylene-NR$^2$—C(O)— or —(CH$_2$)$_2$—S(O)$_2$—CH$_2$—

E is a direct linkage, (C$_1$–C$_6$)-alkanediyl, (C$_2$–C$_6$)-alkenediyl, (C$_2$–C$_6$)-alkynediyl, phenylene, phenylene-(C$_1$–C$_3$)-alkanediyl or (C$_1$–C$_3$)-alkanediylphenylene;

F is defined as D;

G is $$-\!\!\!\left[\underset{R^5}{\overset{R^4}{|}}\right]\!\!\left[\underset{R^7}{\overset{R^6}{|}}\right]_p\!\!\!-(CH_2)_{\overline{q}}\!-\!R^{10}$$

L is C($R^{16}$) or N;

$R^O$ is H, (C$_1$–C$_8$)-alkyl which is optionally substituted, once or more than once, by fluorine, (C$_3$–C$_{12}$)-cycloalkyl, (C$_3$–C$_{12}$)-cycloalkyl-(C$_1$–C$_8$)-alkyl, (C$_5$–C$_{14}$)-aryl, (C$_5$–C$_{14}$)-aryl-(C$_1$–C$_8$)-alkyl, (C$_1$–C$_8$)-alkyl-C(O)—, (C$_3$–C$_{12}$)-cycloalkyl-C(O), (C$_3$–C$_{12}$)-cycloalkyl-(C$_1$–C$_6$)-alkyl-C(O), (C$_5$–C$_{14}$)-aryl-C(O)— or (C$_5$–C$_{14}$)-aryl-(C$_1$–C$_6$)-alkyl-C(O), with it being possible for the alkyl radicals to be substituted, once or more than once, by fluorine;

$R^1$ is $R^2$—C(=NR$^2$)NR$^2$—, $R^2R^3$N—C(=NR$^2$)—, $R^2R^3$N—C—(=NR$^2$)—NR$^2$, or a 4- or 14-membered, monocyclic or polycyclic, aromatic or non-aromatic ring system which can optionally contain 1–4 heteroatoms from the group N, O and S and can optionally be substituted, once or more than once, by substituents from the group $R^{12}$, $R^{13}$, $R^{14}$ and $R^{15}$;

$R^2$ and $R^3$ are, independently of each other, H, (C$_1$–C$_{10}$)-alkyl, which is optionally substituted, once or more than once, by fluorine, $(C_3-C_{12})$-cycloalkyl, $(C_3-C_{12})$-cycloalkyl-$(C_1-C_8)$-alkyl, $(C_5-C_{14})$-aryl, $(C_5-C_{14})$-aryl-$(C_1-C_8)$-alkyl, $H_2N$, $R^8ONR^9$, $R^8OR^9$, $R^8OC(O)R^9$, $R^8$—$(C_5-C_{14})$-aryl-$R^9$, $R^8R^8NR^9$, HO—$(C_1-C_8)$-alkyl-$NR^8R^9$, $R^8R^8NC(O)R^9$, $R^8C(O)NR^8R^9$, $R^8C(O)R^9$, $R^8R^8N$—$C(=NR^8)$—, $R^8R^8N$—$C(=NR^8)$—$NR^8$— or $(C_1-C_{18})$-alkylcarbonyloxy-$(C_1-C_6)$-alkoxycarbonyl;

$R^4$, $R^5$, $R^6$ and $R^7$ are, independently of each other, H, fluorine, OH, $(C_1-C_8)$-alkyl, $(C_3-C_{12})$-cycloalkyl, $(C_3-C_{12})$-cycloalkyl-$(C_1-C_8)$-alkyl, or $R^8OR^9$, $R^8SR^9$, $R^8CO_2R^9$, $R^8OC(O)R^9$, $R^8$—$(C_5-C_{14})$-aryl-$R^9$, $R^8N(R^2)R^9$, $R^8R^8NR^9$, $R^8N(R^2)C(O)OR^9$, $R^8S(O)_nN(R^2)R^9$, $R^8OC(O)N(R^2)R^9$, $R^8C(O)N(R^2)R^9$, $R^8N(R^2)C(O)N(R^2)R^9$, $R^8N(R^2)S(O)_nN(R^2)R^9$, $R^8S(O)_nR^9$, $R^8SC(O)N(R^2)R^9$, $R^8C(O)R^9$, $R^8N(R^2)C(O)R^9$ or $R^8N(R^2)S(O)_nR^9$;

$R^8$ is H, $(C_1-C_8)$-alkyl, $(C_3-C_{12})$-cycloalkyl, $(C_3-C_{12})$-cycloalkyl-$(C_1-C_8)$-alkyl, $(C_5-C_{14})$-aryl or $(C_5-C_{14})$-aryl-$(C_1-C_8)$-alkyl, with it being possible for the alkyl radicals to be substituted, once or more than once, by fluorine;

$R^9$ is a direct linkage or $(C_1-C_8)$-alkanediyl;

$R^{10}$ is $C(O)R^{11}$, $C(S)R^{11}$, $S(O)_nR^{11}$, $P(O)_nR^{11}$ or a four- to eight-membered, saturated or unsaturated heterocycle which contains 1, 2, 3 or 4 heteroatoms from the group N, O and S, such as tetrazolyl, imidazolyl, pyrazolyl, oxazolyl or thiadiazolyl;

$R^{11}$ is OH, $(C_1-C_8)$-alkoxy, $(C_5-C_{14})$-aryl-$(C_1-C_8)$-alkoxy, $(C_5-C_{14})$-aryloxy, $(C_1-C_8)$-alkylcarbonyloxy-$(C_1-C_4)$-alkoxy, $(C_5-C_{14})$-aryl-$(C_1-C_8)$-alkylcarbonyloxy-$(C_1-C_6)$-alkoxy, $NH_2$, mono- or di-$(C_1-C_8$-alkyl)-amino, $(C_5-C_{14})$-aryl-$(C_1-C_8)$-alkylamino, $(C_1-C_8)$-dialkylaminocarbonylmethyloxy, $(C_5-C_{14})$-aryl-$(C_1-C_8)$-dialkylaminocarbonylmethyloxy or $(C_5-C_{14})$-arylamino or a L- or D-amino acid;

$R^{12}$, $R^{13}$, $R^{14}$ and $R^{15}$ are, independently of each other, H, $(C_1-C_{10})$-alkyl which is optionally substituted, once or more than once, by fluorine, $(C_3-C_{12})$-cycloalkyl, $(C_3-C_{12})$-cycloalkyl-$(C_1-C_8)$-alkyl, $(C_5-C_{14})$-aryl, $(C_5-C_{14})$-aryl-$(C_1-C_8)$-alkyl, $H_2N$, $R^8ONR^9$, $R^8OR^9$, $R^8OC(O)R^9$, $R^8R^8NR^9$, $R^8$—$(C_5-C_{14})$-aryl-$R^9$, HO—$(C_1-C_8)$-alkyl-$N(R^2)R^9$, $R^8N(R^2)C(O)R^9$, $R^8C(O)N(R^2)R^9$, $R^8C(O)R^9$, $R^2R^3N$—$C(=NR^2)$—$NR^2$—, $R^2R^3N$—$C(=NR^2)$, =O or =S; with it being possible for two adjacent substituents from $R^{12}$ to $R^{15}$ also together being —$OCH_2O$—, —$OCH_2CH_2O$— or —$OC(CH_3)_2O$—;

$R^{16}$ is H, $(C_1-C_{10})$-alkyl which is optionally substituted, once or more than once, by fluorine, $(C_3-C_{12})$-cycloalkyl, $(C_3-C_{12})$-cycloalkyl-$(C_1-C_8)$-alkyl, $(C_5-C_{14})$-aryl, $(C_5-C_{14})$-aryl-$(C_1-C_8)$-alkyl, $(C_2-C_{20})$-alkenyl or $(C_2-C_{10})$-alkynyl;

m is 1, 2, 3, 4, 5 or 6;

n is 1 or 2;

p and q are, independently of each other, 0 or 1;

and the physiologically tolerated salts thereof, with compounds being excepted in which $R^1$—A—B—D—$C(R^{16})$ or $R^1$—A—B—D—$C(R^{16})$=C is $R^1$—K—$C(R^{16})$ or $R^1$—K—CH=C ($R^{16}$=H), where, in this case, $R^1$ is X—NH—$C(=NH)$—$(CH_2)p$, $X^1$—NH—$(CH_2)_p$ or 4-imidazolyl-$CH_2$—, with it being possible for p to be an integer from 0 to 3, X is hydrogen, $(C_1-C_6)$-alkyl, $(C_1-C_6)$-alkylcarbonyl, $(C_1-C_6)$-alkoxycarbonyl, $(C_1-C_{18})$-alkylcarbonyloxy-$(C_1-C_6)$-alkoxycarbonyl, $(C_6-C_{14})$-arylcarbonyl, $(C_6-C_{14})$-aryloxycarbonyl, $(C_6-C_{14})$-aryl-$(C_1-C_6)$-alkoxycarbonyl, hydroxyl, $(C_1-C_6)$-alkoxy, $(C_6-C_{14})$-Aryl-$(C_1-C_6)$-alkoxy or amino, with the aryl groups in X being pure carbocycles which are optionally substituted once or more than once, $X^1$ is $(C_4-C_{14})$-arylcarbonyl, $(C_4-C_{14})$-aryloxycarbonyl, $(C_4-C_{14})$-aryl-$(C_1-C_6)$-alkoxycarbonyl, $(C_4-C_{14})$-aryl-$(C_1-C_6)$-alkoxy or R'—NH—C(=N—R"), where R' and R" have, independently of each other, the meanings of X and where the aryl groups in $X_1$ are pure carbocycles which are optionally substituted once or more than once and K is $(C_1-C_6)$-alkanediyl, $(C_3-C_7)$-cycloalkanediyl, phenylene, phenylene-$(C_1-C_6)$-alkanediyl, $(C_1-C_6)$-alkanediyl-phenylene, phenylene-$(C_2-C_6)$-alkenediyl or a divalent radical of a 5- or 6-membered, saturated or unsaturated ring which contains 1 or 2 nitrogen atoms and can be substituted, once or twice, by $(C_1-C_6)$-alkyl or doubly bonded oxygen or sulfur.

The alkyl radicals which appear in the substituents can be straight-chain or branched, saturated or unsaturated once or more than once. The same applies in a corresponding manner to radicals which are derived therefrom, such as alkoxy. Cycloalkyl radicals can be monocyclic, bicyclic or tricyclic.

Monocyclic cycloalkyl radicals are, in particular, cyclopropyl, cyclobutyl, cyclopentyl, cyclohexyl, cycloheptyl and cyclooctyl which, however, can also be substituted, for example by $(C_1-C_4)$-alkyl. Examples of substituted cycloalkyl radicals which may be mentioned are 4-methylcyclohexyl and 2,3-dimethylcyclopentyl.

Bicyclic and tricyclic cycloalkyl radicals can be unsubstituted or be substituted in any suitable positions by one or more oxo groups and/or one or more identical or different $(C_1-C_4)$-alkyl groups, for example methyl groups or isopropyl groups, preferably methyl groups. The free bond of the bicyclic or tricyclic radical can be located in any position in the molecule; the radical can consequently be bonded by way of a bridgehead atom or an atom in a bridge. The free bond can also be located in any stereochemical position, for example in an exo position or an endo position.

Examples of parent compounds of bicyclic ring systems are norbornane (=bicyclo[2.2.1]heptane), bicyclo[2.2.2]octane and bicyclo[3.2.1]octane. An example of a system which is substituted by an oxo group is camphor (=1,7,7-trimethyl-2-oxobicyclo[2.2.1]heptane).

Examples of parent compounds of tricyclic systems are twistane (=tricyclo[4.4.0.0$^{3,8}$]decane, adamantane (=tricyclo[3.3.1.1$^{3,7}$]decane), noradamantane (=tricyclo[3.3.1.0$^{3,7}$]nonane), tricyclo[2.2.1.0$^{2,6}$]heptane, tricyclo[5.3.2.0$^{4,9}$]dodecane, tricyclo[5.4.0.0$^{2,9}$]undecane or tricyclo[5.5.1.0$^{3,11}$]tridecane.

Examples of aryl are phenyl, naphthyl, biphenylyl, anthryl or fluorenyl, with 1-naphthyl, 2-naphthyl and in particular, phenyl being preferred. Aryl radicals, in particular phenyl radicals, can be substituted, once or more than once, preferably once, twice or three times, by identical or different radicals from the group $(C_1-C_8)$-alkyl, in particular $(C_1-C_4)$-alkyl, $(C_1-C_8)$-alkoxy, in particular $(C_1-C_4)$-alkoxy, halogen, such as fluorine, chlorine and bromine, nitro, amino, trifluoromethyl, hydroxyl, methylenedioxy, ethylenedioxy, —$OC(CH_3)_2O$—, cyano, hydroxycarbonyl, aminocarbonyl, $(C_1-C_4)$-alkoxycarbonyl, phenyl, phenoxy, benzyloxy, $(R^{17}O)_2P(O)$, $(R^{17}O)_2P(O)$—O—, in which $R^{17}$=H, ($C_1$–$C_{18}$)-alkyl, ($C_6$–$C_{14}$)-aryl or ($C_6$–$C_{14}$)-aryl-($C_1$–$C_8$)-alkyl or tetrazolyl.

In monosubstituted phenyl radicals, the substituent can be located in the 2, the 3 or the 4 position, with the 3 and the 4 positions being preferred. If phenyl is substituted twice, the substituents can be in the 1, 2 position, 1, 3 position or 1, 4 position relative to each other. Preferably, in phenyl radicals which are substituted twice, the two substituents are arranged in the 3 and the 4 position, based on the linkage site.

Aryl groups can also be monocyclic or polycyclic aromatic ring systems in which from 1 to 5 carbon atoms can be replaced by from 1 to 5 heteroatoms, such as 2-pyridyl, 3-pyridyl, 4-pyridyl, pyrrolyl, furyl, thienyl, imidazolyl, pyrazolyl, oxazolyl, isoxazolyl, thiazolyl, isothiazolyl, tetrazolyl, pyridyl, pyrazinyl, pyrimidinyl, indolyl, isoindolyl, indazolyl, phthalazinyl, quinolyl, isoquinolyl, quinoxalinyl, quinazolinyl, cinnolinyl, β-carbolinyl, or a benzofused, cyclopenta-fused, cyclohexa-fused or cyclohepta-fused derivative of these radicals. These heterocycles can be substituted by the same substituents as the abovementioned carbocyclic aryl systems.

Within this series of aryl groups, those which are preferred are monocyclic or bicyclic aromatic ring systems having 1–3 heteroatoms from the group N, O and S which can be substituted by 1–3 substituents from the group ($C_1$–$C_6$)-alkyl, ($C_1$–$C_6$)-alkoxy, fluorine, Cl, $NO_2$, $NH_2$, trifluoromethyl, OH, ($C_1$–$C_4$)-alkoxycarbonyl, phenyl, phenoxy, benzyloxy or benzyl.

In this context, those aryl groups which are particularly preferred are monocyclic or bicyclic aromatic 5–10 membered ring systems having 1–3 heteroatoms from the group N, O and S which can be substituted by 1–2 substituents from the group ($C_1$–$C_4$)-alkyl, ($C_1$–$C_4$)-alkoxy, phenyl, phenoxy, benzyl or benzyloxy.

The afore-mentioned applies in a corresponding manner to divalent radicals which are derived from alkyl, cycloalkyl and aryl such as alkanediyl, alkenediyl, alkynediyl, cycloalkanediyl and arylene.

Compounds of the formula I are also preferred which carry a lipophilic radical $R^4$, $R^5$, $R^6$ or $R^7$, such as benzyloxycarbonylamino, cyclohexylmethylcarbonylamino, etc.

Compounds of the formula I are furthermore preferred in which $R^1$ is a 4–14-membered, monocyclic or polycyclic, aromatic or non-aromatic ring system which can optionally contain 1–4 heteroatoms from the group N, O and S and can optionally be substituted, once or more than once, by substituents from the group $R^{12}$, $R^{13}$, $R^{14}$ and $R^{15}$, such as

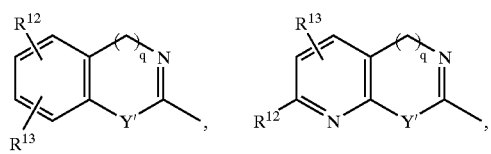

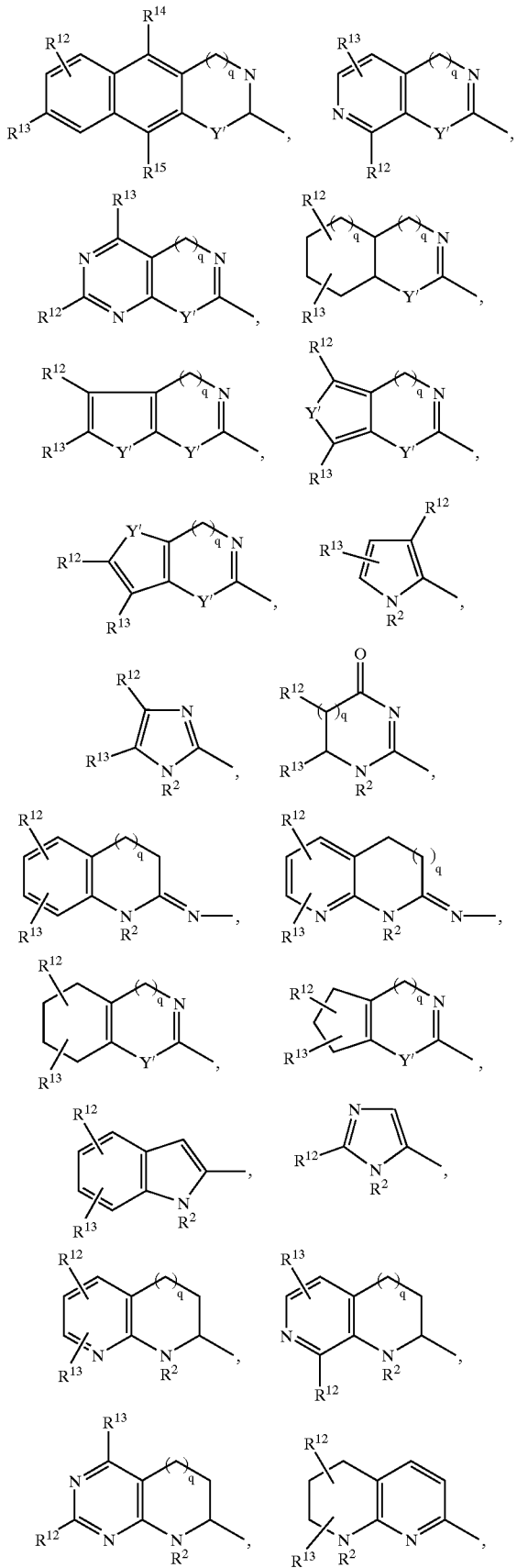

-continued

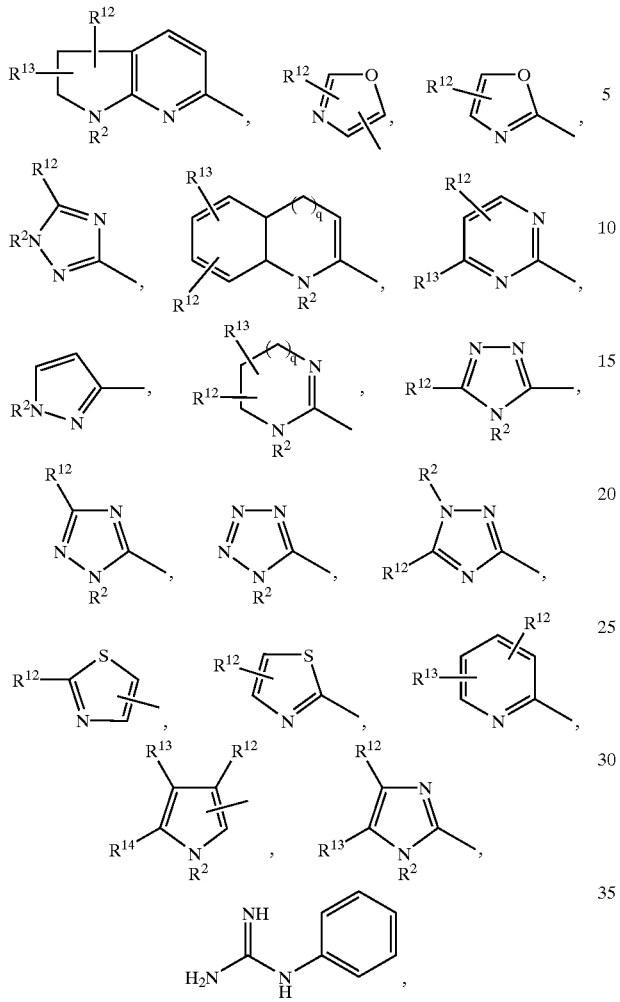

Y' being $NR^2$, O or S.

L- or D-amino acids can be natural or unnatural amino acids. α-Amino acids are preferred. Those which may be mentioned by way of example are (cf. Houben-Weyl, Methoden der organischen Chemie [Methods of Organic Chemistry], Volume XV/1 and 2, Georg Thieme Verlag, Stuttgart, 1974):

Aad, Abu, γAbu, ABz, 2ABz, εAca, Ach, Acp, Adpd, Ahb, Aib, βAib, Ala, βAla, ΔAla, Alg, All, Ama, Amt, Ape, Apm, Apr, Arg, Asn, Asp, Asu, Aze, Azi, Bai, Bph, Can, Cit, Cys, (Cys)$_2$, Cyta, Daad, Dab, Dadd, Dap, Dapm, Dasu, Djen, Dpa, Dtc, Fel, Gin, Glu, Gly, Guv, hAla, hArg, hCys, hGln, hGlu, His, hIle, hLeu, hLys, hMet, hPhe, hPro, hSer, hThr, hTrp, hTyr, Hyl, Hyp, 3Hyp, Ile, Ise, Iva, Kyn, Lant, Lcn, Leu, Lsg, Lys, βLys, ΔLys, Met, Mim, Min, nArg, Nle, Nva, Oly, Orn, Pan, Pec, Pen, Phe, Phg, Pic, Pro, ΔPro, Pse, Pya, Pyr, Pza, Qin, Ros, Sar, Sec, Sem, Ser, Thi, βThi, Thr, Thy, Thx, Tia, Tle, Tly, Trp, Trta, Tyr, Val, tert-butylglycine (Tbg), neopentylglycine (Npg), cyclohexylglycine (Chg), cyclohexylalanine (Cha), 2-thienylalanine (Thia), 2,2-diphenylaminoacetic acid, 2-(p-tolyl)-2-phenylaminoacetic acid and 2-(p-chlorophenyl) aminoacetic acid;

and, in addition:
pyrrolidine-2-carboxylic acid; piperidine-2-carboxylic acid; 1,2,3,4-tetrahydroisoquinoline-3-carboxylic acid; decahydroisoquinoline-3-carboxylic acid; octahydroindole-2-carboxylic acid; decahydroquinoline-2-carboxylic acid; octahydrocyclopenta[b]pyrrole-2-carboxylic acid; 2-azabicyclo[2.2.2]octane-3-carboxylic acid; 2-azabicyclo[2.2.1]-heptane-3-carboxylic acid; 2-azabicyclo[3.1.0]hexane-3-carboxylic acid; 2-azaspiro[4.4]nonane-3-carboxylic acid; 2-azaspiro[4.5]decane-3-carboxylic acid; spiro(bicyclo[2.2.1]heptane)-2,3-pyrrolidine-5-carboxylic acid; spiro(bicyclo[2.2.2]octane)-2,3-pyrrolidine-5-carboxylic acid; 2-azatricyclo[4.3.0.1$^{6,9}$]decane-3-carboxylic acid; decahydrocyclo-hepta[b]pyrrole-2-carboxylic acid; decahydrocycloocta[c]pyrrole-2-carboxylic acid; octahydrocyclopenta[c]pyrrole-2-carboxylic acid; octahydroisoindole-1-carboxylic acid; 2,3,3a,4,6a-hexahydrocyclopenta[b]pyrrole-2-carboxylic acid; 2,3,3a,4,5,7a-hexahydroindole-2-carboxylic acid; tetrahydrothiazole-4-carboxylic acid; isoxazolidine-3-carboxylic acid; pyrazolidine-3-carboxylic acid and hydroxypyrrolidine-2-carboxylic acid, which can all optionally be substituted (see the following formulae):

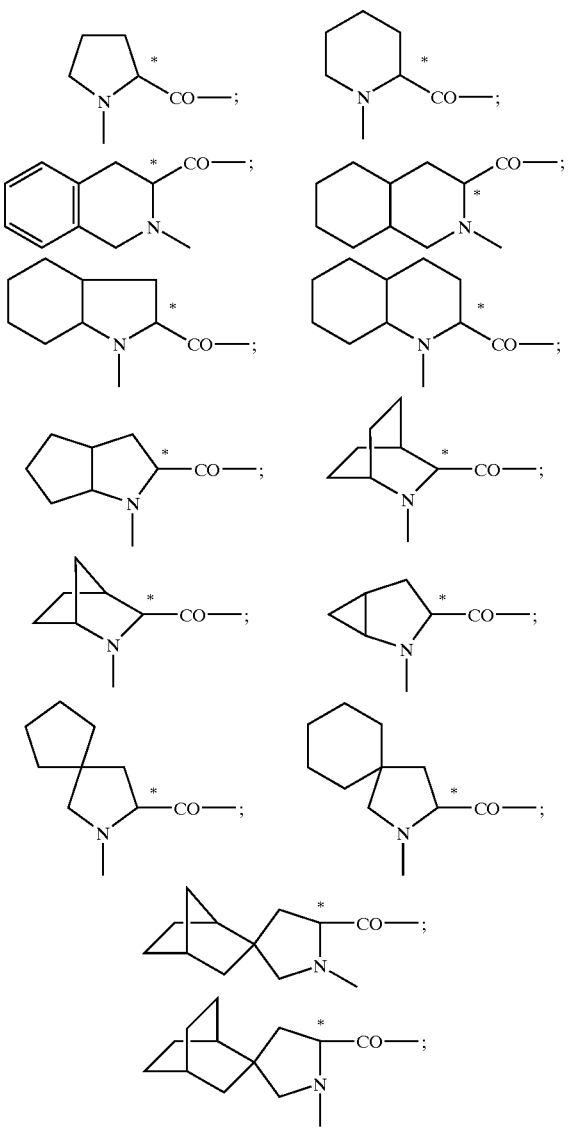

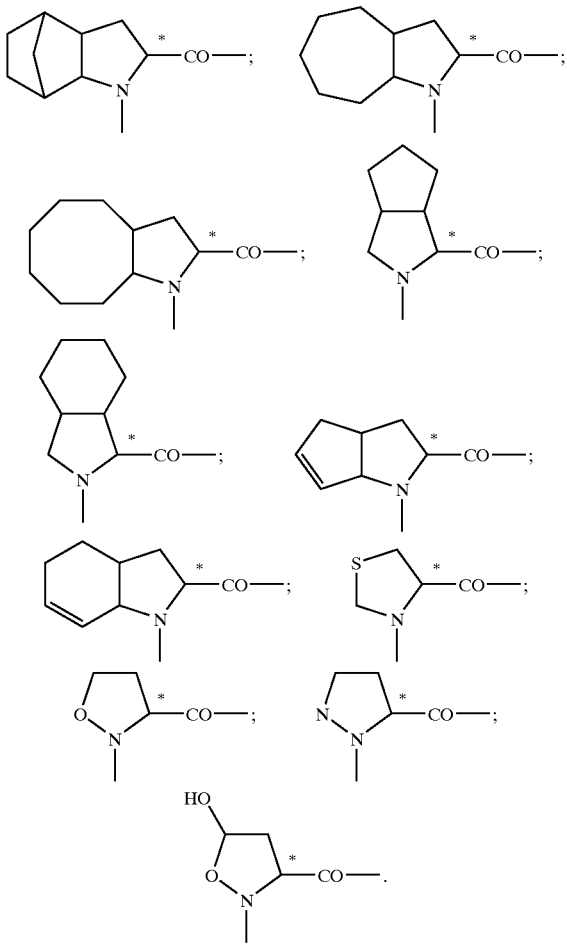

The heterocycles underlying the abovementioned radicals are disclosed, for example, in U.S. Pat. Nos. 4,344,949; 4,374,847; 4,350,704; EP-A 29,488; EP-A 31,741; EP-A 46,953; EP-A 49,605; EP-A 49,658; EP-A 50,800; EP-A 51,020; EP-A 52,870; EP-A 79,022; EP-A 84,164; EP-A 89,637; EP-A 90,341; EP-A 90,362; EP-A 105,102; EP-A 109,020; EP-A 111,873; EP-A 271,865 and EP-A 344,682.

In addition, the amino acids can also be present as esters or amides, such as methyl ester, ethyl ester, isopropyl ester, isobutyl ester, tert-butyl ester, benzyl ester, ethyl amide, semicarbazide or ω-amino-$(C_2-C_8)$-alkylamide.

Functional groups of the amino acids can be protected. Suitable protecting groups, such as urethane protecting groups, carboxyl protecting groups and side-chain protecting groups are described in Hubbuch, Kontakte (Merck) 1979, No. 3, pages 14 to 23, and in Büllesbach, Kontakte (Merck) 1980, No. 1, pages 23 to 35. Those which may be mentioned in particular are: Aloc, Pyoc, Fmoc, Tcboc, Z, Boc, Ddz, Bpoc, Adoc, Msc, Moc, Z($NO_2$), Z($Hal_n$), Bobz, Iboc, Adpoc, Mboc, Acm, tert-butyl, OBzl, ONbzl, OMbzl, Bzl, Mob, Pic, Trt.

Physiologically tolerated salts of the compounds of the formula I are in particular pharmaceutically utilizable or nontoxic salts. These salts are formed, for example, from compounds of the formula I which contain acidic groups, for example carboxyl, using alkali metals or alkaline earth metals, such as Na, K, Mg and Ca, and also using physiologically tolerated organic amines, such as triethylamine, ethanolamine or tris-(2-hydroxyethyl)-amine.

Compounds of the formula I which contain basic groups, for example an amino group, an amidino group or a guanidino group, form salts with inorganic acids, such as hydrochloric acid, sulfuric acid or phosphoric acid, and with organic carboxylic or sulfonic acids, such as acetic acid, citric acid, benzoic acid, maleic acid, fumaric acid, tartaric acid, methanesulfonic acid or p-toluenesulfonic acid.

The novel compounds of the formula I can contain optically active carbon atoms which can, independently of each other, have R or S configurations, and these compounds can consequently be present in the form of pure enantiomers or pure diastereomers or in the form of enantiomeric mixtures or diastereomeric mixtures. Both pure enantiomers and enantiomeric mixtures and also diastereomers and diastereomeric mixtures are part of the subject matter of the present invention.

Over and above this, the novel compounds of the formula I can contain movable hydrogen atoms and can consequently be present in different tautomeric forms. These tautomers are also part of the subject matter of the present invention.

If A, D or F are, independently of each other, $—CR^2=CR^3—$, $—NR^2—N=CR^2—$, $—N=CR^2—$ or $—R^2C=N—$ and/or B is $—CR^2=CR^3—$, and/or W is $R^1—A—B—D—C(R^{16})=C$ or

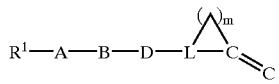

the novel compounds of the formula I can be present as E/Z isomeric mixtures. The present invention relates both to pure E or Z isomers and to E/Z isomeric mixtures. Diastereomers, including E/Z isomers, can be separated into the individual isomers by chromatography. Racemates can be separated into the two enantiomers either by chromatography on chiral phases or by racemate resolution.

Compounds of the formula I are preferred in which:

W is $R^1—A—B—D—C(R^{16})$, $R^1—A—B—D—C(R^{16})=C$,

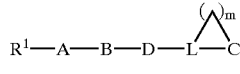

or

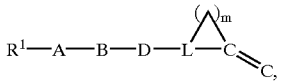

where the ring systems

contain 1 or 2 heteroatoms from the group N and O, can be saturated or unsaturated once, and can be substituted by 1 or 2 substituents from $R^{16}$;

Y is C=O, C=S or $—CH_2—$;

Z is $N(R^0)$, O or $—CH_2—$;

A is a direct linkage, $(C_1-C_6)$-alkanediyl, $—NR^2—N=CR^2—$, $—NR^2—C(O)—NR^2—$, $—NR^2—C(O)O—$, $—NR^2—C(O)S—$, $—NR^2—C(S)—NR^2—$, $—NR^2—C(S)—O—$, $—NR^2—C(S)—S—$, $—NR^2—S$ (O)$_n$—NR$^2$—, —NR$^2$—S(O)$_n$—O—, —NR$^2$—S(O)$_n$—,(C$_3$–C$_8$)-cycloalkanediyl, —C≡C—, —NR$^2$—C(O)—, —C(O)—NR$^2$—, —(C$_5$–C$_{12}$)-arylene-C(O)—NR$^2$—, —O—, —S(O)$_n$—, —(C$_5$–C$_{12}$)-arylene-, —CO—, —(C$_5$–C$_{12}$)-arylene-CO—, —NR$^2$—, —SO$_2$—NR$^2$—, —C(O)O—, —O—C(O)—, —N=CR$^2$—, —R$^2$C=N—, —CR$^2$=CR$^3$—, —(C$_5$–C$_{12}$)-arylene-S(O)$_n$—, which in each case can be substituted by NR$^2$ and/or be substituted, once or twice, by (C$_1$–C$_8$)-alkanediyl;

B is a direct linkage, (C$_1$–C$_6$)-alkanediyl, (C$_5$–C$_8$)-arylene, (C$_3$–C$_8$)-cycloalkanediyl, —C≡C—, —NR$^2$—, —C(O)—, —NR$^2$—C(O)—, —C(O)—NR$^2$—, —NR$^2$—C(O)—NR$^2$—, —S(O)—, —S(O)$_2$—, —S(O)—NR$^2$—, —S(O)$_2$—NR$^2$—, —NR$^2$—S(O)—, —NR$^2$—S(O)$_2$—, —O—, —CR$^2$=CR$^3$—, which in each case can be substituted, once or twice, by (C$_1$–C$_6$)-alkanediyl;

D is a direct linkage, (C$_1$–C$_8$)-alkanediyl, (C$_5$–C$_8$)-arylene, —O—, —NR$^2$—, —CO—NR$^2$—, —NR$^2$—CO—, —NR$^2$—C(O)—NR$^2$—, —NR$^2$—C(S)—NR$^2$—, —OC(O)—, —C(O)O—, —CO—, —CS—, —S(O)—, —S(O)$_2$—, —S(O)$_2$—NR$^2$—, —NR$^2$—S(O)—, —NR$^2$—S(O)$_2$—, —S—, —CR$^2$=CR$^3$—, —C≡C—, —NR$^2$—N=CR$^2$—, —N=CR$^2$— or —R$^2$C=N—, which in each case can be substituted, once or twice, by (C$_1$–C$_6$)-alkanediyl, —CR$^2$=CR$^3$— or (C$_5$–C$_6$)-arylene;

E is a direct linkage, (C$_1$–C$_4$)-alkandeiyl, (C$_2$–C$_4$)-alkenediyl, (C$_2$–C$_4$)-alkynediyl, phenylene, phenylene-(C$_1$–C$_2$)-alkanediyl or (C$_1$–C$_2$)-alkanediylphenylene;

F is defined as D;

G is

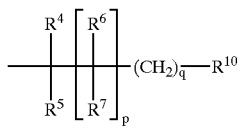

L is C(R$^{16}$) or N;

R$^0$ is H, (C$_1$–C$_6$)-alkyl, (C$_3$–C$_8$)-cycloalkyl, (C$_3$–C$_8$)-cycloalkyl-(C$_1$–C$_6$)-alkyl, (C$_5$–C$_{12}$)-aryl, (C$_5$–C$_{12}$)-aryl-(C$_1$–C$_6$)-alkyl, (C$_1$–C$_8$)-alkyl-C(O), (C$_3$–C$_8$)-cycloalkyl-C(O), (C$_3$–C$_8$)-cycloalkyl-(C$_1$–C$_4$)-alkyl-C(O), (C$_5$–C$_{12}$)-aryl-C(O) or (C$_5$–C$_{12}$)-aryl-(C$_1$–C$_4$)-alkyl-C(O), where the alkyl radicals can be substituted, once or more than once, by fluorine;

R$^1$ is R$^2$—C(=NR$^2$)NR$^3$—, R$^2$R$^3$N—C(=NR$^2$)—, R$^2$R$^3$ N—C(=NR$^2$)—NR$^2$, or a 4–10-membered, monocyclic or polycyclic, aromatic or non-aromatic ring system which can optionally contain 1–4 heteroatoms from the group N, O and S and can optionally be substituted, once or more than once, by substituents from the group R$^{12}$, R$^{13}$, R$^{14}$ and R$^{15}$;

R$^2$ and R$^3$ are, independently of each other, H, (C$_1$–C$_8$)-alkyl which is optionally substituted, once or more than once, by fluorine, (C$_3$–C$_8$)cycloalkyl, (C$_3$–C$_8$)-cycloalkyl-(C$_1$–C$_6$)-alkyl, (C$_5$–C$_{12}$)-aryl, (C$_5$–C$_{12}$)-aryl-(C$_1$–C$_6$)-alkyl, H$_2$N, R$^8$ONR$^9$, R$^8$OR$^9$, R$^8$OC(O)R$^9$, R$^8$—(C$_5$–C$_{12}$)-aryl-R$^9$, R$^8$ R$^8$NR$^9$, HO—(C$_1$–C$_8$)-alkyl-NR$^8$R$^9$, R$^8$R$^8$NC(O)R$^9$, R$^8$C(O)NR$^8$R$^9$, R$^8$C(O)R$^9$, R$^8$R$^8$N—C(=NR$^8$)—, R$^8$R$^8$N—C(=NR$^8$)—NR$^8$— or (C$_1$–C$_{10}$)-alkylcarbonyloxy-(C$_1$–C$_4$)-alkoxycarbonyl;

R$^4$, R$^5$, R$^6$ and R$^7$ are, independently of each other, H, fluorine, OH, (C$_1$–C$_8$)-alkyl, (C$_5$–C$_{12}$)-cycloalkyl, (C$_5$–C$_{12}$)-cycloalkyl-(C$_1$–C$_8$)-alkyl, or R$^8$OR$^9$, R$^8$ SR$^9$, R$^8$CO$_2$R$^9$, R$^8$OC(O)R$^9$, R$^8$—(C$_5$–C$_{12}$)-aryl-R$^9$, R$^8$N(R$^2$)R$^9$, R$^8$R$^8$NR$^9$, R$^8$N(R$^2$)C(O)OR$^9$, R$^8$S(O)$_n$N(R$^2$)R$^9$, R$^8$OC(O)N(R$^2$)R$^9$, R$^8$C(O)N(R$^2$)R$^9$, R$^8$N(R$^2$)C(O)N(R$^2$)R$^9$, R$^8$N(R$^2$)S(O)$_n$N(R$^2$)R$^9$, R$^8$S(O)$_n$R$^9$, R$^8$SC(O)N(R$^2$)R$^9$, R$^8$C(O)R$^9$, R$^8$N(R$^2$)C(O)R$^5$, R$^8$N(R$^2$)S(O)$_n$R$^9$;

R$^8$ is H, (C$_1$–C$_6$)-alkyl, (C$_5$–C$_{12}$)-cycloalkyl, (C$_5$–C$_{12}$)-cycloalkyl-(C$_1$–C$_6$)-alkyl, (C$_5$–C$_{12}$)-aryl or (C$_5$–C$_{12}$)-aryl-(C$_1$–C$_6$)-alkyl, where the alkyl radicals can be substituted, once or more than once, by fluorine;

R$^9$ is a direct linkage or (C$_1$–C$_6$)-alkanediyl;

R$^{10}$ is C(O)R$^{11}$, C(S)R$^{11}$, S(O)$_n$R$^{11}$, P(O)$_n$R$^{11}$ or a 4- to 8-membered, saturated or unsaturated heterocycle which contains 1, 2, 3 or 4 heteroatoms from the group N, O and S;

R$^{11}$ is OH, (C$_1$–C$_6$)-alkoxy, (C$_5$–C$_{12}$)-aryl-(C$_1$–C$_6$)-alkoxy, (C$_5$–C$_{12}$)-aryloxy, (C$_1$–C$_6$)-alkylcarbonyloxy-(C$_1$–C$_4$)-alkoxy, (C$_5$–C$_{12}$)-aryl-(C$_1$–C$_6$)-alkylcarbonyloxy-(C$_1$–C$_6$)-alkoxy, NH$_2$, mono- or di(C$_1$–C$_6$-alkyl)amino, (C$_5$–C$_{12}$)-aryl-(C$_1$–C$_6$)-alkylamino or (C$_1$–C$_6$)-dialkylaminocarbonylmethyloxy;

R$^{12}$, R$^{13}$, R$^{14}$ and R$^{15}$ are, independently of each other, H, (C$_1$–C$_8$)-alkyl, which is optionally substituted, once or more than once, by fluorine, (C$_3$–C$_8$)-cycloalkyl, (C$_3$–C$_8$)-cycloalkyl-(C$_1$–C$_6$)-alkyl, (C$_5$–C$_{12}$)-aryl, (C$_5$–C$_{12}$)-aryl-(C$_1$–C$_6$)-alkyl, H$_2$N, R$^8$ONR$^9$, R$^8$OR$^9$, R$^8$OC(O)R$^9$, R$^8$—(C$_5$–C$_{12}$)-aryl-R$^9$, R$^8$R$^8$NR$^9$, HO—(C$_1$–C$_8$)-alkyl-N(R$^2$)R$^9$, R$^8$N(R$^2$)C(O)R$^9$, R$^8$C(O)N(R$^2$)R$^9$, R$^8$C(O)R$^9$, R$^2$R$^3$N—C(=NR$^2$)—, R$^2$R$^3$N—C(=NR$^3$)—NR$^2$—, =O or =S; where two adjacent substituents from R$^{12}$ to R$^{15}$ can also together be —OCH$_2$O—, —OCH$_2$CH$_2$O— or —OC(CH$_3$)$_2$O—;

R$^{16}$ is H, (C$_1$–C$_8$)-alkyl which is optionally substituted, once or more than once, by fluorine, (C$_3$–C$_8$)-cycloalkyl, (C$_3$–C$_8$)-cycloalkyl-(C$_1$–C$_6$)-alkyl, (C$_5$–C$_{12}$)-aryl, (C$_5$–C$_{12}$)-aryl-(C$_1$–C$_6$)-alkyl, (C$_2$–C$_8$)-alkenyl or (C$_2$–C$_8$)-alkynyl;

m is 3, 4 or 5;

n is 1 or 2; and p and q are, independently of each other, 0 or 1, and the physiologically tolerated salts thereof.

Compounds of the formula I are particularly preferred in which:

W is R$^1$—A—B—D—C(R$^{16}$), R$^1$—A—B—D—C(R$^{16}$)=C or

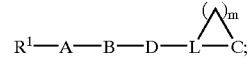

Y is C=O, C=S or —CH$_2$—; preferably C=O or C=S;

Z is N(R$^0$) or —CH$_2$—; preferably N(R$^0$);

A is a direct linkage, (C$_1$–C$_6$)-alkanediyl, —NR$^2$—N=CR$^2$—, —NR$^2$—C(O)—NR$^2$—, —NR$^2$—C(O)O—, —NR$^2$—C(O)S—, —NR$^2$—S(O)$_n$—NR$^2$—, —NR$^2$ —S(O)$_n$—, (C$_3$–C$_6$)-cycloalkanediyl, —C≡C—, —NR$^2$—C(O)—, —C(O)—NR$^2$—, —(C$_5$–C$_{10}$)-arylene-C(O)—NR$^2$—, —O—, —(C$_5$–C$_{10}$)-arylene-, —CO—, (C$_5$–C$_{10}$)-arylene-CO—, —NR$^2$ —, —CO$_2$—, —N=CR$^2$—, —R$^2$C=N— or —CR$^2$=CR$^3$—, which in each case can be substituted by NR$^2$ and/or be substituted, once or twice, by (C$_1$–C$_6$)-alkanediyl;

B is a direct linkage, (C$_1$–C$_6$)-alkanediyl, (C$_5$–C$_6$)-arylene, (C$_5$–C$_6$)-cycloalkanediyl, —C≡C—, —NR$^2$—C(O)—, —C(O)—NR$^2$—, —NR$^2$—S(O)$_2$—, —O— or —CR$^2$=CR$^3$—, which in each case can be substituted, once or twice, by (C$_1$–C$_6$)-alkanediyl;

D is a direct linkage, (C$_1$–C$_6$)-alkanediyl, (C$_5$–C$_6$)-arylene, —O—, —NR$^2$—, —NR$^2$—CO—, —NR$^2$—C(O)—NR$^2$—, —NR$^2$—C(S)—NR$^2$, —OC(O)—, —C(O)—, —S(O)$_2$—NR$^2$—, —NR$^2$—S(O)—, —NR$^2$—S(O)$_2$—, —N=CR$^2$— or —R$^2$C=N—, which in each case can be substituted, once or twice, by (C$_1$–C$_6$)-alkanediyl;

E is a direct linkage, (C$_1$–C$_4$)-alkanediyl or (C$_2$–C$_4$)-alkenediyl;

F is a direct linkage, (C$_1$–C$_6$)-alkanediyl, —O—, —CO—NR$^2$—, —NR$^2$—CO—, —NR$^2$—C(O)—NR$^2$—, —OC(O)—, —C(O)O—, —CO—, —S(O)$_2$—, —S(O)$_2$—NR$^2$—, —NR$^2$—S(O)$_2$—, —CR$^2$=CR$^3$—, —C≡C—, —N=CR$^2$— or —R$^2$C=N—, which in each case can be substituted, once or twice, by (C$_1$–C$_6$)-alkanediyl;

G is

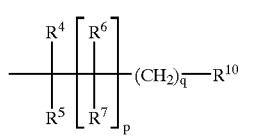

L is C(R$^{16}$) or N;

R$^0$ is H, (C$_1$–C$_6$)-alkyl, (C$_3$–C$_6$)-cycloalkyl, (C$_3$–C$_6$)-cycloalkyl-(C$_1$–C$_4$)-alkyl, (C$_5$–C$_{10}$)-aryl, (C$_5$–C$_{10}$)-aryl-(C$_1$–C$_4$)-alkyl, (C$_1$–C$_6$)-alkyl-C(O)—, (C$_5$–C$_6$)-cycloalkylmethyl-C(O)—, phenyl-C(O) or benzyl-C(O), where the alkyl radicals can be substituted by 1–6 fluorine atoms;

R$^1$ is R$^2$C(=NR$^2$)NR$^2$—, R$^2$R$^3$N—C(=NR$^2$)—,

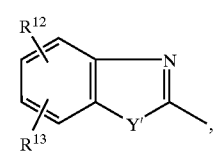 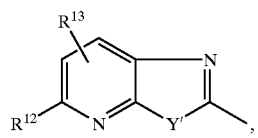

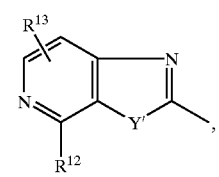 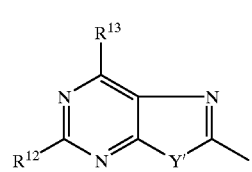

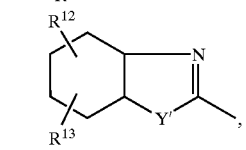 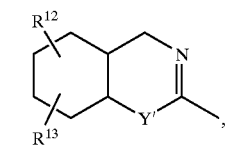 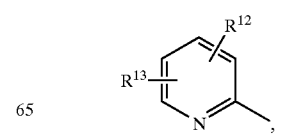

-continued

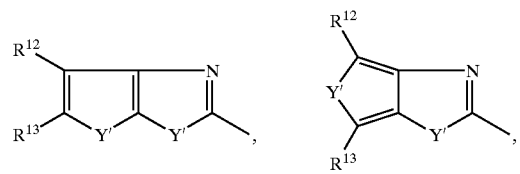

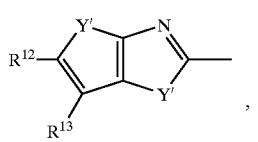 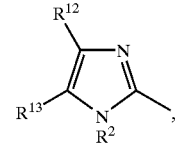

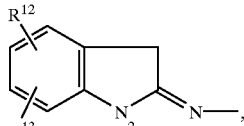 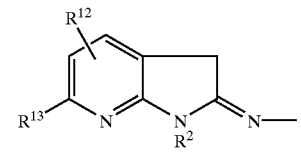

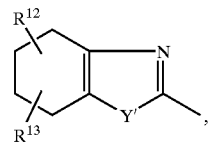 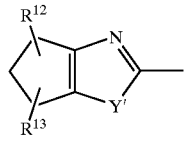

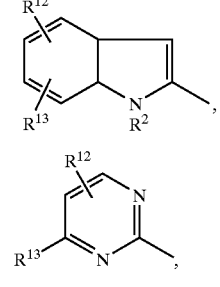 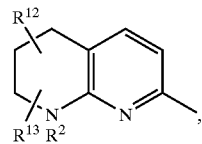

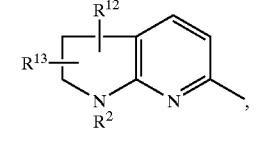 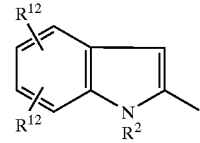

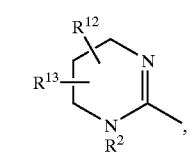 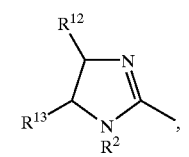

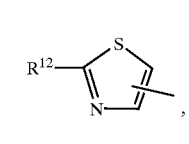 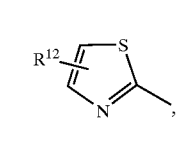

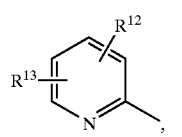 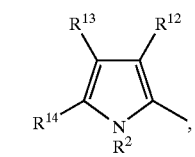

-continued

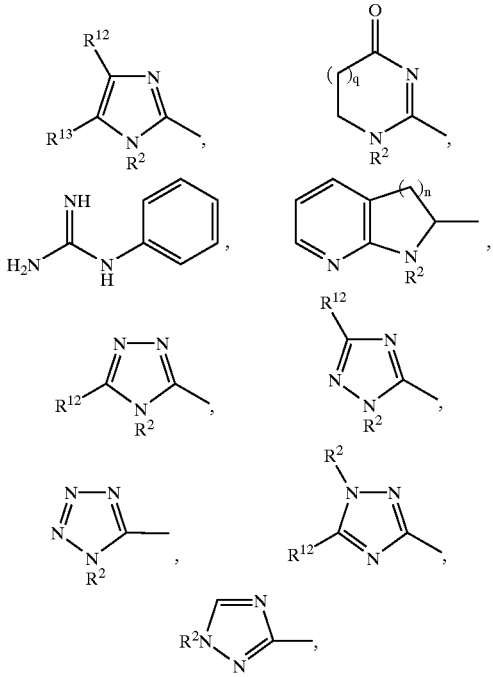

with Y' being NR², O or S.

R² and R³ are, independently of each other, H, $(C_1-C_6)$-alkyl which is optionally substituted, once or more than once, preferably 1–6 times, by fluorine, $(C_3-C_6)$-cycloalkyl, $(C_3-C_6)$-cycloalkyl-$(C_1-C_4)$-alkyl, $(C_5-C_{10})$-aryl, $(C_5-C_{10})$-aryl-$(C_1-C_4)$-alkyl, H₂N, R⁸OR⁹, R⁸—$(C_5-C_{10})$-aryl-R⁹, R⁸NHR⁹, R⁸R⁸NR⁹, R⁸NHC(O)R⁹, R⁸C(O)—, H₂N—C(=NH) or H₂N—C(=NH)—NH—;

R⁴, R⁵, R⁶ and R⁷ are, independently of each other, H, fluorine, OH, $(C_1-C_6)$-alkyl, $(C_6-C_{12})$-cycloalkyl, $(C_6-C_{12})$-cycloalkyl-$(C_1-C_6)$-alkyl, or R⁸OR⁹, R⁸CO₂R⁹, R⁸OC(O)R⁹, R⁸—$(C_5-C_{10})$-aryl-R⁹, R⁸NHR⁹, R⁸R⁸NR⁹, R⁸NHC(O)OR⁹, R⁸S(O)ₙNHR⁹, R⁸OC(O)NHR⁹, R⁸C(O)NHR⁹, R⁸C(O)R⁹, R⁸NHC(O)NHR⁹, R⁸NHS(O)ₙNHR⁹, R⁸NHC(O)R⁹, R⁸NHS(O)ₙR⁹;

R⁸ is H, $(C_1-C_6)$-alkyl, $(C_6-C_{12})$-cycloalkyl, $(C_6-C_{12})$-cycloalkyl-$(C_1-C_4)$alkyl $(C_5-C_{10})$-aryl or $(C_5-C_{10})$-aryl-$(C_1-C_4)$-alkyl, where the alkyl radicals can be substituted by 1–6 fluorine atoms;

R⁹ is a direct linkage or $(C_1-C_6)$-alkanediyl;

R¹⁰ is C(O)R¹¹, S(O)ₙR¹¹ or P(O)ₙR¹¹;

R¹¹ is OH, $(C_1-C_6)$-alkoxy, $(C_5-C_{10})$-aryl-$(C_1-C_6)$-alkoxy, $(C_5-C_{10})$-aryloxy, $(C_1-C_6)$-alkylcarbonyloxy-$(C_1-C_4)$-alkoxy, $(C_5-C_{10})$-aryl-$(C_1-C_4)$-alkylcarbonyloxy-$(C_1-C_4)$-alkoxy, NH₂ or mono- or di($(C_1-C_6)$-alkyl)amino;

R¹², R¹³ and R¹⁴ are H, $(C_1-C_6)$-alkyl, which is optionally substituted, once or more than once, by fluorine, $(C_3-C_6)$-cycloalkyl, $(C_3-C_6)$-cycloalkyl-$(C_1-C_4)$-alkyl, $(C_5-C_{10})$-aryl, $(C_5-C_{10})$-aryl-$(C_1-C_4)$-alkyl, H₂N, R⁸OR⁹, R⁸ OC(O)R⁹, R⁸—$(C_5-C_{10})$-aryl-R⁹, R⁸R⁸NR⁹, R⁸NHC(O)R⁹, R⁸C(O)NHR⁹, H₂N—C(=NH)—, H₂N—C(=NH)—NH— or =O;

where two adjacent substituents from R¹²–R¹⁴ can also together be —OCH₂— or —OCH₂CH₂O—;

R¹⁶ is H, $(C_1-C_6)$-alkyl which can be substituted 1–6 times by fluorine, $(C_3-C_6)$-cycloalkyl, $(C_3-C_6)$-cycloalkyl-$(C_1-C_4)$-alkyl, phenyl, phenyl-$(C_1-C_4)$-alkyl or $(C_2-C_6)$-alkenyl;

m is 3, 4 or 5;

n is 1 or 2; and p and q are, independently of each other, 0 or 1, and the physiologically tolerated salts thereof.

Compounds of the formula I are very particularly preferred in which:

W is R¹—A—B—D—C(R¹⁶) or R¹—A—B—D—CH=C;

Y is C=O or C=S;

Z is N(R⁰);

A is a direct linkage, $(C_1-C_4)$-alkanediyl, —NR²—N=CR²—, —NR²—C(O)—NR²—, —NR²—C(O)C—, —NR²—S(O)ₙ—, —NR²—S(O)ₙ—NR²—, —NR²—CO—, —NR²— or —N=CR², which in each case can be substituted by NH and/or be substituted, once or twice, by $(C_1-C_4)$-alkanediyl;

B is a direct linkage, $(C_1-C_4)$-alkanediyl, phenylene, a divalent radical of pyridine, thiophene or furane, cyclohexanediyl, —C≡C—, —CR²=CR³—, —C(O)—NR²— or —NR²—C(O)—, which in each case can be substituted, once or twice, by $(C_1-C_4)$-alkanediyl;

D is a direct linkage, $(C_1-C_4)$-alkanediyl, phenylene, —O—, —NR²—, —NR²—CO—, —NR²—C(O)—NR²—, —R²N—S(O)₂—NR²—, —NR²—S(O)₂—, —NR²—S(O)—, —N=CR²— or —R²C=N—, which in each case can be substituted, once or twice, by $(C_1-C_4)$-alkanediyl;

E is a direct linkage or $(C_1-C_4)$-alkanediyl;

F is a direct linkage, $(C_1-C_6)$-alkanediyl, —O—, —CO—NR²—, —NR²—CO—, —NR²—C(O)—NR²—, —S(O)₂—NR²—, —NR²—S(O)₂—, —CR²=CR³—, —C≡C—, —N=CR²— or —R²C=N—, which in each case can be substituted, once or twice, by $(C_1-C_4)$-alkanediyl;

G is

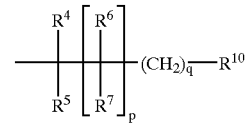

R⁰ is H, $(C_1-C_6)$-alkyl, trifluoromethyl, pentafluoroethyl, $(C_5-C_6)$-cycloalkyl, $(C_5-C_6)$-cycloalkyl-$(C_1-C_2)$-alkyl, optionally substituted phenyl or benzyl which is optionally substituted on the phenyl radical;

R¹ is R²R³N—C(=NR²),

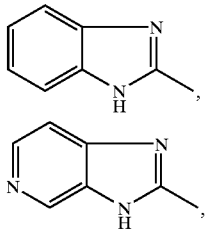

-continued with Y' being NH, O or S.

R² and R³ are, independently of each other, H, (C₁–C₆)-alkyl, trifluoromethyl, pentafluoroethyl, (C₅–C₆)-cycloalkyl, (C₅–C₆)-Cycloalkyl-(C₁–C₂)-alkyl, phenyl, benzyl, H₂N, R⁸OR⁹, R⁸—(C₅–C₁₀)-aryl-R⁹, R⁸NHR⁹, R⁸R⁸NR⁹, R⁸NHC(O)R⁹, H₂N—C(=NH) or H₂C—C(=NH)—NH—;

R⁴, R⁵, R⁶ and R⁷ are, independently of each other, H, fluorine, OH, (C₁–C₆)-alkyl, (C₁₀–C₁₂)-cycloalkyl, (C₁₀–C₁₂)-cycloalkyl-(C₁–C₆)-alkyl, or R⁸OR⁹, R⁸-(C₅–C₁₀)-aryl-R⁹, R⁸R⁸NR⁹, R⁸NHC(O)OR⁹, R⁸S(O)ₙNHR⁹, R⁸ OC(O)NHR⁹ or R⁸C(O)NHR⁹;

R⁸ is H, (C₁–C₆)-alkyl, (C₁₀–C₁₂)-cycloalkyl, (C₁₀–C₁₂)-cycloalkyl-(C₁–C₂)-alkyl, (C₅–C₁₀)-aryl or (C₅–C₁₀)-aryl-(C₁–C₂)-alkyl;

R⁹ is a direct linkage or (C₁–C₆)-alkanediyl;

R¹⁰ is C(O)R¹¹;

R¹¹ is OH, (C₁–C₆)-alkoxy, phenoxy, benzyloxy, (C₁–C₄)-alkylcarbonyloxy-(C₁–C₄)-alkoxy, NH₂, mono- or di(C₁–C₆-alkyl)amino;

R¹⁶ is H, (C₁–C₄)-alkyl, trifluoromethyl, pentafluoroethyl, (C₅–C₆)cycloalkyl, (C₅–C₆)-cycloalkyl-(C₁–C₂)-alkyl, phenyl or benzyl;

n is 1 or 2; and p and q are, independently of each other, 0 or 1, and the physiologically tolerated salts thereof.

Compounds of the formula I are furthermore preferred in which R⁰ is hydrogen, and the physiologically tolerated salts thereof.

Abbreviations Employed:
Boc: t-butoxycarbonyl
DCCl: dicyclohexylcarbodiimide
DMF: dimethylformamide
HOOBt: 3-hydroxy-4-oxo-3,4-dihydro-1,2,3-benzotriazine
THF: tetrahydrofuran
HOBt: 1-hydroxybenzotriazole
TOTU O-[cyano(ethoxycarbonyl)methylenamino]-1,1,3,3-tetramethyluronium tetrafluoroborate
DIPEA: diisopropylethylamine
RT: room temperature
Z: benzyloxycarbonyl In general, compounds of the formula I can be prepared, for example in the course of a conversion synthesis, by linking two or more fragments which can be derived retrosynthetically from the formula I. In general, when the compounds of the formula I are being prepared, it may be necessary, during the course of the synthesis, to temporarily block functional groups, which might give rise, in the particular synthesis step, to undesirable reactions or side reactions, by means of a protecting group strategy which is adapted to the synthesis problem, an approach with which the skilled person is familiar. The method of fragment linkage is not restricted to the subsequent examples but, on the contrary, can be applied generally for synthesizing the compounds of the formula I.

For example, compounds of the formula I of the type $$W \overset{O}{\underset{Z-Y}{\bigtriangleup}} N-E-C(O)NR^2-G,$$

in which F is C(O)NR², can be prepared by condensing a compound of the formula II $$W \overset{O}{\underset{Z-Y}{\bigtriangleup}} N-E-M,$$ II where M is hydroxycarbonyl, (C₁–C₆)-alkoxycarbonyl, activated carboxylic acid derivatives, such as acid chlorides, active esters or mixed anhydrides, with HNR²—G.

In order to condense two fragments with the formation of an amide bond, use is advantageously made of coupling methods of peptide chemistry which are known per se (see, for example, Houben-Weyl, Methoden der Organischen Chemie [Methods of Organic Chemistry], Volumes 15/1 and 15/2, Georg Thieme Verlag, Stuttgart, 1974). For this purpose, it is necessary, as a rule, for nonreacting amino groups which are present to be protected during the condensation by means of reversible protecting groups. The same applies to carboxyl groups which are not involved in the reaction, which groups are preferably employed as ($C_1$–$C_6$)-alkyl, benzyl or tert-butyl esters. Amino group protection is no longer necessary when the amino groups which are to be generated are still present as nitro groups or cyano groups and are only formed, by hydrogenation, after the coupling. After the coupling, the protecting groups which are present are eliminated in an appropriate manner. For example, $NO_2$ groups (guanidino protection), benzyloxycarbonyl groups and benzyl esters can be removed by hydrogenation. The protecting groups of the tert-butyl type are eliminated under acid conditions, while the 9-fluorenylmethyloxycarbonyl radical is removed using secondary amines.

Compounds of the formula I, in which

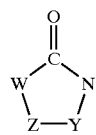

is a dioxo- or thiooxo-oxo-substituted imidazolidine ring, in which W is $R^1$—A—B—D—$C(R^{16})$, can, for example, be obtained:

by reacting α-amino acids or N-substituted α-amino acids, or preferably their esters, for example the methyl ester, ethyl ester, tert-butyl ester or benzyl ester, for example a compound of the formula III

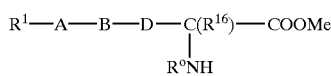

III with an isocyanate or isothiocyanate, for example of the formula U—E—F—G, in which U is isocyanato, isothiocyanato or trichloromethylcarbonylamino, with urea derivatives or thiourea derivatives of the formula IV,

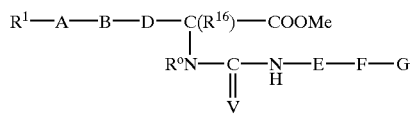

IV in which V is oxygen or sulfur, being obtained, which derivatives are cyclized into compounds of the formula I of the type

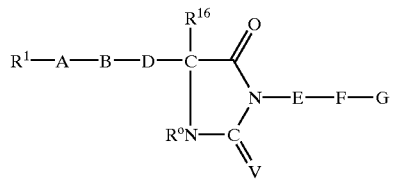

by heating them with acid, with hydrolysis of the ester function.

An example of another method for preparing compounds of the formula I, in which Y is C=O or C=S and W is $R^1$—A—B—D—$C(R^{16})$, is the reaction of compounds of the formula V

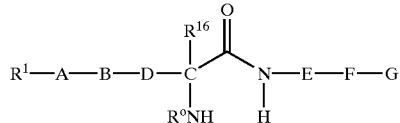

V with phosgene, thiophosgene or corresponding equivalents (in analogy with S. Goldschmidt and M. Wick, Liebigs Ann. Chem. 575 (1952), 217–231 and C. Tropp, Chem. Ber. 61 (1928), 1431–1439).

Compounds of the formula I in which

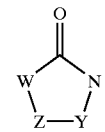

is a heterocycle of the type

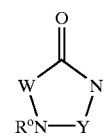

in which Y is C=O or C=S and W is $R^1$—A—B—D—$C(R^{16})$=C, are prepared, for example, in accordance with the following scheme 1:

Scheme 1:

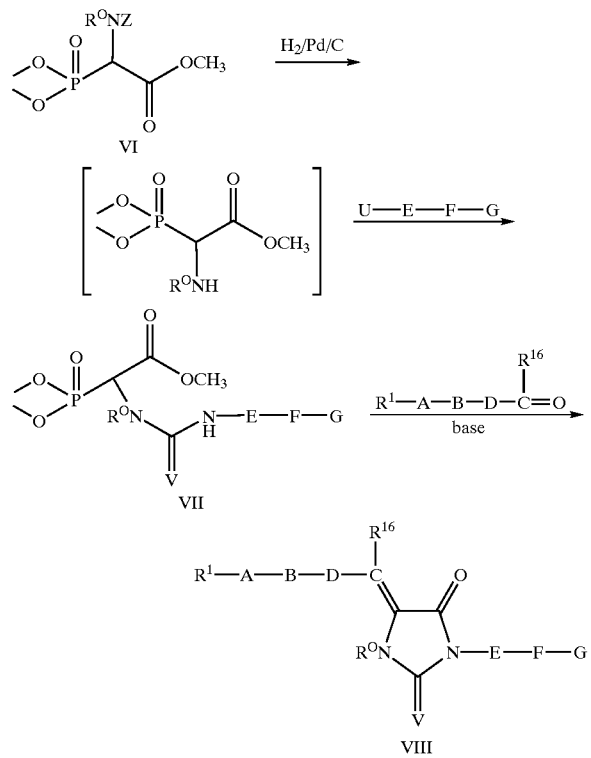

U is —NCO or —NCS; V is O or S.

The conversion of compounds of the formula VI into compounds of the formula VII, and of compounds of the formula VII into compounds of the formula VIII, can be effected, for example, in analogy with S. Chung-gi et al., Tetrahedron Lett 1987, 28 (33), 3827 or U. Schmidt et al. Angew. Chemie 1984, 53.

Another option for preparing compounds of the formula VIII consists, for example, in initially cyclizing compounds of the formula VII, under the influence of acid, to form compounds of the formula XII

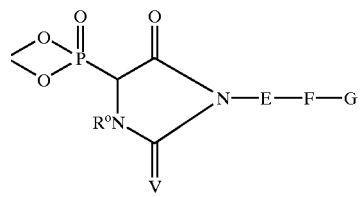

XII and subsequently reacting compounds of the formula XII, in a Horner-Emmons reaction, with

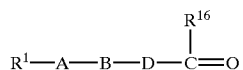

to form compounds of the formula VIII.

Compounds of the formula I, in which

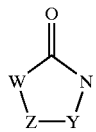

is a heterocycle of the type

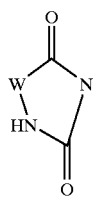

in which W is

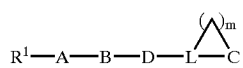

can be prepared, for example, in accordance with the following scheme 2:

Scheme 2:

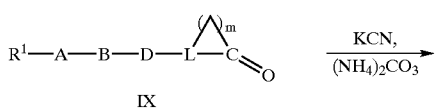

IX

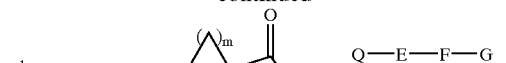
-continued
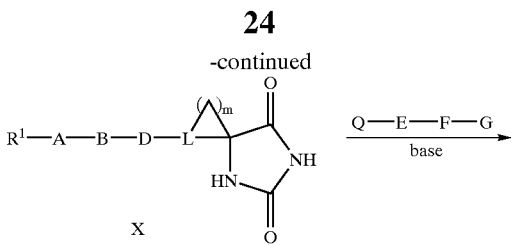

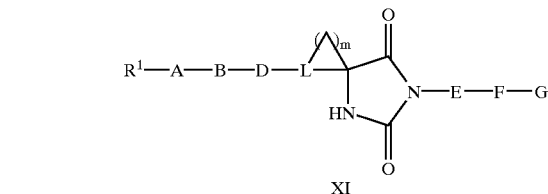

XI

Q is a leaving group which can be substituted nucleophilically, such as halogen, mesylate, tosylate, etc.

The conversion of compounds of the formula IX into compounds of the formula X can be effected, for example, in analogy with E. Marinez et al., Helv. Chim. Acta 1983, 66 (1), 338 or E. W. Logusch et al., J. Org. Chem. 1988, 53 (17), 4069.

Compounds of the formula I in which

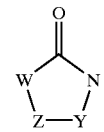

is a heterocycle of the type

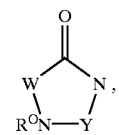

in which Y is C=O or C=S and W is

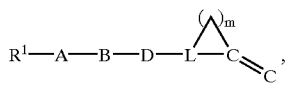

can be prepared, for example, in accordance with the following scheme 3:

Scheme 3:

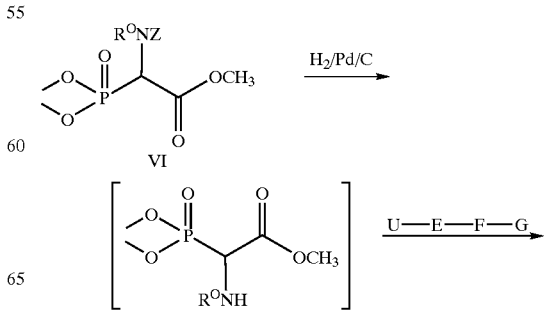

VI

-continued

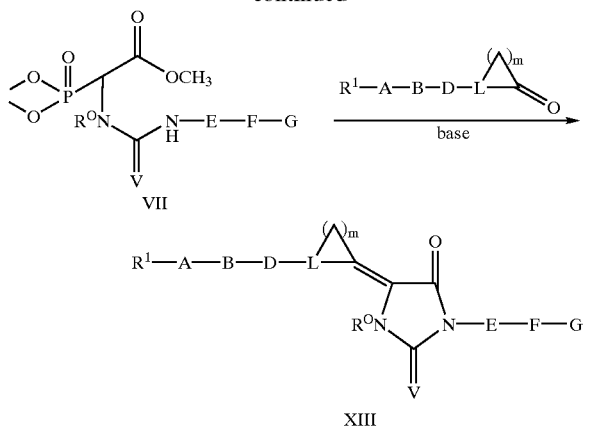

VII

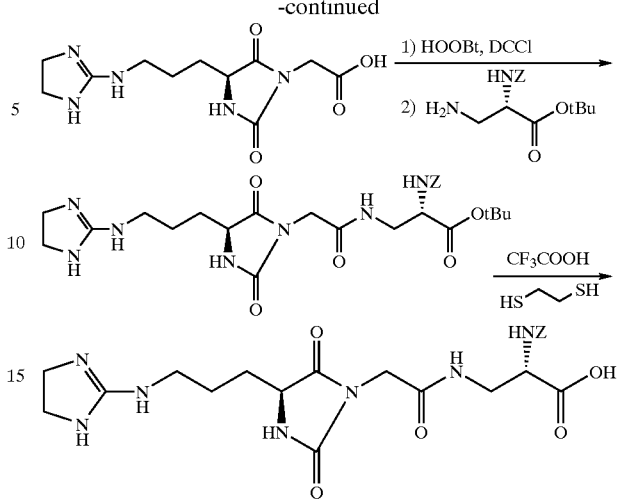

U is —NCO or —NCS; V is O or S.

Another option for preparing compounds of the formula XIII consists, for example, in cyclizing compounds of the formula VII, under the influence of acid, to form compounds of the formula XII and subsequently reacting compounds of the formula XII, in a Horner-Emmons reaction, with

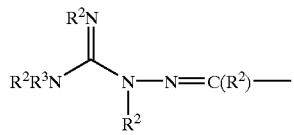

to form compounds of the formula XIII.

However, in the course of a conversion synthesis, it can be advantageous, depending on the meaning of the individual substituents $R^1$, A, B, D etc., to assemble first of all the heterocyclic ring system, which carries only some of the substituents, and then to introduce the remaining substituents, for example in the course of a fragment linkage. As an example, mention may be made here of the synthesis of Example 1:

Scheme 4:

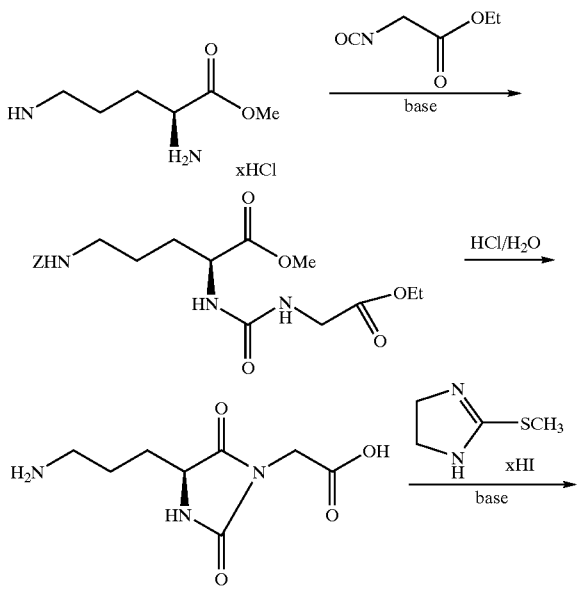

-continued

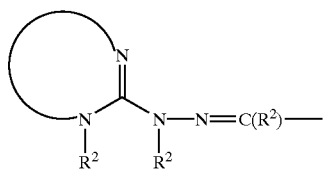

However, this general principle is not restricted to this one example, but rather is generally applicable.

Compounds of the formula I in which $R^1$—A is

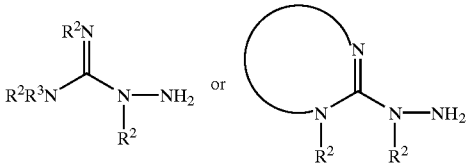

or cyclic guanylhydrazones of the type are prepared, for example, by condensing with ketones or aldehydes of the type $O=C(R^2)$—, or corresponding acetals or ketals, using methods from the current literature, for example in analogy with N. Desideri et al., Arch. Pharm. 325 (1992) 773–777 or A. Alves et al., Eur. J. Med. Chem. Chim. Ther. 21 (1986) 297–304.

Where appropriate, the above guanylhydrazones can be obtained as E/Z isomeric mixtures, which can be resolved using current chromatographic methods.

Compounds of the formula I in which $R^1$—A is $R^2$—C($=NR^2$)$NR^2$—N=C($R^2$)— or a system of the type

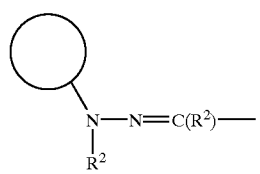

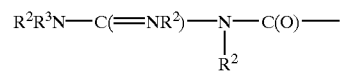

or cyclic acylguanidines of the typ

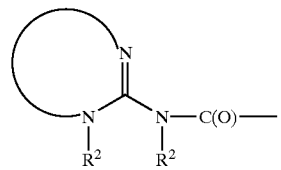

which contains a monocycle or polycycle can be obtained in an analogous manner.

Compounds of the formula I in which $R^{10}$ is $SO_2R^{11}$ are prepared, for example, by oxidizing compounds of the formula I in which $R^{10}$ is SH, using methods which are known from the literature (cf. Houben-Weyl, Methoden der Organischen Chemie, Vol. E12/2, Georg Thieme Verlag, Stuttgart 1985, p. 1058ff), to give compounds of the formula I in which $R^{10}$ is $SO_3H$, from which the compounds of the formula I in which $R^{10}$ is $SO_2R^{11}$ ($R^{11} \neq OH$) are then prepared either directly or by way of the corresponding sulfonic acid halides by esterification or attaching an amide bond. If necessary, oxidation-sensitive groups in the molecule, such as amino, amidino or guanidino groups, are protected with suitable protecting groups before carrying out the oxidation.

Compounds of the formula I in which $R^{10}$ is $S(O)R^{11}$ are prepared, for example, by converting compounds of the formula I in which $R^{10}$ is SH into the corresponding sulfide ($R^{10}$ is $S^{\ominus}$) and subsequently oxidizing them with meta-chloroperbenzoic acid to form the sulfinic acids ($R^{10}$ is $SO_2H$) (cf. Houben-Weyl, Methoden der Organischen Chemie, Vol. E11/1, Georg Thieme Verlag, Stuttgart 1985, p. 618f), from which the corresponding sulfinic esters or amides, $R^{10}$ is $S(O)R^{11}$ ($R^{11} \neq OH$), can be prepared using the methods which are known from the literature. In general, use can also be made of other methods known from the literature for preparing compounds of the formula I in which $R^{10}$ is $S(O)_nR^{11}$ (n is 1 or 2) (cf. Houben-Weyl, Methoden der Organischen Chemie, Vol. E11/1, Georg Thieme Verlag, Stuttgart 1985, p. 618ff or Vol. E11/2, Stuttgart 1985, p. 1055ff).

Compounds of the formula I in which $R^{10}$ is $P(O)R_n^{11}$ (n is 1 or 2) are synthesized from suitable precursors using methods which are known from the literature (cf. Houben-Weyl, Methoden der Organischen Chemie, Vols. E1 and E2, Georg Thieme Verlag, Stuttgart 1982), with the synthesis method which is selected having to be adapted to the target molecule.

Compounds of the formula I in which $R^{10}$ is $C(S)R^{11}$ can be prepared using methods which are known from the literature (cf. Houben-Weyl, Methoden der Organischen Chemie, Vol. E5/1 and E5/2, Georg Thieme Verlag, Stuttgart 1985).

Naturally, compounds of the formula I in which $R^{10}$ is $S(O)_nR^{11}$ (n is 1 or 2), $P(O)R_n^{11}$ (n is 1 or 2) or $C(S)R^{11}$ can also be prepared by fragment linkage, as described above, which is advisable, for example, when E—F—G of the formula I contains, for example, a (commercially available) aminosulfonic acid, aminosulfinic acid, aminophosphonic acid or aminophosphinic acid, or derivatives thereof, such as esters or amides.

Compounds of the formula I in which $R^1$—A is

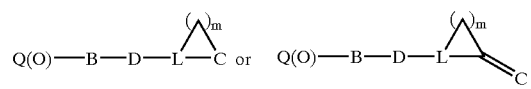

can be prepared, for example, by reacting a compound of the formula I in which W is Q(O)C—B—D—C($R^{16}$)— or Q(O)C—B—D—C($R^{16}$)=C or

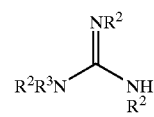

and Q is a leaving group which can be readily substituted nucleophilically, with the corresponding guanidine (derivative) of the type

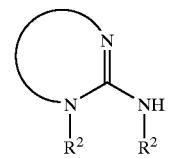

or cyclic guanidine (derivative)

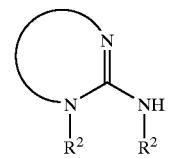

The above activated acid derivatives of the type Q(O)C, in which Q is an alkoxy group, preferably a methoxy group, a phenoxy group, a phenylthio group, a methylthio group, a 2-pyridylthio group or a nitrogen heterocycle, preferably 1-imidazolyl, are advantageously obtained, in a manner known per se, from the underlying carbonyl chlorides, Q is Cl, which, for their part, can in turn be prepared, in a manner known per se, from the underlying carboxylic acids, Q is OH, for example using thionyl chloride.

In addition to the carbonyl chlorides (Q is Cl), other activated acid derivatives of the A type Q(O)C— can also be prepared, in a manner known per se, directly from the underlying carboxylic acids (Q is OH), such as, for example, the methyl esters (Q is $OCH_3$) by treating with gaseous HCl in methanol, the imidazolides (Q is 1-imidazolyl) by treating with carbonyldiimidazole [cf. Staab, Angew. Chem. Int. Ed. Engl. 1, 351–367 (1962)], and the mixed anhydrides (Q is $C_2H_5OC(O)O$ or TosO) using Cl-COO$C_2H_5$ or tosyl chloride, respectively, in the presence of triethylamine in an inert solvent. The carboxylic acids can also be activated with dicyclohexylcarbodiimide (DCCl) or with O-[(cyano (ethoxycarbonyl)methylen)amino]-1,1,3,3-tetramethyluronium-tetrafluoroborate ("TOTU") [Weiss and Krommer, Chemiker Zeitung 98, 817 (1974)] and other activating reagents which are customary in peptide chemistry. A series of suitable methods for preparing activated carboxylic acid derivatives of the formula II is given, with citation of the source literature, in J. March, Advanced Organic Chemistry, Third Edition (John Wiley & Sons, 1985), p. 350.

The reaction of an activated carboxylic acid derivative of the type Q(O)C— with the respective guanidine (derivative) is effected, in a manner known per se, in a protic or aprotic, polar but inert organic solvent. In this context, methanol, isopropanol or THF, at a temperature of from 20° C. up to the boiling temperature of the solvents, have proved to be of value when reacting the methyl esters (Q is OMe) with the respective guanidines. Most reactions of compounds of the type Q(O)C— with salt-free guanidines are advantageously carried out in aprotic, inert solvents such as THF, dimethoxyethane and dioxane. However, when a base (such as NaOH) is employed, water can also be used as solvent when reacting Q(O)C— with guanidines.

When Q is Cl, the reaction is advantageously carried out in the presence of an added acid-capturing agent, for example in the form of excess guanidine (derivative), for the purpose of binding and removing the hydrohalic acid.

Compounds of the formula I in which $R^1$—A is

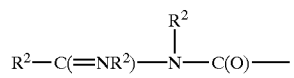

or a system of the type

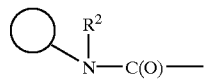

containing a monocycle or polycycle can be obtained in an analogous manner.

Compounds of the formula I in which $R^1$—A is a sulfonyl guanidine or sulfoxyl guanidine of the type $R^2R^3N$—C($=NR^2$)—$NR^2$—S(O)$_n$ (n is 1 or 2) or

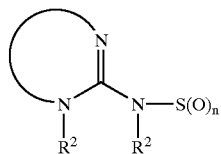

(n is 1 or 2) are prepared, using methods known from the literature, by reacting $R^2R^3N$—C($=NR^3$)$NR^2H$ or

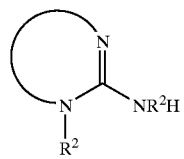

with sulfinic acid derivatives or sulfonic acid derivatives of the formula I in which W is Q—S(O)$_n$—B—D—C($R^{16}$)— or Q—S(O)$_n$—B—D—C($R^{16}$)=C or

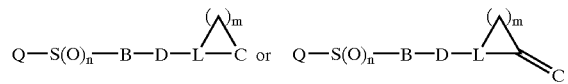

and Q is, for example, Cl or $NH_2$, in analogy with S. Birtwell et al., J. Chem. Soc. (1946) 491 or Houben Weyl, Methoden der Organischen Chemie, Vol. E4, Georg Thieme Verlag, Stuttgart 1983; p. 620 ff.

Compounds of the formula I in which $R^1A$ is $R^2$—C($=NR^2$)$NR^2$—S(O)$_n$ (n is 1 or 2) or a system of the type

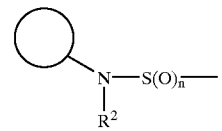

containing a monocycle or polycycle (n is 1 or 2) can be obtained in an analogous manner.

Compounds of the formula I in which A is —$NR^2$—C(O)—$NR^2$—, —$NR^2$—C(O)O— or —$NR^2$—C(O)S— and $R^1$ is $R^2R^3N$—C($=NR^2$), $R^2$—C($=NR^2$) or a 4–14-membered monocyclic or polycyclic, aromatic or non-aromatic ring system, which is specified as described on page 6 and can be substituted as described on that page, are prepared, for example, by first of all reacting a compound of the formula I, in which W is Q—B—D—C($R^{16}$)— or Q—B—D—C($R^{16}$)=C or

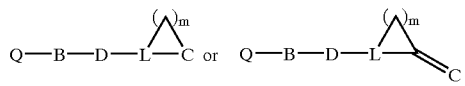

and Q is $HNR^2$—, HO— or HS—, with a suitable carbonic acid derivative, preferably phosgene, diphosgene (trichloromethyl chloroformate), triphosgene (bis(trichloromethyl)carbonate), ethyl chloroformate, i-butyl chloroformate, bis-(1-hydroxy-1-H-benzotriazolyl) carbonate or N,N'-carbonyldiimidazole, in a solvent which is inert towards the reagents employed, preferably DMF, THF or toluene, at a temperature of between −20° C. and the boiling point of the solvent, preferably between 0° C. and 60° C., to form a substituted carbonic acid derivative of the formula I, in which W is

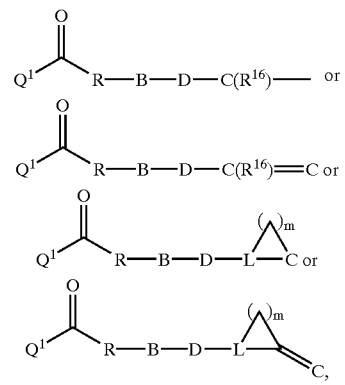

R is —$NR^2$—, —O— or —S— and Q' is chlorine, ethoxy, isobutoxy, benzotriazol-1-oxy or 1-imidazolyl, depending on the carbonic acid derivative employed.

The reaction of these derivatives with $R^2R^3N-C(=NR^2)-NR^2H$ or $R^2-C(=NR^2)-NR^2H$ or with the systems of the type

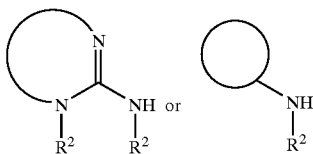

containing a monocycle or polycycle are effected as described above in association with the preparation of acylguanidine (derivatives).

Compounds of the formula I, in which F is $R^2N-C(O)-NR^2$ or $R^2N-C(S)-NR^2$, are prepared, for example, by reacting a compound of the type

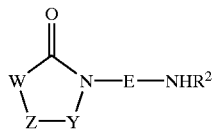

with an isocyanate OCN—G or isothiocyanate SCN—G using methods which are known from the literature.

Compounds of the formula I, in which F is $C(O)NR^2$, $-SO_2NR^2-$ or $-C(O)O-$, can be obtained, for example, by reacting

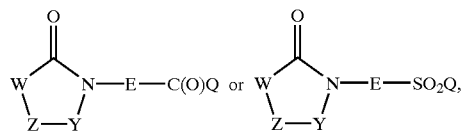

(Q is a leaving group which can readily be substituted nucleophilically, such as OH, Cl, OMe etc.) with $HR^2N-G$ or HO—G in accordance with methods which are known from the literature.

Compounds of the formula I, in which $R^1-A$ comprises a monocycle or polycycle of the type

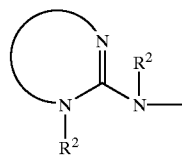

can, for example, be prepared by reacting a compound of the formula I, in which W is $HR^2N-B-D-C(R^{16})-$ or $HR^2N-B-D-C(R^{16})=C$ or

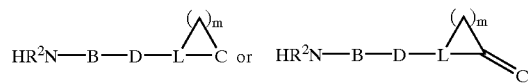

with a monocycle or polycycle of the type

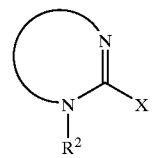

in which X is a leaving group which can be substituted nucleophilically, such as halogen or SH, $SCH_3$, $SOCH_3$, $SO_2CH_3$, $SO_3H$ or HN—$NO_2$ using methods which are known from the literature (see, for example, A. F. Mckay et al., J. Med. Chem. 6 (1963) 587, M. N. Buchman et al., J. Am. Chem. Soc. 71 (1949), 766, F. Jung et at., J. Med. Chem. 34 (1991) 1110 or G. Sorba et al., Eur. J. Med. Chem. 21 (1986), 391).

Compounds of the formula I, in which $R^1A$ comprises a monocycle or polycycle of the type

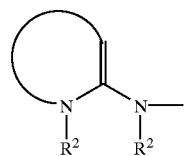

can be prepared, for example, by reacting a compound of the formula I, in which W is $HR^2N-B-D-C(R^{16})-$ or $HR^2N-B-D-C(R^{16})=C$ or

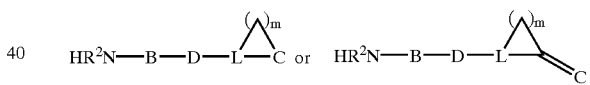

with a compound of the type

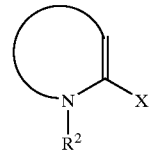

in which X is a leaving group, such as —$SCH_3$, using methods which are known from the literature (cf., e.g., T. Hiroki et al., Synthesis (1984) 703 or M. Purkayastha et al., Indian J. Chem. Sect. B 30 (1991) 646).

Compounds of the formula I in which $R^1A$ is a bis-aminotriazole or a bis-aminooxadiazole radical, can be prepared, for example, as described by P. J. Garrett et al., Tetrahedron 49 (1993) 165 or R. Lee Webb et al., J. Heterocyclic Chem. 24 (1987) 275 in accordance with the following reaction sequence:

Scheme 5:

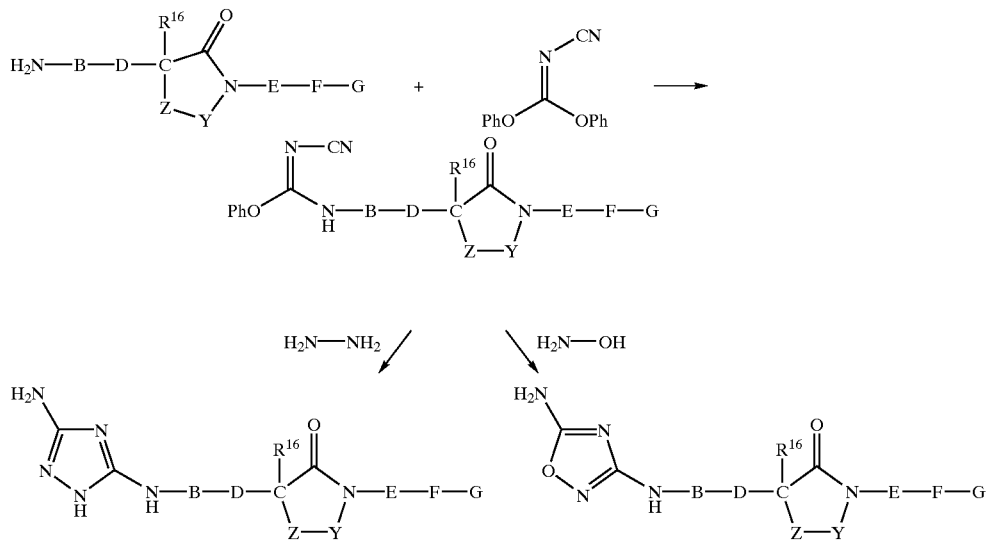

Preparation methods which are known from the literature are described, for example, in J. March, Advanced Organic Chemistry, Third Edition (John Wiley & Sons, 1985).

Another embodiment of the instant invention includes a pharmaceutical composition containing a vitronectin receptor antagonistic amount of the compounds of formula I and a pharmaceutically acceptable carrier. By antagonistic amount it is meant an amount effective to curtail or prevent binding of natural ligand to vitronectin receptor, thereby preventing or ameliorating diseases or conditions associated with such binding. This amount is determined on a case by case basis depending on variables well known to the skilled artisan, such as the nature and state of the disease or condition, and the age and weight and physical condition of the recipient of the pharmaceutical.

The instant invention further includes a method of treating a disease or condition associated with vitronectin receptor binding comprising administering to a mammal this pharmaceutical composition. By treatment it is meant preventing, alleviating, or otherwise ameliorating diseases or conditions associated with vitronectin receptor binding. Such diseases and conditions include but are not limited to bone reabsorption by osteoclasts, tumor growth and tumor metastasis, inflammation, cardiovascular diseases, nephropathies and retinopathies.

Thus in one embodiment, the compounds of the formula I, and their physiologically tolerated salts, may be administered to animals, preferably mammals, and in particular humans, as medicaments, either alone, in mixtures with each other, or in the form of pharmaceutical preparations which permit enteral or parenteral use and which comprise, as the active constituent, an effective dose of at least one compound of the formula I, or a salt thereof, in addition to the customary pharmaceutically unobjectionable carrier substances and auxiliary substances. The preparations normally comprise from about 0.5 to 90% by weight of the therapeutically active compound.

The medicaments may be administered orally, for example in the form of pills, tablets, lacquer tablets, coated tablets, granules, hard gelatin capsules, soft gelatin capsules, solutions, syrups, emulsions, suspensions or aerosol mixtures. However, the administration can also be effected rectally, for example in the form of suppositories, or parenterally, for example in the form of injection solutions or infusion solutions, microcapsules or rods, percutaneously, for example in the form of ointments or tinctures, or nasally, for example in the form of nasal sprays.

The pharmaceutical preparations are produced in a manner known per se, using pharmaceutically inert inorganic or organic carrier substances. For example, lactose, cornstarch or derivatives thereof, talc, stearic acid or its salts, etc. can be used for preparing pills, tablets, coated tablets and hard gelatin capsules. Examples of carrier substances for soft gelatin capsules and suppositories are fats, waxes, semisolid and liquid polyols, natural or hardened oils, etc. Examples of suitable carrier substances for preparing solutions and syrups are water, sucrose, invert sugar, glucose, polyols, etc. Suitable carrier substances for preparing injection solutions are water, alcohols, glycerol, polyols, vegetable oils, etc. Suitable carrier substances for microcapsules, implants or rods are mixed polymers composed of glycolic acid and lactic acid.

In addition to the active compounds and carrier substances, the pharmaceutical preparations can also comprise additives, such as filters, extenders, disintegrants, binders, glidants, wetting agents, stabilizers, emulsifiers, preservatives, sweeteners, dyes, flavorants or aromatizing agents, thickeners, diluents and buffering substances, and also solvents or solubilizers or agents for achieving a slow-release effect, and also salts for altering the osmotic pressure, coating agents or antioxidants. They can also comprise two or more compounds of the formula I or their physiologically tolerated salts; they can furthermore comprise one or more different therapeutically active compounds in addition to at least one compound of the formula I.

The dose can vary within wide limits and has to be adjusted to the individual circumstances in each individual case.

In the case of oral administration, the daily dose can be from 0.01 to 50 mg/kg, preferably from 0.1 to 5 mg/kg, preferably from 0.3 to 0.5 mg/kg, of body weight in order to achieve effective results while, in the case of intravenous administration, the daily dose is generally from about 0.01 to 100 mg/kg, preferably from 0.05 to 10 mg/kg, of body weight. The daily dose may be subdivided into several, for example 2, 3 or 4, subdoses, particularly when relatively large quantities are being administered. Where appropriate, it may be necessary, depending on the individual response, to diverge from the specified daily dose either in an upward or a downward direction.

Another embodiment of the instant invention includes an in vitro method of inhibiting the activation of vitronectin receptor in viable cells by delivering to these cells the compound of formula I, so that the compound competes with natural vitronectin ligand for binding but does not induce a biological response. Parameters and techniques for in vitro inhibition of cell receptors are known to those of skill in the art.

EXAMPLES

The products were characterized by mass spectra and/or NMR spectra.

Example 1

(2S)-Benzoylcarbonylamino-3-[2-((4S)-(3-(4,5dihydro-1H-imidazol-2-ylamino)propyl)-2,5-dioxoimidazolidin-1-yl)acetylamino]propionic Acid (1.8)

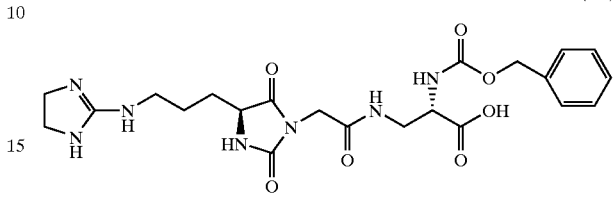

The synthesis was carried out in accordance with the following reaction sequence:

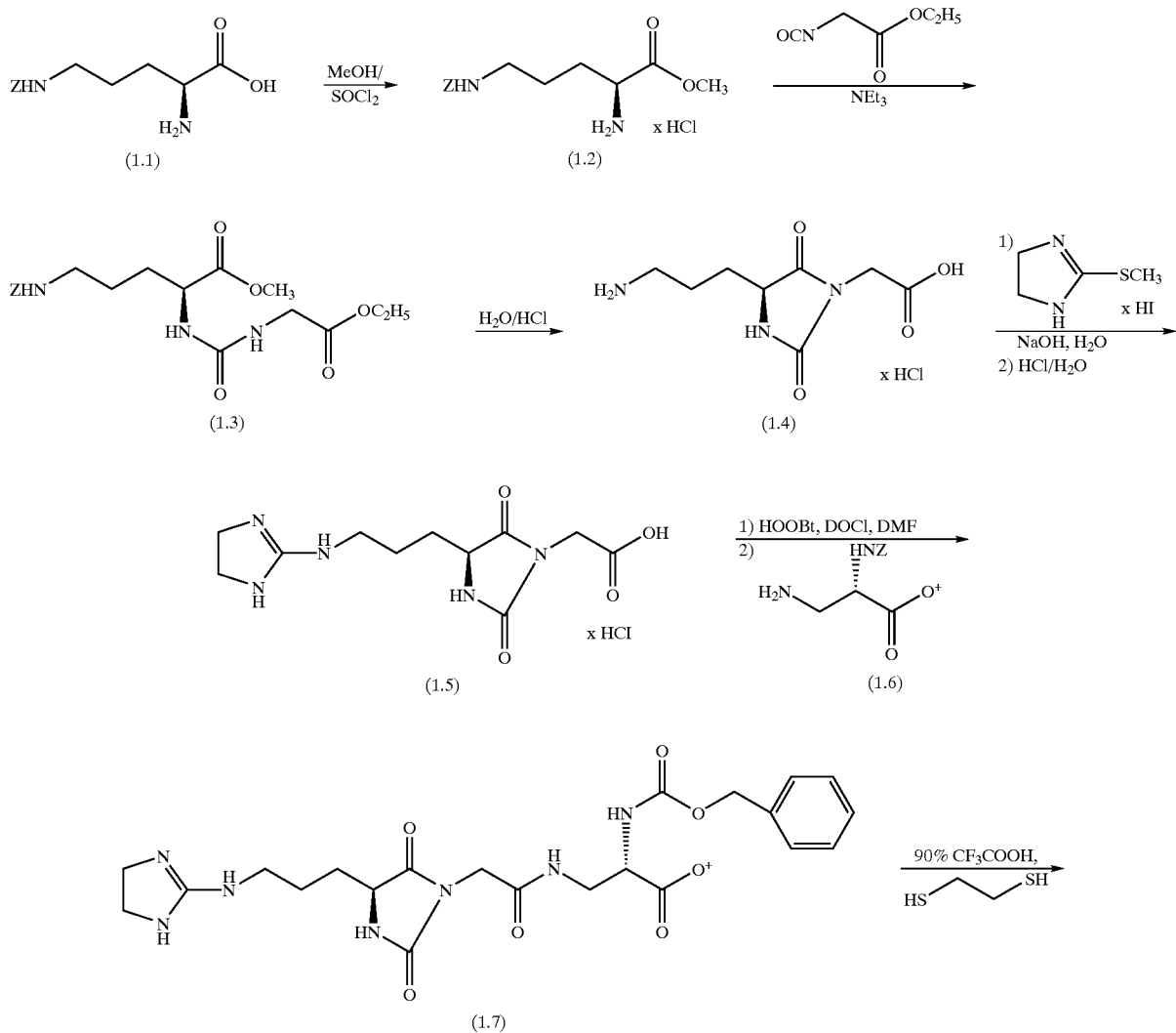

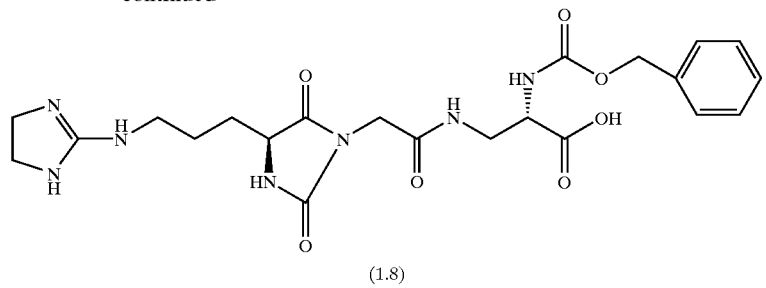

(1.8)

1a) Methyl (2S)-2-amino-5-benzyloxy- carbonylaminopentanoate hydrochloride (1.2)

While cooling with ice, and under an argon atmosphere, 240 ml of thionyl chloride are added dropwise to 300 ml of abs. methanol, after which 40 g (150 mmol) of (2S)-2-amino-5-benzyloxycarbonylaminopentanoic acid (1.1) are added and the mixture is allowed to react at room temperature for 3 h and at 4° C. overnight. The solution is poured into methyl tert-butyl ether, the solvent is decanted off and the residue is triturated with diethyl ether. After filtering off with suction, 29.14 g (61%) of (1.2) are obtained as a colorless solid.

1b) Methyl 5-benzyloxycarbonylamino-(2S)-(3-ethoxycarbonylmethylurea)pentanoate (1.3)

3.83 g (29.7 mmol) of ethyl isocyanatoacetate, and then 3 g (29.7 mmol) of triethylamine are added dropwise, at 0° C. and while stirring, to a solution of 9.41 g (29.7 mmol) of the compound (1.2) in 150 ml of dichloromethane/tetrahydrofuran (2:1). After 30 min at 0° C., the ice bath is removed and the reaction mixture is stirred at room temperature for a further 1.5 h. After removing the solvent in vacuo, the residue is chromatographed through silica gel using ethyl acetate. The product fractions are concentrated and the residue is triturated with ether and filtered off with suction. 11.02 g (83%) of (1.3) are obtained as a colorless solid.

1c) [(4S)-(3-Aminopropyl)-2,5-dioxoimidazolidin-1-yl] acetic Acid Hydrochloride (1.4)

10.4 g (42.9 mmol) of (1.3) are heated to reflux for 45 min together with 100 ml of 6N hydrochloric acid. The solution is concentrated, water is added to the residue and the whole is freeze-dried. 7.1 g (66%) of (1.4) are obtained as a colorless solid.

1d) [(4S)-(3-(4,5-Dihydro-1H-imidazol-2-ylamino) propyl)-2,5-dioxoimidazolidin-1-yl]acetic Acid Hydrochloride (1.5)

400 mg (1.59 mmol) of (1.4) and 388 mg (1.59 mmol) of 2-(methylmercapto)-2-imidazoline hydroiodide are dissolved in 5 ml of $H_2O$. The mixture is adjusted to pH 9 with 1N NaOH and heated at 60° C. for 2.5 h, with the pH of the solution being maintained at 9 by adding 1N NaOH (total consumption of 1N NaOH: 3.4 ml). The reaction mixture is left to stand at room temperature for 3 days, the pH is adjusted to 1 with 1N HCl, the solvent is removed in vacuo and the residue is chromatographed through silica gel using MeOH/$H_2O$=9/1. The product fractions are concentrated and freeze-dried. 230 mg (45%) of (1.5) are obtained as a colorless powder.

1e) tert-Butyl (2S)-3-amino-2-benzyloxy- carbonylaminopropionate (1.6)

10 g (42 mmol) of (2S)-3-amino-2-benzyloxycarbonylaminopropionic acid are shaken in an autoclave for 3 days, at an $N_2$ pressure of 20 atm., in a mixture consisting of 100 ml of dioxane, 100 ml of isobutylene and 8 ml of conc. $H_2SO_4$. Excess isobutylene is blown off and 150 ml of diethyl ether and 150 ml of a saturated solution of $NaHCO_3$ are added to the remaining solution. The phases are separated and the aqueous phase is extracted twice with 100 ml of diethyl ether on each occasion. The combined organic phases are washed with 2×100 ml of $H_2O$ and dried over $Na_2SO_4$. 9.58 g (78%) of (1.6) are obtained as a pale yellow oil after the solvent has been removed in vacuo.

1f) tert-Butyl (2S)-benzoyloxycarbonylamino-3-[2-((4S)-(3-(4,5-dihydro-1H-imidazol-2-ylamino)propyl)-2,5-dioxoimidazolidin-1-yl)acetylamino]propionate (1.7)

200 mg (0.7 mmol) of (1.5) and 114 mg (0.7 mmol) of HOOBt are suspended in 5 ml of DMF, and 154 mg (0.7 mmol) of DCCl are added at 0° C. The mixture is stirred at 0° C. for 1 h, and at RT for 1 h, and 206 mg (0.7 mmol) of (1.6) are then added; the mixture is stirred at RT for 2 h and left to stand at RT overnight. The solvent is removed in vacuo and the residue is chromatographed through silica gel using dichloromethane/methanol/glacial acetic acid/water= 8/2/0.2/0.2. After concentrating and freeze-drying, 105 mg (27%) of (1.7) are obtained as a colorless solid.

1g) (2S)-Benzyloxycarbonylamino-3-[2-((4S)-(3-(4,5-dihydro-1H-imidazol-2-ylamino)propyl)-2,5-dioxoimidazolidin-1-yl)-acetylamino]propionic Acid (1.8)

105 mg (0.188 mmol) of (1.7) are dissolved in a homogeneous solution of 2 ml of 90% trifluoroacetic acid and 0.2 ml of 1,2-dimercaptoethane, and the solution is left to stand at RT for 1 h. After concentrating in vacuo, the residue is partitioned between diethyl ether and water and the aqueous phase is freeze-dried. Following chromatography through ®Sephadex LH 20 using $H_2O$/n-butanol/HOAc=43/4.3/3.5 and subsequent freeze-drying, 45 mg (48%) of (1.8) are obtained as a colorless solid.

Example 2

3-[2-((4S)-(3-(5-Amino-2H-[1.2.4]triazol-3-ylamino) propyl)-2,5-dioxoimidazolidin-1-yl)acetylamino]-(2S)-benzyloxycarbonylaminopropionic Acid (2.5)

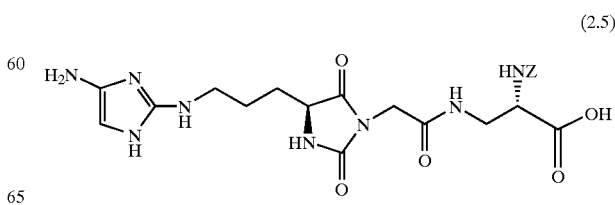

(2.5)

The synthesis was carried out in accordance with the following reaction sequence:

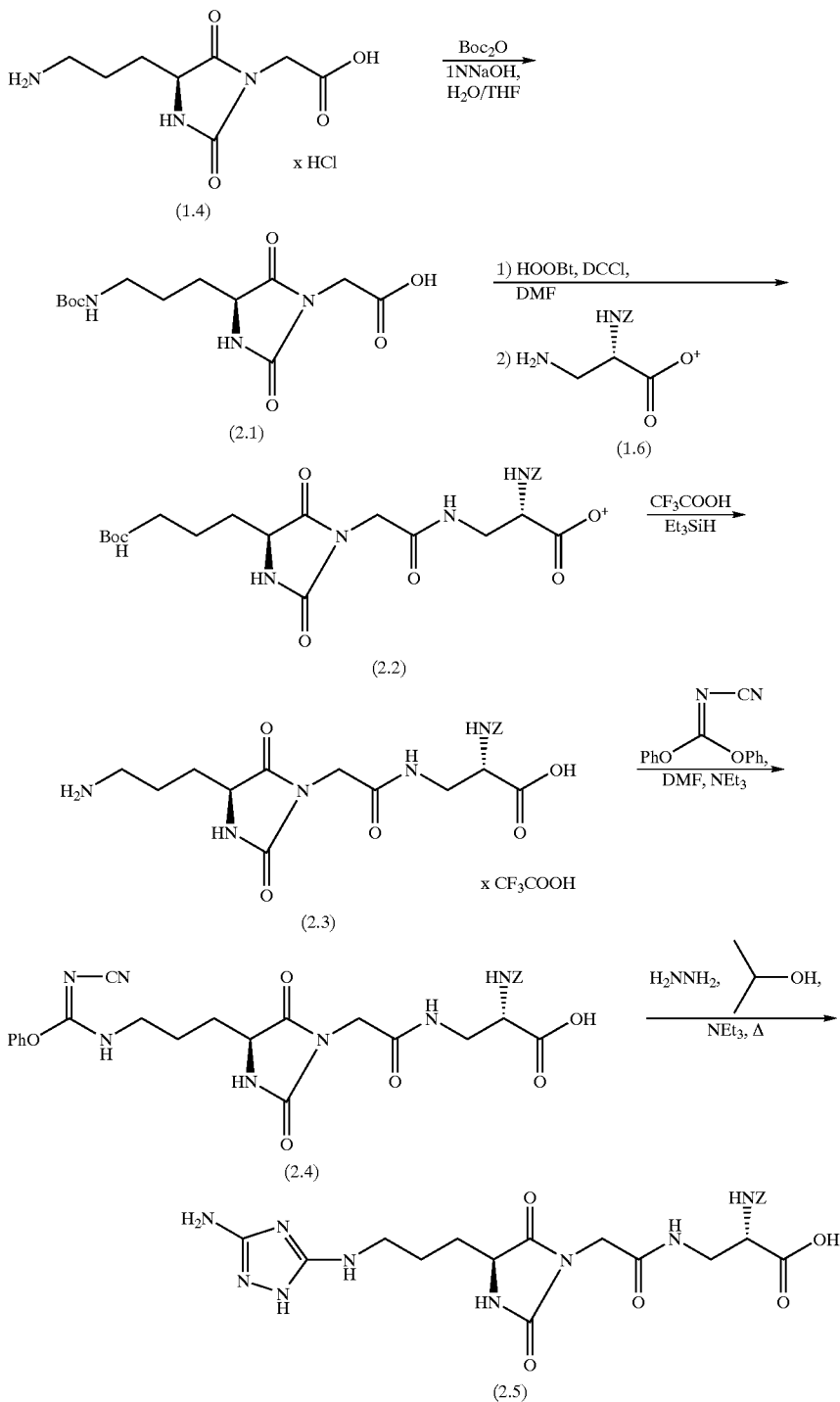

See Example 1 for the synthesis of (1.4) and (1.6).

2a) [(4S)-(3-tert-Butoxycarbonylaminopropyl)-2,5-dioxoimidazolidin-1-yl]acetic Acid (2.1)

6 g (23.84 mmol) of (1.4) are dissolved in 350 ml of THF/H$_2$O=2/1. The pH of the solution is adjusted, at 0° C., to 10.5 with 1N NaOH; 6.24 g (28.61 mmol) of di-tert-butyldicarbonate are added and the pH of the solution is maintained at between 9 and 10.5 by adding 1N NaOH. The solution is stirred at 0° C. for 1 h and left to stand at 4° C. overnight. The pH is adjusted to 4 with phosphate buffer and the solvent is removed in vacuo. The residue is triturated in methanol, and this mixture is filtered and the filtrate is concentrated. Following chromatography through silica gel using dichloromethane/MeOH/glacial acetic acid/water=7/3/0.3/0.3, 5.65 g (75%) are obtained of a viscous syrup of (2.1).

2b) tert-Butyl (2S)-benzyloxycarbonylamino-3-[2-((4S)-(3-tert-butoxycarbonylaminopropyl)-2,5-dioxoimidazolidin-1-yl)acetylamino]-propionate (2.2)

2.8 g (8.9 mmol) of (2.1) and 1.45 g (8.9 mmol) of HOOBt are dissolved in 50 ml of DMF, and 1.95 g (8.9 mmol) of DCCl are added at 0° C. After 1 h at 0° C. and 1 h at RT, 2.6 g (8.9 mmol) of (1.6) are added and the reaction mixture is stirred at RT for 2 h and then left to stand at RT overnight. Following filtration, the filtrate is concentrated and the residue is partitioned between H₂O and ethyl acetate; the organic phase is dried over Na₂SO₄, the solvent is removed in vacuo and the residue is chromatographed through silica gel using ethyl acetate/heptane 9/1to 6/4. 2.98 g (57%) of (2.2) are obtained.

2c) 3-[2-((4S)-(3-Aminopropyl)-2,5-dioxoimidazolidin-1-yl)acetylamino]-(2 S)-benzyloxycarbonylaminopropionic Acid (2.3)

2.9 g (4.9 mmol) of (2.2) are dissolved in a mixture composed of 20 ml of dichloromethane, 9.8 ml of trifluoroacetic acid and 2.35 ml of triethylsilane. After 3.5 h at RT, the mixture is concentrated and then freeze-dried. The residue is triturated in diethyl ether, dried, crystallized in a little methanol and triturated with ether. 1.34 g (50%) of (2.3) are obtained as a colorless solid.

2d) 3-[2-((4S)-4-(3-(Phenoxy-N-cyano-iminocarbonylamino)propyl)-2,5-dioxoimidazolidin-1-yl)acetylamino]-(2S)-benzyloxycarbonylamino-propionic Acid (2.4)

400 mg (0.73 mmol) of (2.3) are dissolved in 10 ml of DMF. 0.14 ml of triethylamine are added, followed by 190.7 mg (0.8 mmol) of diphenyl cyanocarbamate in 2 ml of DMF. After the mixture has been stirred at RT for 2 h, the solvent is removed in vacuo and the residue is dissolved in 50 ml of a 5% solution of acetic acid and this solution is freeze-dried. Following chromatography through silica gel using methanol, 260 mg (61%) of (2.4) are obtained.

2e) 3-[2-(4S)-(3-(5-Amino-2H-[1,2,4]triazol-3-ylamino)propyl)-2,5 dioxo-imidazolidin-1-yl)acetylamino]-(2S)-benzyloxycarbonylaminopropionic Acid (2.5)

260, mg (0.45 mmol) of (2.4) are suspended in 10 ml of isopropanol, and 62.4 μl (0.45 mmol) of triethylamine are then added. 28,5 μl (0.585 mmol) of hydrazine are added and the mixture is heated to reflux for 10 h. It is then left to stand at RT overnight, after which the precipitate is filtered off with suction and washed with butanol, THF and ether. After chromatography through ®Sephadex LH 20 using H₂O/n-butanol/HOAc=43/4.3/3.5 and subsequent freeze-drying, 80 mg (34%) of (2.5) are obtained as a colorless solid.

Example 3

(2S)-Benzyloxycarbonylamino-3-[((4S)-(guanidinoacylaminomethyl)-2,5-dioxoimidazolidin-1-yl)acetylamino]propionic Acid (3.11)

The synthesis was carried out in accordance with the following reaction sequence:

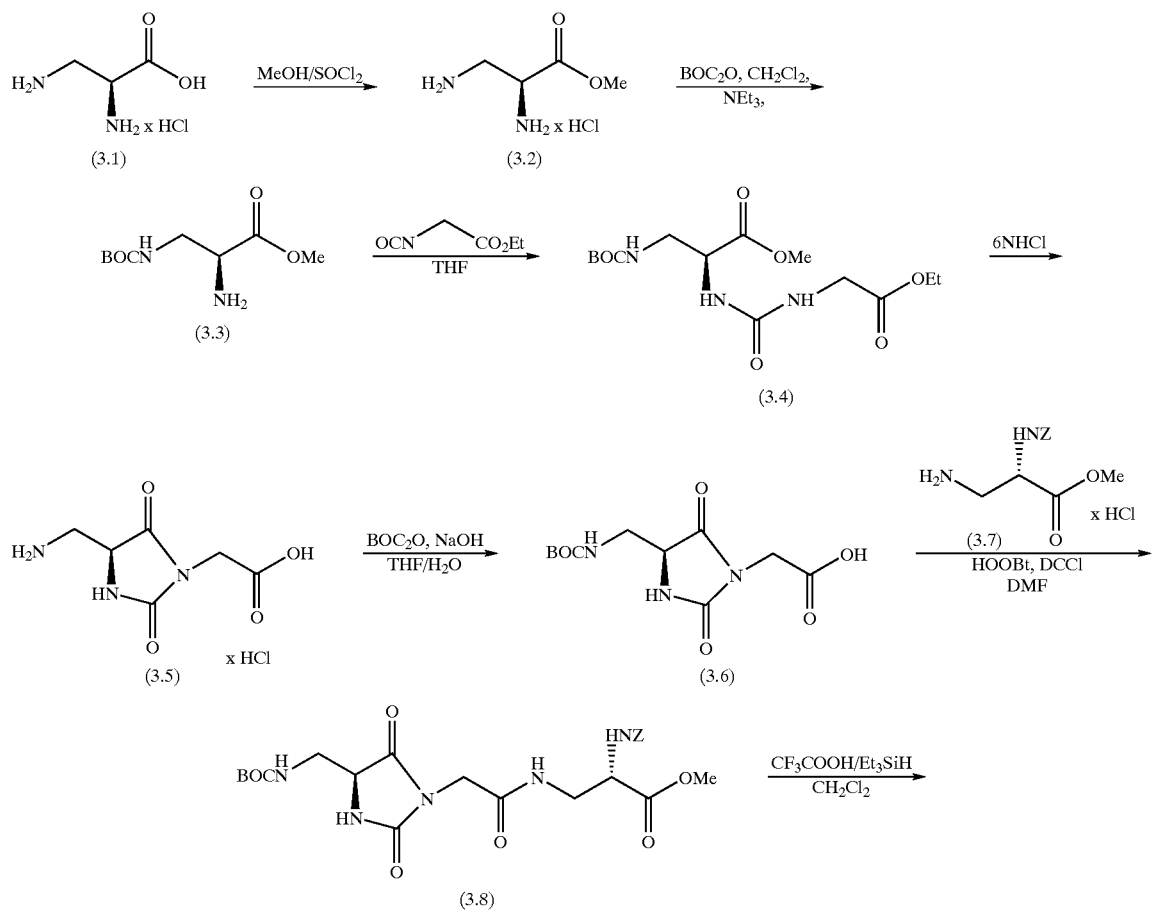

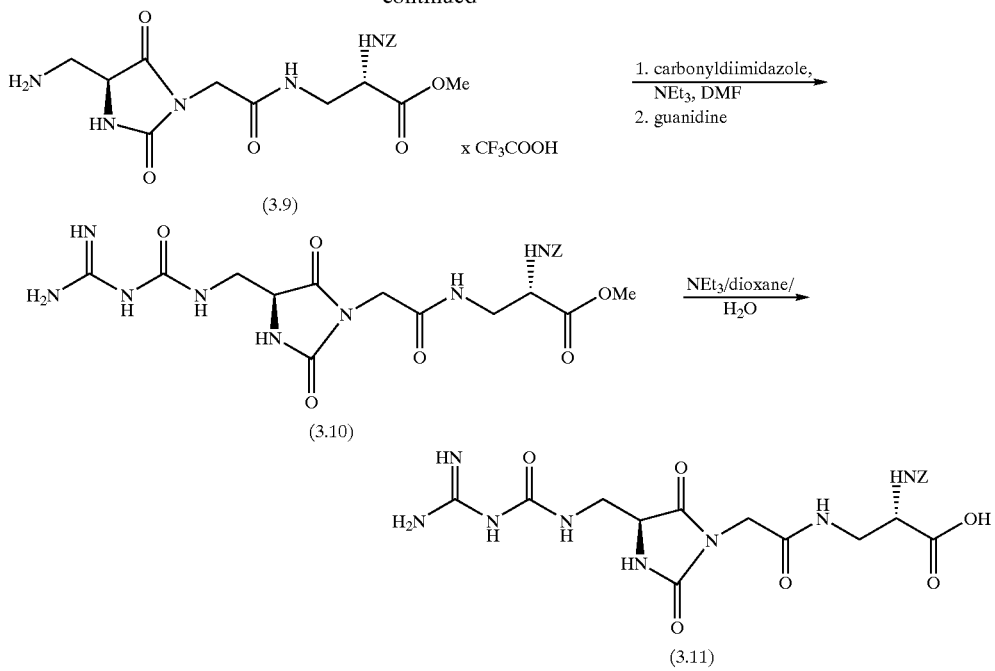

(3.9)

(3.10)

(3.11)

3a) Methyl (2S),3-diaminopropionate Dihydrochloride (3.2)

35 ml of thionyl chloride are added dropwise, at −15° C. and under an argon atmosphere, to 60 ml of abs. methanol, after which 25 g (240 mmol) of (2S),3-diaminopropionic acid hydrochloride (3.1) and a further 100 ml of methanol are added. After having been stirred at room temperature for 16 h, the mixture is heated under reflux for 4 h. The solution is poured into diisopropyl ether, the solvent is decanted off and the residue is chromatographed through silica gel using methanol. The product fractions are concentrated and the residue is triturated with diisopropyl ether. After filtering off the precipitate with suction and drying over paraffin, 26.3 g (57%) of (3.2) are obtained as a pale yellow solid.

3b) Methyl (2S)-amino-3-tert-butoxy-carbonylaminopropionate hydrochloride (3.3)

75.8 ml of triethylamine are added, at −78° C. to a suspension of 26 g (220 mmol) of (3.2) in 4.4 l of dichloromethane, after which a solution of 26.78 g (123 mmol) of di-tert-butyl dicarbonate in 220 ml of dichloromethane is added dropwise; the mixture is allowed to warm to 0° C. and is then stirred at this temperature for 1.5 h. The reaction mixture is concentrated and the residue is chromatographed through silica gel using ethyl acetate/methanol=20/1, 15.67 g (58%) of (3.3) are obtained as a pale yellow syrup.

3c) Methyl (2S)-ethyloxycarbonyl-methylaminocarbonylamino-3-tert-butoxycarbonylaminopropionate (3.4)

5.13 ml (45.8 mmol) of ethyl isocyanatoacetate are added dropwise to a suspension of 10 g (45.8 mmol) of the compound (3.3) in 100 ml of tetrahydrofuran and the mixture is left to stir at room temperature for 3 h; the solvent is removed in vacuo and the residue is chromatographed through silica gel using ethyl acetate/methanol=20/1. 13.44 g (85%) of (3.4) are obtained as a pale yellow oil.

3d) 2-[(4S)-(Aminomethyl)-2,5-dioxoimidazolidine] acetic acid hydrochloride (3.5)

13.2 g (34 mmol) of (3.4) are heated to reflux for 45 min together with 150 ml of 6N hydrochloric acid. The solution is concentrated and the residue is freeze-dried. After chromatography through silica gel using dichloromethane/methanol=7/3 and freeze-drying the product fractions, 6.4 g (84%) of (3.5) are obtained as a colorless solid.

3e) 2-[(4S)-(tert-Butoxycarbonylaminomethyl)-2,5-dioxoimidazolidine]-acetic Acid (3.6)

1N NaOH is added, at 0° C., to a solution of 4.4 g (19.7 mmol) of (3.5) in 300 ml of tetrahydrofuran/water=2/1 until a pH of 10.5 is reached (consumption: 26 ml); 5.16 g (23.6 mmol) of di-tert-butyl dicarbonate are added and the pH is kept at between 9.5 and 10.5 by adding 1N NaOH. After 1 h at 0° C. and 2 h at room temperature, the mixture is left to stand at 4° C. overnight; the pH is then adjusted to 7 with 1N HCl and subsequently to 4.1 with phosphate buffer. The solvent is removed in vacuo and the residue is triturated with methanol; this mixture is filtered and the filtrate is concentrated and the residue chromatographed through silica gel using dichloromethane/methanol/acetic acid/water=8/2/0.2/0.2. The product fractions are concentrated and freeze-dried. Yield of (3.6): 3.6 g (64%) of colorless solid.

3f) Methyl 3-amino-(2S)-benzyloxy-carbonylaminopropionate Hydrochloride (3.7)

7.4 ml (100.8 mmol) of thionyl chloride are added dropwise, at −15° C., to 50 ml of absolute methanol. 12 g (50.4 mmol) of 3-amino-(2S)-benzyloxycarbonylamino propionic acid hydrochloride are added, followed by 40 ml of absolute methanol. After stirring at −15° C. for 45 min and at room temperature for 20 h, the reaction mixture is poured into diisopropyl ether and the precipitate is filtered off with suction and dried under high vacuum. 14.18 g (98%) of (3.7) are obtained as a colorless solid.

3g) Methyl (2S)-benzyloxycarbonylamino-3-[((4S)-(tert-butoxycarbonyl-aminomethyl)-2,5-dioxoimidazolidin-1-yl)acetylamino]propionate (3.8)

848 mg (5.2 mmol) of HOOBt, and then 1.144 g (5.2 mmol) of DCCl, are added, at 0° C., to a solution of 1.5 g (5.2 mmol) of (3.6) in 20 ml of abs. DMF. After stirring at 0° C. for 1 h and at room temperature for 1 h, 1.5 g (5.2 mmol) of (3.7) and 0.67 ml of N-ethylmorpholine are added and the mixture is stirred at room temperature for 3 h. The precipitate is filtered off and the filtrate is concentrated; the residue is taken up in ethyl acetate and this solution is washed successively with a saturated solution of NaHCO$_3$, with a KHSO$_4$/K$_2$SO$_4$ solution and with water, and the organic phase is then dried over sodium sulfate. After filtration and after removing the solvent in vacuo, the residue is chromatographed through silica gel using ethyl acetate/heptane=6/4 to ethyl acetate, and 1.75 g (65%) of (3.8) are obtained.

3h) Methyl 3-[((4S)-(aminomethyl)-2,5-dioxoimidazolidin-1-yl)-acetylamino]-(2S)-benzyloxycarbonylaminopropionate trifluoroacetic Acid Salt (3.9)

1.7 g (3.26 mmol) of (3.8) are stirred, at room temperature for 4 h, in 6.7 ml of dichloromethane, 3.3 ml of trifluoroacetic acid and 0.78 ml of triethylsilane. The solution is poured into diethyl ether and the precipitate is filtered off. 1.54 g (88%) of (3.9) are obtained as a colorless solid.

3g) Methyl (2S)-benzyloxycarbonylamino-3-[((4S)-(guanidinoacylamino-methyl)-2,5-dioxoimidazolidin-1-yl)acetylamino]propionate (3.10)

0.129 ml of triethylamine is added to a solution of 500 mg (0.93 mmol) of (3.9) in 10 ml of absolute DMF, after which a solution of 152 mg (0.93 mmol) of carbonyldiimidazole in 10 ml of absolute DMF is added at 0° C. After stirring at room temperature for 4 h, 89 mg (1.86 mmol) of guanidine are added and the mixture is left to stir at room temperature for 2 h; the solvent is then removed in vacuo and the residue is chromatographed through silica gel using dichloromethane/methanol/acetic acid/water=8.5/1.5/0.15/0.15. After concentrating the product fractions and freeze-drying, 300 mg (64%) of (3.10) are obtained as a colorless solid.

3h) (2S)-Benzyloxycarbonylamino-3-[((4S)-(guanidinoacylaminomethyl)-2,5-dioxoimidazolidin-1-yl)acetylamino]propionic Acid (3.11)

180 mg (0.32 mmol) of (3.10) are dissolved in a mixture composed of dioxane/water/triethylamine=1/1/1. After 16 h at room temperature, the mixture is subjected to rotary evaporation, after which the residue is treated with water and freeze-dried. The residue from the freeze-drying is chromatographed through silica gel using dichloromethane/methanol/acetic acid/water=8/2/0.2/0.2. The product fractions are subjected to rotary evaporation and the residue is treated with water and freeze-dried; the residue from this freeze-drying is then triturated with ethyl acetate and diethyl ether. After filtering off with suction, 62 mg (39%) of (3.11) are obtained as a colorless solid.

ES(+)-MS: 493 (M+H)$^+$

Example 4

(2S)-Benzyloxycarbonylamino-3-[((4S)-(3-(2-pyrimidylamino)propyl)-2,5-dioxoimidazolidin-1-yl)acetylamino]propionic Acid (4.2)

The synthesis was carried out in accordance with the following reaction sequence:

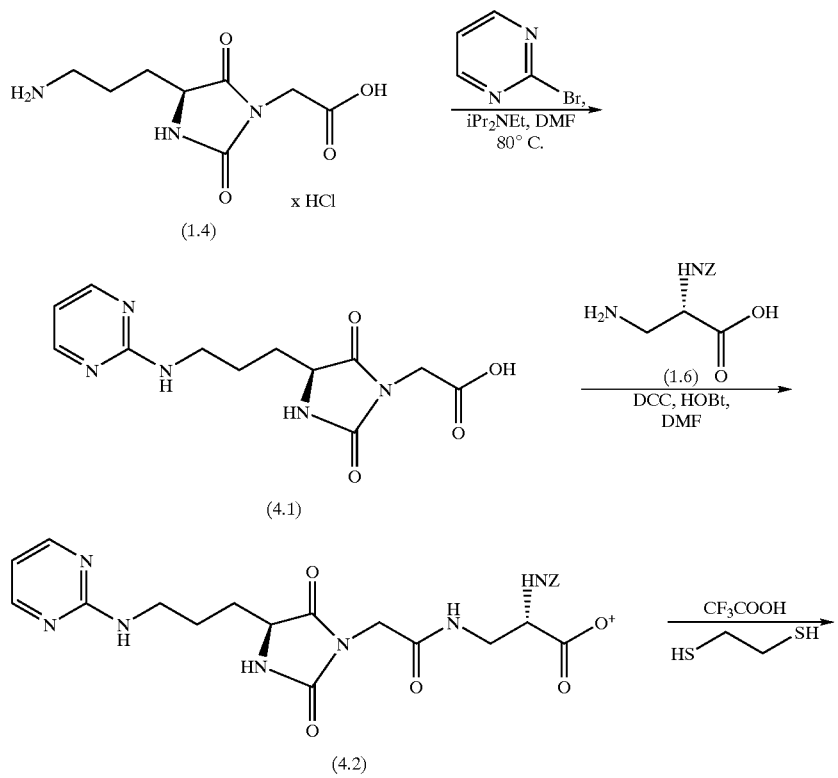

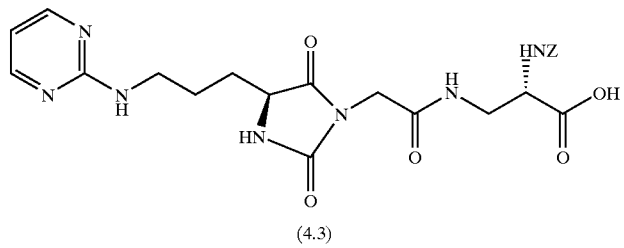

(4.3)

4a) 2-[(4S)-(3-(2-Pyrimidylamino)propyl)-2,5-dioxoimidazolidine]acetic Acid (4.1)

A mixture of 1 g (4 mmol) of (1.4), 632 mg (4 mmol) of 2-bromopyrimidine and 2.04 ml (12 mmol) of diisopropylethylamine (DIPEA) in 9 ml of DMF is heated at 80° C. for 26 h. The solvent is removed in vacuo and the residue is chromatographed through silica gel using dichloromethane/methanol/acetic acid/water=8/2/0.2/0.2. The product fractions are concentrated and 144 mg (12%) of (4.1) are obtained as a colorless solid.

4b) tert-Butyl (2S)-benzyloxycarbonylamino-3-[((4S)-(3-(2-pyrimidyl-amino)propyl)-2,5-dioxoimidazolidin-1-yl)acetylamino]propionate (4.2)

97 mg (0.44 mmol) of DCCl are added to a solution of 128 mg (0.44 mmol) of (4.1), 128 mg (0.44 mmol) of (1.6), 60 mg (0.44 mmol) of HOBt and 0.035 ml of N-ethylmorpholine in 5 ml of DMF. After 1 h at 0° C. and 16 h at room temperature, the solvent is removed in vacuo and the residue is chromatographed through silica gel using dichloromethane/methanol/acetic acid/water=9.5/0.5/0.05/0.05. 180 mg (72%) of (4.2) are obtained.

4c) (2S)-Benzyloxycarbonylamino-3-[((4S)-(3-(2-pyrimidylamino)propyl)-2,5-dioxoimidazolidin-1-yl)acetylamino]propionic Acid (4.3)

170 mg (0.3 mmol) of (4.2) are dissolved in a mixture composed of 2 ml of 90% trifluoroacetic acid and 0.2 ml of 1,2-dimercaptoethane. After 1 h at room temperature, the mixture is added to diethyl ether and the precipitate is centrifuged off, resuspended in diethyl ether and centrifuged once again. After dissolution in water and freeze-drying, the residue is chromatographed through Sephadex LH 20 using water/butanol/acetic acid=43/4.3/3.5. After freeze-drying, 76 mg (49%) of (4.3) are obtained as a colorless solid.

ES(+)-MS: 514 (M+H)$^+$

Example 5

(2S)-Benzyloxycarbonylamino-3-[((4S)-(3-(benzimidazolyl-2-amino)-propyl)-2,5-dioxoimidazolidin-1-yl)acetylamino]propionic Acid (5.5)

The synthesis was carried out in accordance with the following reaction sequence:

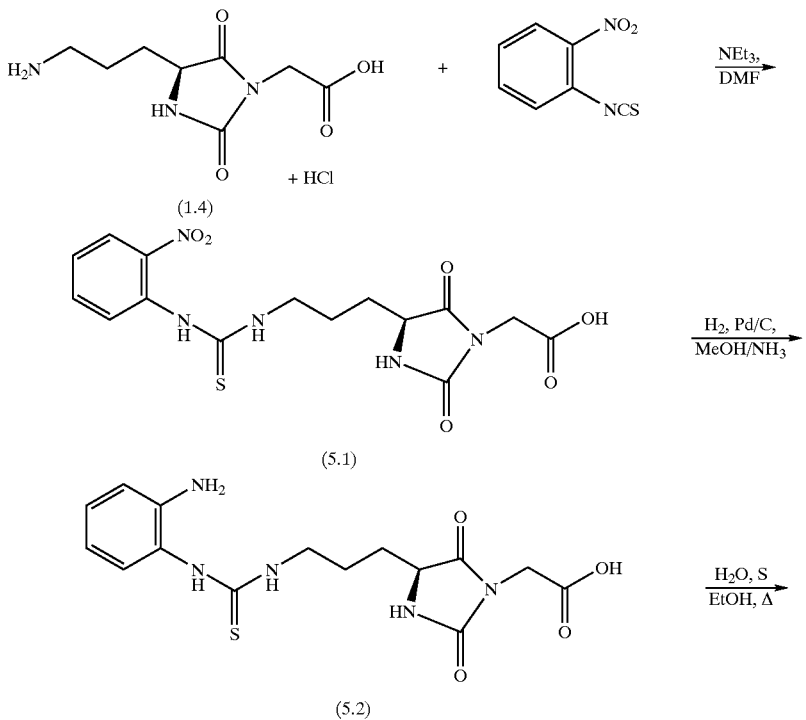

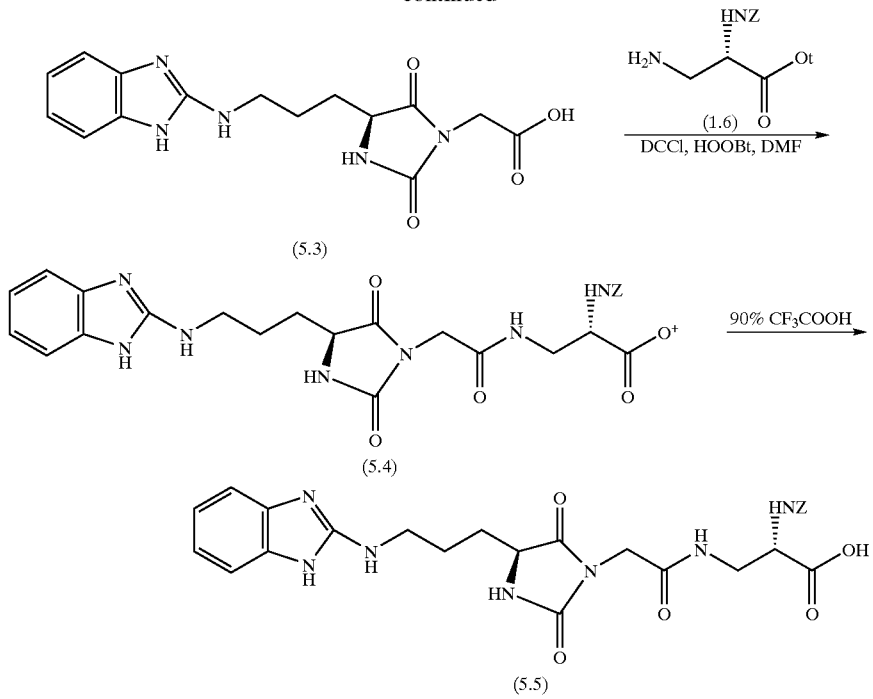

5a) 2-[(4S)-(3-(3-(2-Nitrophenyl)thioureido)propyl)-2,5-dioxo-imidazolidin-1-yl]acetic Acid (5.1)

4.96 ml (35.76 mmol) of triethylamine, and then 3.22 g (17.88 mmol) of 2-nitrophenyl isothiocyanate, are added, at 0° C., to a solution of 4.5 g (17.88 mmol) of (1.4) in 100 ml of DMF. After stirring at room temperature for 4 h, the solvent is removed in vacuo and the residue is partitioned between dichloromethane and 10% acetic acid. The aqueous phase is extracted twice with dichloromethane and the organic phase is dried over sodium sulfate. After filtration, the solvent is removed in vacuo and the residue is chromatographed through silica gel. The product fractions are concentrated and 3.16 g (45%) of (5.1) are obtained.

5b) 2-[(4S)-(3-(3-(2-Aminophenyl)thioureido)propyl)-2,5-dioxo-imidazolidin-1-yl]acetic Acid (5.2)

3.8 g of 10% Pd/C are added to 4.6 g (11.6 mmol) of (5.1) in 40 ml of absolute ethanol. 200 ml of ammonia-saturated ethanol are added and the mixture is hydrogenated at room temperature for 6 h. The catalyst is filtered off, the filtrate is concentrated and the residue (1.85 g) is used directly for synthesizing (5.3).

5c) 2-[((4S)-(3-(Benzimidazolyl-2-amino)propyl)-2,5-dioxoimidazolidin-1-yl]acetic Acid (5.3)

1.85 g of (5.3) in 35 ml of ethanol are heated under reflux for 16 h together with 3 g of mercuric oxide and 730 mg of sulfur. The mixture is filtered and the residue is decocted 5 times with water. The combined water phases are freeze-dried. 814 mg (21% based on (5.1)) of (5.3) are obtained as a colorless solid.

5d) tert-Butyl (2S)-benzyloxycarbonylamino-3-[((4S)-(3-(benzimidazolyl-2-amino)propyl)-2,5-dioxoimidazolidin-1-yl)acetylamino]propionate (5.4)

(5.4) is synthesized by reacting (5.3) with (1.6) as described in Example 4 in connection with the preparation of (4.2) from (4.1) and (1.6). Following chromatography of the crude product through silica gel using dichloromethane/methanol/acetic acid/water=9/1/0.1/0.1 and 8/2/0.2/0.2, and subsequently freeze-drying the product fractions, 255 mg (75%) of (5.4) are obtained, as a colorless solid, from 205 mg (0.56 mmol) of (5.3).

5e) (2S)-Benzyloxycarbonylamino-3-[((4S)-(3-(benzimidazolyl-2-amino)-propyl)-2,5-dioxoimidazolidin-1-yl)acetylamino]propionic acid (5.5)

250 mg (0.41 mmol) of the compound (5.4) are stirred at room temperature for 1 h in 3 ml of 90% trifluoroacetic acid. The trifluoroacetic acid is removed in vacuo and the residue is treated with water and freeze-dried. The residue from the freeze-drying is chromatographed through Sephadex LH 20 using water/butanol/acetic acid=43/4.3/3.5. After freeze-drying, 155 mg (66%) of (5.5) are obtained as a colorless solid.

ES(+)-MS: 552 (M+H)$^+$

Example 6

(2S)-Benzyloxycarbonylamino-3-[((4S)-(3-(cis-3a,4,5,6,7,7a-hexahydro-1H-benzimidazol-2-ylamino)propyl)-2,5-dioxoimidazolidin-1-yl)-acetylamino]propionic Acid (6.4)

The synthesis was carried out in accordance with the following reaction sequence:

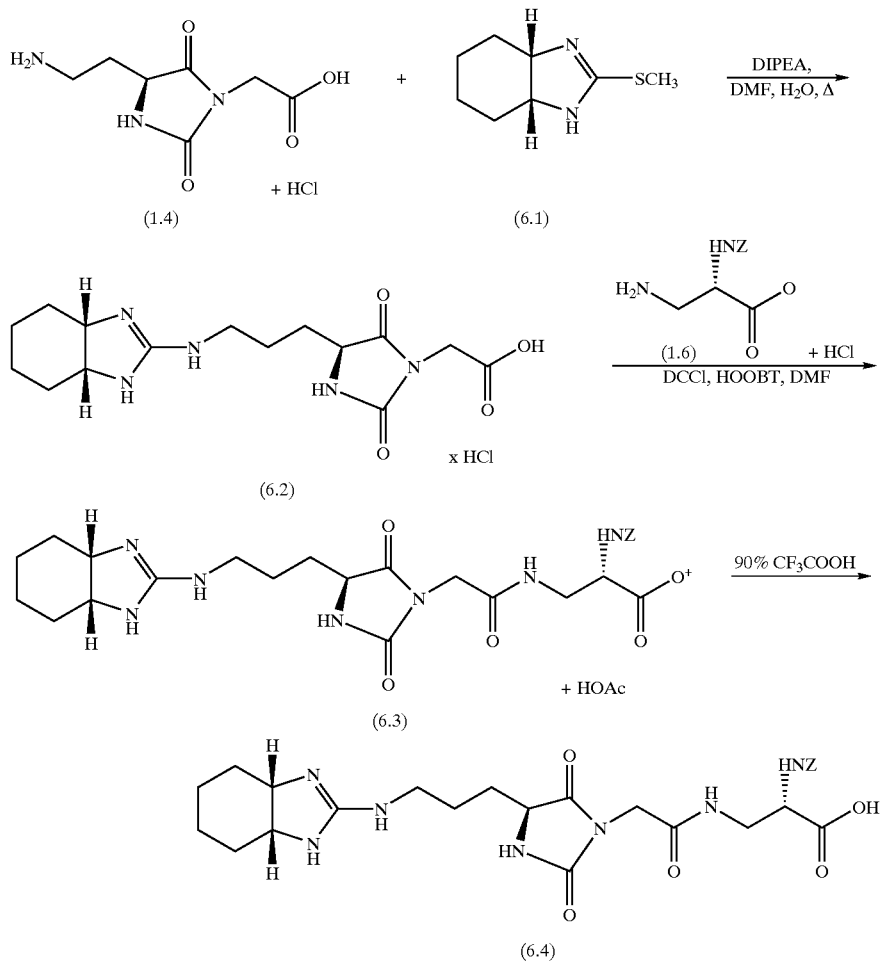

6a) [(4S)-(3-(cis-3a,4,5,6,7,7a-Hexahydro-1H-benzimidazol-2-ylamino)-propyl)-2,5-dioxoimidazolidin-1-yl]acetic Acid Hydrochloride (6.2)

0.51 ml of DIPEA and 6 drops of water are added to a solution of 298 mg (1 mmol) of (6.1) (prepared as described by G. D. Hartmann et al., WO 95/32710, p. 115) and 251 mg (1 mmol) of (1.4) in 6 ml of DMF, and the mixture is stirred at 100° C. for 24 h. The solvent is removed in vacuo and the residue is chromatographed through silica gel using dichloromethane/methanol/acetic acid/water=9/1/0.1/0. 1, after which the combined product fractions are chromatographed through Sephadex LH 20 using water/butanol/acetic acid=43/4.3/3.5. The product fractions are combined and freeze-dried. Following transformation into the hydrochloride, 130 mg (35%) of (6.2) are obtained as a colorless solid.

6b) tert-Butyl (2S)-benzyloxycarbonylamino-3-[((4S)-(3-(cis-3a,4,5,6,7,7a-hexahydro-1H-benzimidazol-2-ylamino)propyl)-2,5-dioxoimidazolidin-1-yl)acetylamino]propionate Acetic Acid Salt (6.3)

(6.3) is synthesized by reacting (6.2) with (1.6) as described in Example 4 in connection with the preparation of (4.2) from (4.1) and (1.6). After chromatographing the crude product through silica gel using dichloromethane/methanol/acetic acid/water=8/2/0.2/0.2 and then 9/1/0.1/0.1, and subsequently freeze-drying the product fractions, 45 mg (19%) of (6.3) are obtained, as a colorless solid, from 130 mg (0.35 mmol) of (6.2).

6c) (2S)-Benzyloxycarbonylamino-3-[((4S)-(3-(cis-3a,4,5,6,7,7a-hexahydro-1H-benzimidazol-2-ylamino)propyl)-2,5-dioxo-imidazolidin-1-yl)acetylamino]-propionic Acid (6.4)

40 mg (0.168 mmol) of (6.4) are stirred at room temperature for 1 h in 1 ml of 90% trifluoroacetic acid. After removing the trifluoroacetic acid in vacuo and purifying the crude product by means of preparative HPLC through RP18, and subsequently freeze-drying the product fractions, 13 mg (14%) of (6.4) are obtained as a colorless solid.

ES(+)-MS: 558 (M+H)$^+$

Example 7

(2S)-Benzyloxycarbonylamino-3-[2-((4S)-(N'-(4,5-dihydro-1H-imidazol-2-yl)-hydrazinocarbonylmethyl]-2,5-dioxoimidazolidin-1-yl)acetylamino]propionic Acid (7.8)

The synthesis was carried out in accordance with the following reaction sequence:

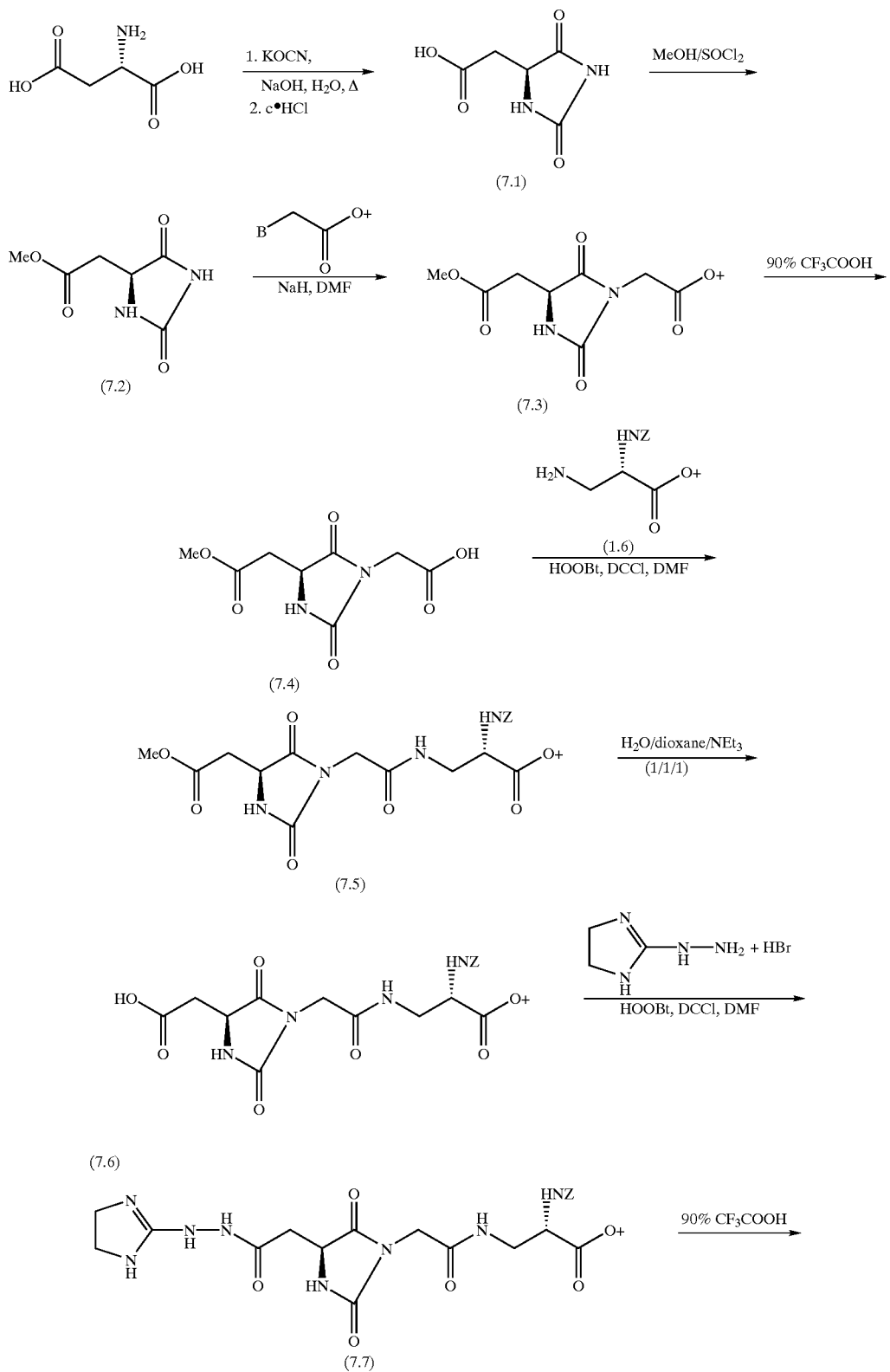

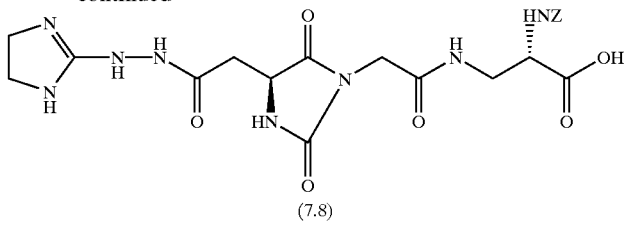

(7.8)

7a) (4S)-Carboxymethyl-2,5-dioxoimidazolidine (7.1)

5.5 ml of 11.7N sodium hydroxide solution and 7.5 g (92.5 mmol) of potassium cyanate are added, at 80° C. and while stirring, to a suspension of 10 g (75 mmol) of L-aspartic acid in water. During the course of 1 h, the pH is in each case adjusted to 7 by adding conc. HCl in portions at 85° C. (consumption: 1.5 ml). The pH of the reaction mixture is subsequently adjusted to 3.5 with 5.5 ml of conc. HCl. A further 9.5 ml of conc. HCl are added and the reaction solution is stirred at 85° C. for 2 h and then left to stand at room temperature for 18 h. The precipitate is filtered off with suction, washed with a little ice-cold water and dried over $P_2O_5$. 8.49 g (72%) of (7.1) are obtained as a colorless solid.

7b) (4S)-Methoxycarbonylmethyl-2,5-dioxoimidazolidine (7.2)

7.9 ml (107 mmol) of thionyl chloride and 8.47 g (53.5 mmol) of (7.1) are added, at −15° C., to 70 ml of methanol and the reaction mixture is stirred at room temperature for 24 h. The solution is then poured into diethyl ether and the precipitate is filtered off with suction and washed with diethyl ether. After drying under high vacuum, 5.12 g (56%) of (7.2) are obtained as a colorless solid. Concentrating the ether phase and triturating the residue with diethyl ether yield a further 2.79 g (30%) of (7.2) after drying under high vacuum.

7c) tert-Butyl [(4S)-methoxycarbonylmethyl-2,5-dioxoimidazolidine]-acetate (7.3)

4 g (23.2 mmol) of (7.2) are added, while cooling with ice and under an argon atmosphere, to a suspension of 1.02 g (23.2 mmol) of sodium hydride (55% strength in oil) in 20 ml of absolute DMF. After the hydrogen evolution has come to an end, 4.53 g (23.2 mmol) of tert-butyl bromoacetate are added. After stirring at 0° C. for 1 h, 2 h at room temperature and standing overnight, the solvent is removed and the residue is chromatographed through silica gel using dichloromethane/methanol=40/1. The product fractions are concentrated and the residue is triturated with diethyl ether. 4.21 g (63%) of (7.3) are obtained.

7d) [(4S)-Methoxycarbonylmethyl-2,5-dioxoimidazolidine]acetic Acid (7.4)

4.2 g (14.67 mmol) of (7.3) are dissolved in 50 ml of 90% trifluoroacetic acid. After stirring at room temperature for 1 h, the trifluoroacetic acid is removed in vacuo and the residue is freeze-dried. 3.17 g (94%) of (7.4) are obtained.

7e) tert-Butyl (2S)-benzyloxycarbonylamino-3-[((4S)-methoxycarbonylmethyl-2,5-dioxoimidazolidin-1-yl)acetylamino]propionate (7.5)

(7.5) is synthesized by reacting (7.4) with (1.6) as described in Example 4 in connection with the preparation of (4.2) from (4.1) and (1.6). 1.72 g (79%) of (7.5) are obtained from 1 g (4.3 mmol) of (7.4) after chromatographing the crude product through silica gel using dichloromethane/methanol=20/1, and then 40/1, and after concentrating the product fractions.

7f) tert-Butyl (2S)-benzyloxycarbonylamino-3-[((4S)-carboxymethyl-2,5-dioxoimidazolidin-1-yl)acetylamino]propionate (7.6)

A solution of 700 mg (1.38 mmol) of (7.5) in water/dioxane/triethylamine=1/1/1 is stirred at 50° C. for 6 h. After standing at room temperature overnight, the reaction mixture is concentrated and the residue is chromatographed through silica gel using dichloromethane/methanol/acetic acid/water=9/1/0.1/0.1. 364 mg (54%) of (7.6) are obtained after concentrating the product fractions.

7g) tert-Butyl (2S)-benzyloxycarbonylamino-3-[2-((4S)-(N'-(4,5-dihydro-1H-imidazol-2-yl)hydrazinocarbonylmethyl]-2,5-dioxoimidazolidin-1-yl)acetylamino]propionate(7.7)

44.7 mg of DCCl are added, at 0° C., to a solution of 100 mg (0.2 mmol) of (7.6) and 33.1 mg (0.2 mmol) of HOOBt in 5 ml of DMF. After 1 h at 0° C. and 1 h at room temperature, 36.8 mg (0.2 mmol) of 2-hydrazino-2-imidazole hydrobromide are added and the mixture is left to stir at room temperature for 3 days. The solvent is removed in vacuo and the residue is chromatographed through silica gel using dichloromethane/methanol/acetic acid/water=8/2/0.2/0.2. The product fractions are concentrated and freeze-dried. 60 mg (52%) of (7.7) are obtained.

7h) (2S)-Benzyloxycarbonylamino-3-[2-((4S)-(N'-(4,5-dihydro-1H-imidazol-2-yl)hydrazinocarbonylmethyl]-2,5-dioxoimidazolidin-1-yl)acetylamino]propionic Acid (7.8)

55 mg (0.096 mmol) of (7.7) are stirred at room temperature for 1 h in 1 ml of 90% trifluoroacetic acid. 10.6 mg (21%) of (7.8) are obtained as a colorless solid after removing the trifluoroacetic acid in vacuo and purifying the crude product by means of preparative HPLC through RP18 and subsequently freeze-drying the product fractions.

ES(+)-MS: 519 (M+H)$^+$

Example 8

(2S)-Benzyloxycarbonylamino-3-[2-(2,5-dioxo-(4S)-(N'-(1,4,5,6-tetrahydro-pyrimidin-2-yl)hydrazinocarbonylmethyl)imidazolidin-1-yl)acetylamino]propionic Acid (8.2)

The synthesis was carried out in accordance with the following reaction sequence:

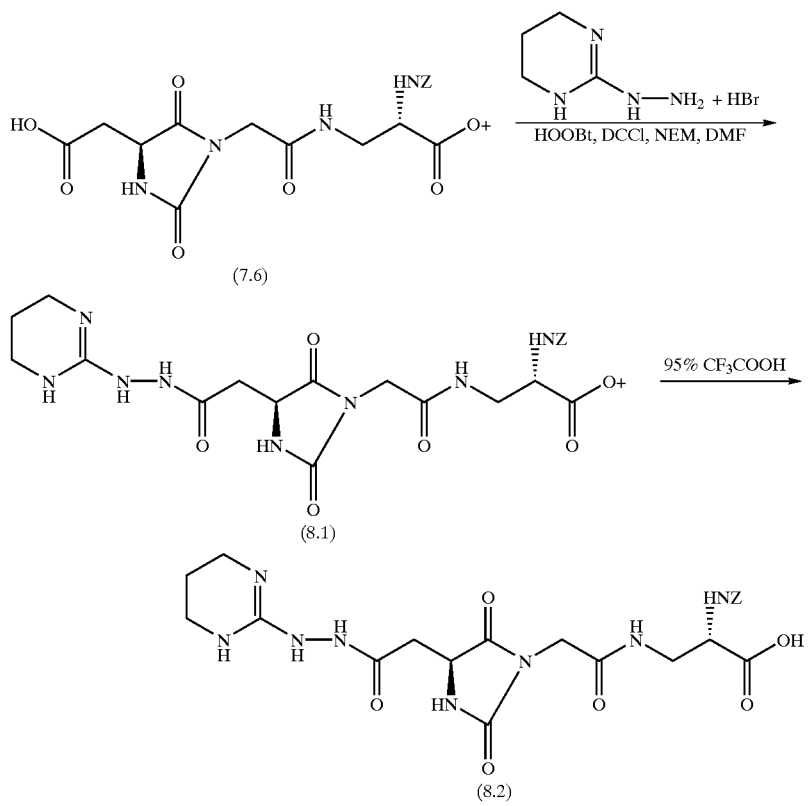

(7.6)

(8.1)

(8.2)

8a) tert-Butyl (2S)-benzyloxycarbonylamino-3-[2-(2,5-dioxo-(4S)-(N'-(1,4,5,6-tetrahydropyrimidin-2-yl)hydrazinocarbonylmethyl)imidazolidin-1-yl)acetylamino]propionate (8.1)

55 mg of DCCl are added, at 0° C., to a solution of 130 mg (0.26 mmol) of (7.6) and 43 mg (0.26 mmol) of HOOBt in 5 ml of DMF and the mixture is left to stir at 0° C. for 1 h and at room temperature for 1 h; 0.034 ml of N-ethylmorpholine (NEM) and 52 mg (0.26 mmol) of 2-hydrazino-1,4,5,6-tetrahydropyrimidine hydrobromide are then added. After stirring at room temperature for 28 h, the solvent is removed in vacuo and the residue is chromatographed through silica gel using dichloromethane/methanol/acetic acid/water=8.5/1.5/0.15/0.15. The product fractions are concentrated and freeze-dried. 80 mg (52%) of (8.1) are obtained.

8b) (2S)-Benzyloxycarbonylamino-3-[2-(2,5-dioxo-(4S)-(N'-(1,4,5,6-tetrahydropyrimidin-2-yl)hydrazinocarbonylmethyl)imidazolidin-1-yl)-acetylamino]propionic Acid (8.2)

A solution of 80 mg (0.136 mmol) of (8.1) in 4 ml of 90% trifluoroacetic acid is stirred at room temperature for 1 h and concentrated in vacuo; the residue is then chromatographed through Sephadex LH 20 using water/butanol/acetic acid= 43/4.3/3.5. The product fractions are concentrated and purified by preparative HPLC through RP18. 41.9 mg (59%) of (8.2) are obtained as a colorless solid after concentrating the product fractions and freeze-drying.

ES(+)-MS: 533 (M+H)$^+$

Example 9

2-Benzyloxycarbonylamino-3-[2-((4S)-(2-(N'-(4,5-dihydro-1H-imidazol-2-yl)-hydrazinocarbonyl)ethyl)-2,5-dioxoimidazolidin-1-yl)acetylamino]propionic acid (9.1)

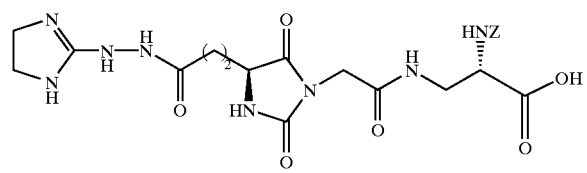

(9.1)

(9.1) is synthesized as described in Example 7, starting from L-glutamic acid.

ES(+)-MS: 533 (M+H)$^+$

Example 10

3-[(2-((4S)-(8(1H-Benzimidazol-2-ylmethyl)carbamoyl)methyl)-2,5dioxoimidazolidin-1-yl)acetylamino]-(2S)-benzyloxycarbonylaminopropionic Acid (10.2)

The synthesis was carried out in accordance with the following reaction sequence:

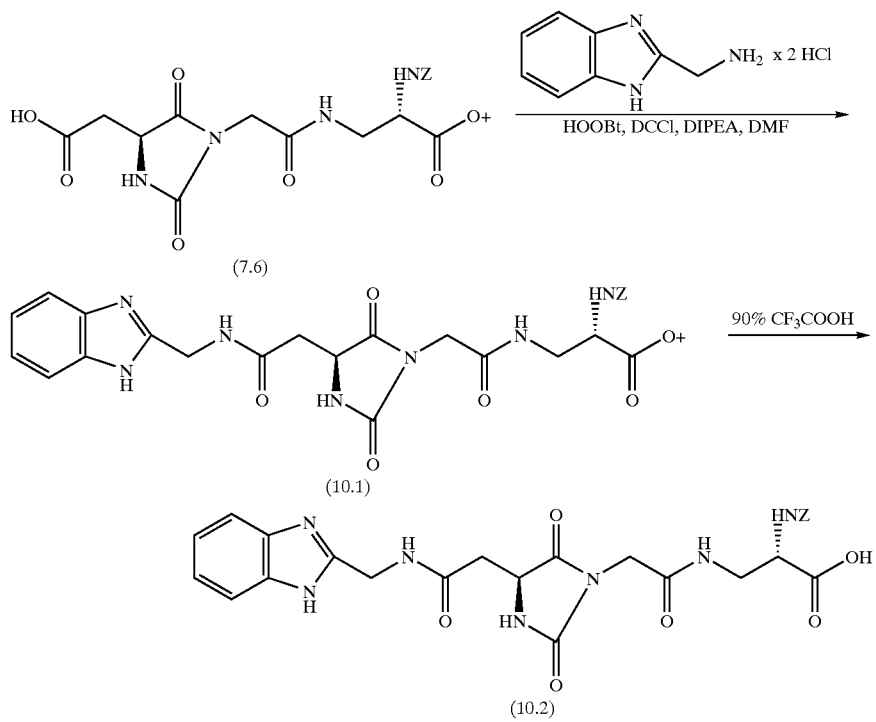

10a) tert-Butyl 3-[(2-((4S)-(8(1H-benzimidazol-2-ylmethyl)carbamoyl)methyl)-2,5-dioxoimidazolidin-1-yl)acetylamino]-(2S)-benzyloxycarbonylaminopropionate (10.1)

192 mg of DCCl are added, at 0° C., to a solution of 430 mg (0.87 mmol) of (7.6) and 142.5 mg (0.87 mmol) of HOOBT in 10 ml of DMF. After stirring at 0° C. for 1 h and at room temperature for 1 h, 231 mg (1.04 mmol) of 2-(aminomethyl)benzimidazole and 0.5 ml of diisopropyl-ethylamine (DIPEA) are added and the mixture is stirred at room temperature for a further 2 h. After standing overnight, the solvent is removed in vacuo and the residue is chromatographed through silica gel using dichloromethane/methanol/acetic acid/water=9.5/0.5/0.05/0.05. 390 mg (72%) of (10.1) are obtained after concentrating the product fractions.

10b) 3-[(2-((4S)-(8(1H-Benzimidazol-2-ylmethyl)carbamoyl)methyl)-2,5-dioxo-imidazolidin-1-yl)acetylamino]-(2S)-benzyloxycarbonylamino-propionic Acid (10.2)

360 mg (0.579 mmol) of (10.1) are dissolved in 10 ml of 95% trifluoroacetic acid. After 30 min at room temperature, the solution is concentrated in vacuo and the residue is partitioned between ethyl acetate and water; the water phase is extracted with ethyl acetate and freeze-dried. The residue is chromatographed through Sephadex LH 20 using water/butanol/acetic acid=43/4.3/3.5. The product fractions are concentrated and freeze-dried. 135 mg (40%) of (10.2) are obtained as a colorless solid.

ES(+)-MS: 566 (M+H)$^+$

Example 11

(2S)-Benzyloxycarbonylamino-3-[2-((4S)-(3-(3H-imidazo[4,5-b]pyridin-2-ylamino)propyl)-2,5-dioxoimidazolidin-1-yl)acetylamino]propionic Acid (11.7)

The synthesis was carried out in accordance with the following reaction sequence:

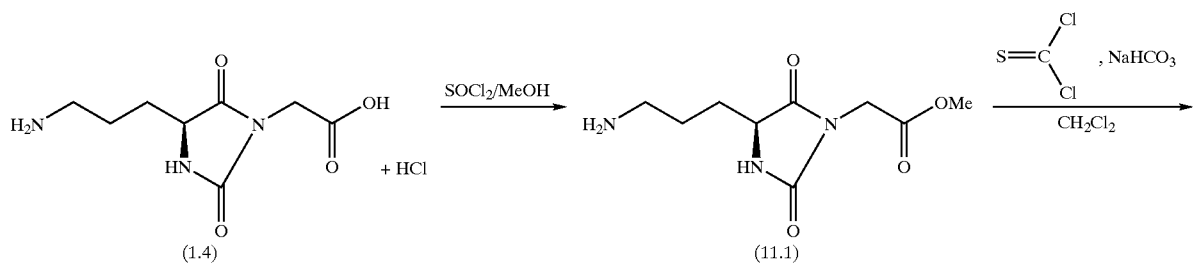

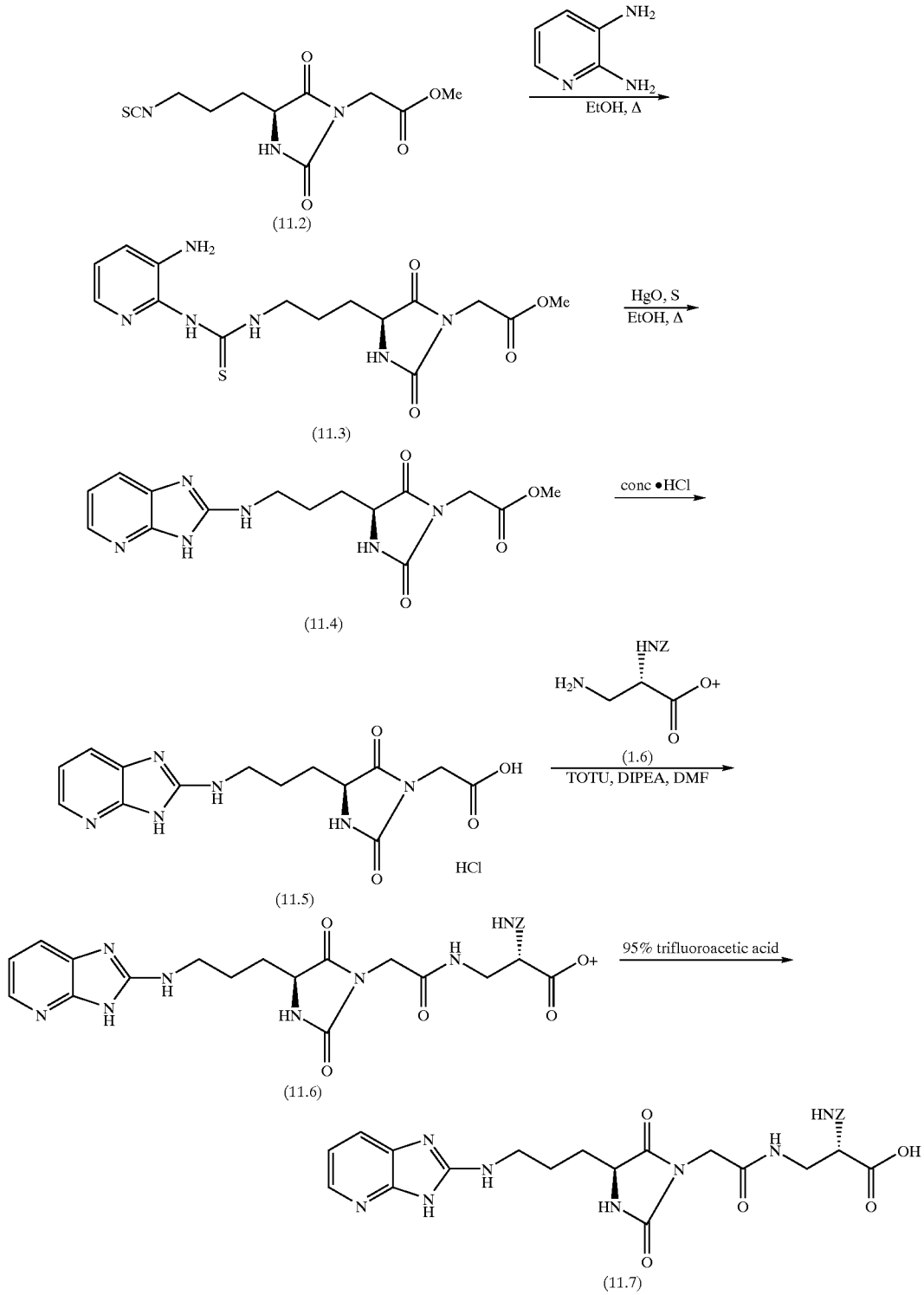

11a) Methyl [4-(3-aminopropyl)-2,5-dioxoimidazolidin-1-yl]acetate Hydrochloride (11.1)

12.5 ml (107 mmol) of thionyl chloride and 21.5 g (85.4 mmol) of (1.4) are added, at −15° C., to 100 ml of methanol and the reaction mixture is stirred at room temperature for 24 h. The solution is then poured into diethyl ether and the precipitate is filtered off with suction and washed with diethyl ether. After drying under high vacuum, 20.52 g (90%) of (11.1) are obtained as a colorless solid.

11b) Methyl [4-(3-isothiocyanatopropyl)-2,5-dioxoimidazolidin-1-yl]acetate (11.2)

100 ml of a saturated solution of sodium hydrogen carbonate are added to a suspension of 2.65 g (10 mmol) of (11.1) in 30 ml of dichloromethane. After stirring for 10 min while cooling with ice, 1.53 ml (20 mmol) of thiophosgene are added to the methylene chloride phase. The mixture is stirred for 10 min, while cooling with ice, the phases are separated and the water phase is extracted twice with dichloromethane. The combined organic phases are dried over sodium sulfate. 2.04 g (75%) of (11.2) are obtained after filtering and removing the solvent in vacuo.

11c) Methyl [(4S)-(3-(3-(3-aminopyridin-2-yl)thioureido)propyl)-2,5-dioxo-imidazolidin-1-yl]acetate (11.3)

A solution of 1.66 g (6.11 mmol) of (11.2) and 667 mg (6.11 mmol) of 2,3-diaminopyridine in 18 ml of absolute ethanol is stirred at room temperature for 16 h and then under reflux for 2 h. The solvent is removed in vacuo and the residue is chromatographed through silica gel using dichloromethane/methanol/acetic acid/water=9/1/0.1/0.1. 1.67 g (72%) of (11.3) are obtained after concentrating the product fractions and freeze-drying.

11d) Methyl [(4S)-(3-(3H-imidazo[4,5]pyridin-2-ylamino)propyl)-2,5-dioxo-imidazolidin-1-yl]acetate (11.4)

1.62 g (7.51 mmol) of mercuric oxide and 24 mg of sulfur are added to a solution of 1.43 g (3.75 mmol) of (11.3) in 80 ml of ethanol and the mixture is heated under reflux for 1 h. 1.15 g (89%) of (11.4) are obtained after filtering and concentrating the filtrate in vacuo.

11e) [(4S)-(3-(3H-imidazo[4,5-b]pyridin-2-ylamino)propyl)-2,5-dioxo-imidazolidin-1-yl]acetic Acid Hydrochloride (11.5)

286 mg (0.83 mmol) of (11.4) are stirred at 50° C. for 5 h in 10 ml of conc. HCl. After filtering, the filtrate is diluted with water and freeze-dried. 277 mg (91%) of (11.5) are obtained as a colorless solid.

11f) tert-Butyl (2S)-benzyloxycarbonylamino-3-[2-((4S)-(3-(3H-imidazo-[4,5-b]-pyridin-2-ylamino)propyl)-2,5-dioxoimidazolidin-1-yl)acetylamino]propionate (11.6)

237 mg (0.72 mmol) of O-[cyano(ethoxycarbonyl)methylenamino]-1,1,3,3-tetramethyluronium tetrafluoroborate (TOTU) and 0.245 ml of diisopropylethylamine (DIPEA) are added to a solution of 267 mg (0.72 mmol) of (11.5) and 213 mg (0.72 mmol) of (1.6) in 10 ml of DMF and the mixture is stirred at room temperature for 1 h. The solvent is removed in vacuo and the residue is dissolved in ethyl acetate; the ethyl acetate phase is then extracted twice with a saturated solution of $NaHCO_3$ and twice with water. The organic phase is dried over sodium sulfate. 425 mg (97%) of (11.6) are obtained after filtering and concentrating the filtrate in vacuo.

11g) (2S)-Benzyloxycarbonylamino-3-[2-((4S)-(3-(3H-imidazo[4,5-b]pyridin-2-ylamino)propyl)-2,5-dioxoimidazolidin-1-yl)acetylamino]propionic acid (11.7)

420 mg (0.69 mmol) of (11.6) are dissolved in 10 ml of 95% trifluoroacetic acid. After 15 min at room temperature, the solution is concentrated in vacuo and the residue is chromatographed through Sephadex LH 20 using water/butanol/acetic acid=43/4.3/3.5. The product fractions are concentrated and freeze-dried. 234 mg (62%) of (11.7) are obtained as a colorless solid.

ES(+)-MS: 553 (M+H)$^+$

Example 12

(2S)-Benzyloxycarbonylamino-3-[2-(4S)-(3-(3H-imidazo[4,5-c]pyridin-2-ylamino)propyl)-2,5-dioxoimidazolidin-1-yl)acetylamino]propionic Acid (12.3)

The synthesis was carried out in accordance with the following reaction sequence:

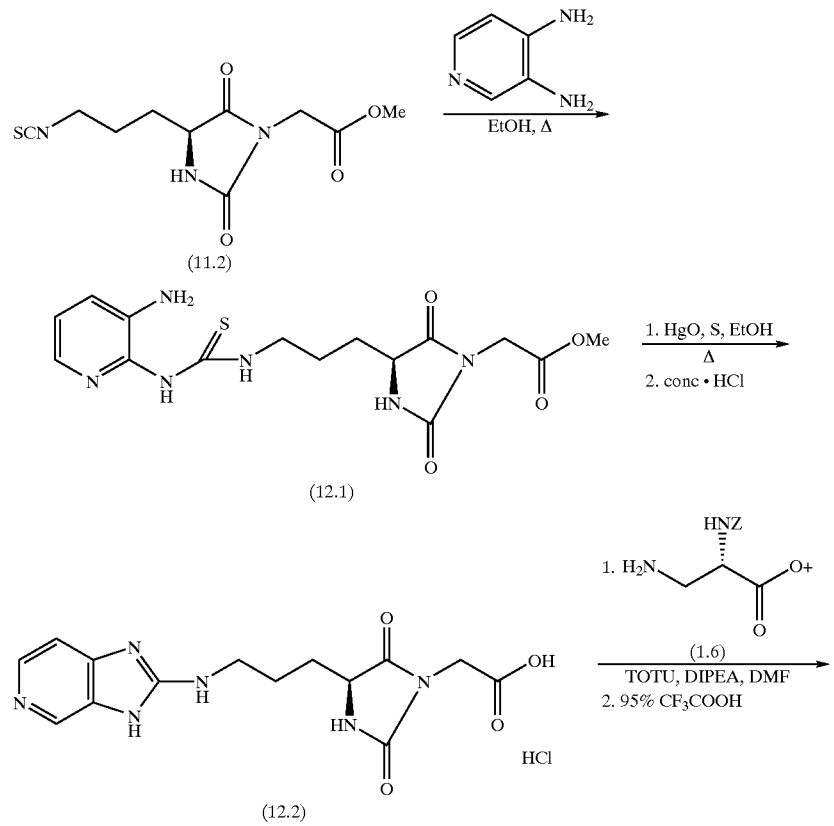

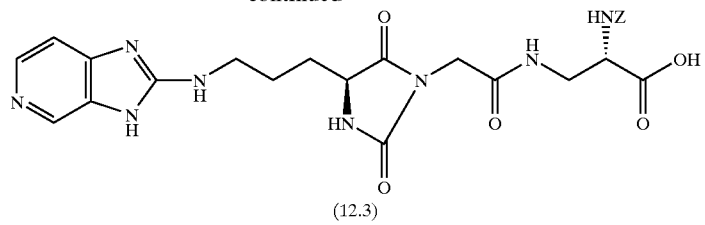

(12.3)

The starting point for synthesizing (12.3) is (11.2), which, in analogy with the preparation of (11.3), is reacted with 3,4diaminopyridine to form (12.1). The latter is then, in analogy with the preparation of (11.4) and (11.5), cyclized with mercuric oxide and reacted with conc. HCl to form (12.2). (12.2) is reacted with (1.6), as described in connection with the preparation of (11.6), and the resulting coupling product is converted into (12.3) while cleaving the tert-butyl ester as described in connection with the synthesis of (11.7) from (11.6).

ES(+)-MS: 553 (M+H)$^+$

Example 13

(2S)-(Adamant-1-ylmethoxycarbonylamino)-3-[((4S)-(3-(benzimidazolyl-2-amino)propyl)-5-oxo-2-thioxoimidazolidin-1-yl)acetylamino]propionic Acid (13.7)

The synthesis was carried out in accordance with the following reaction sequence:

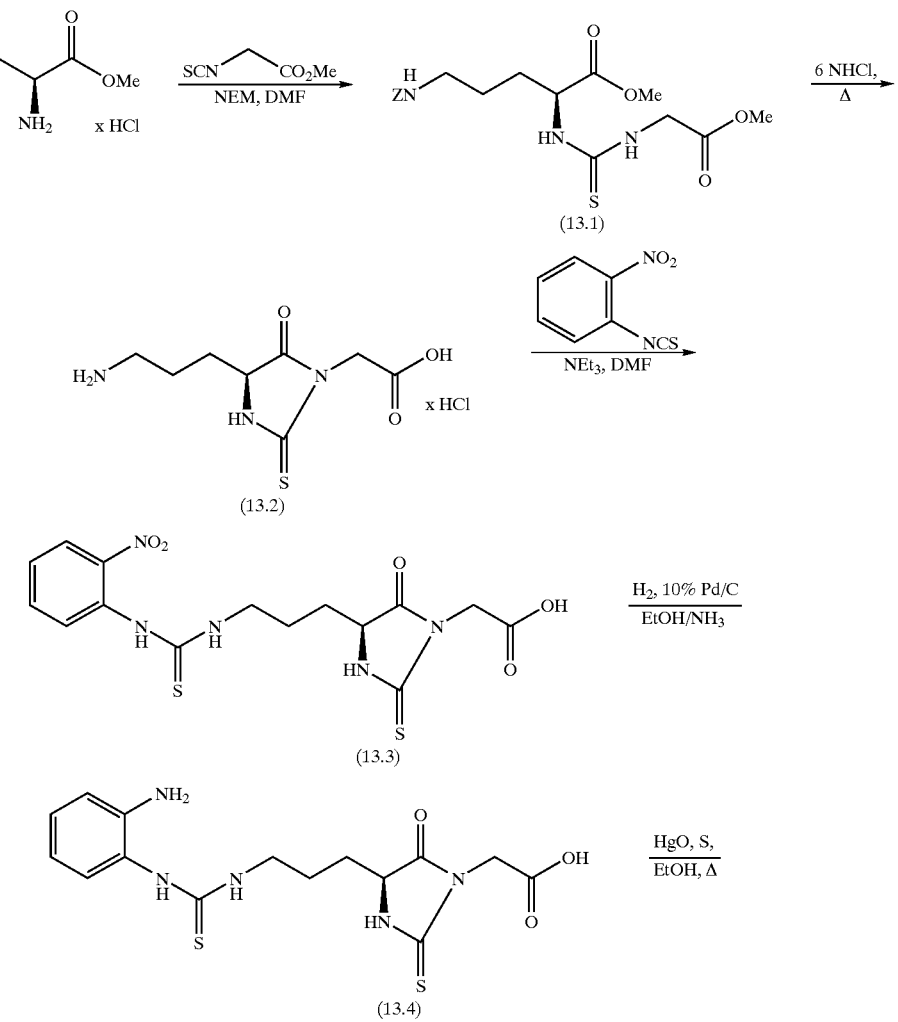

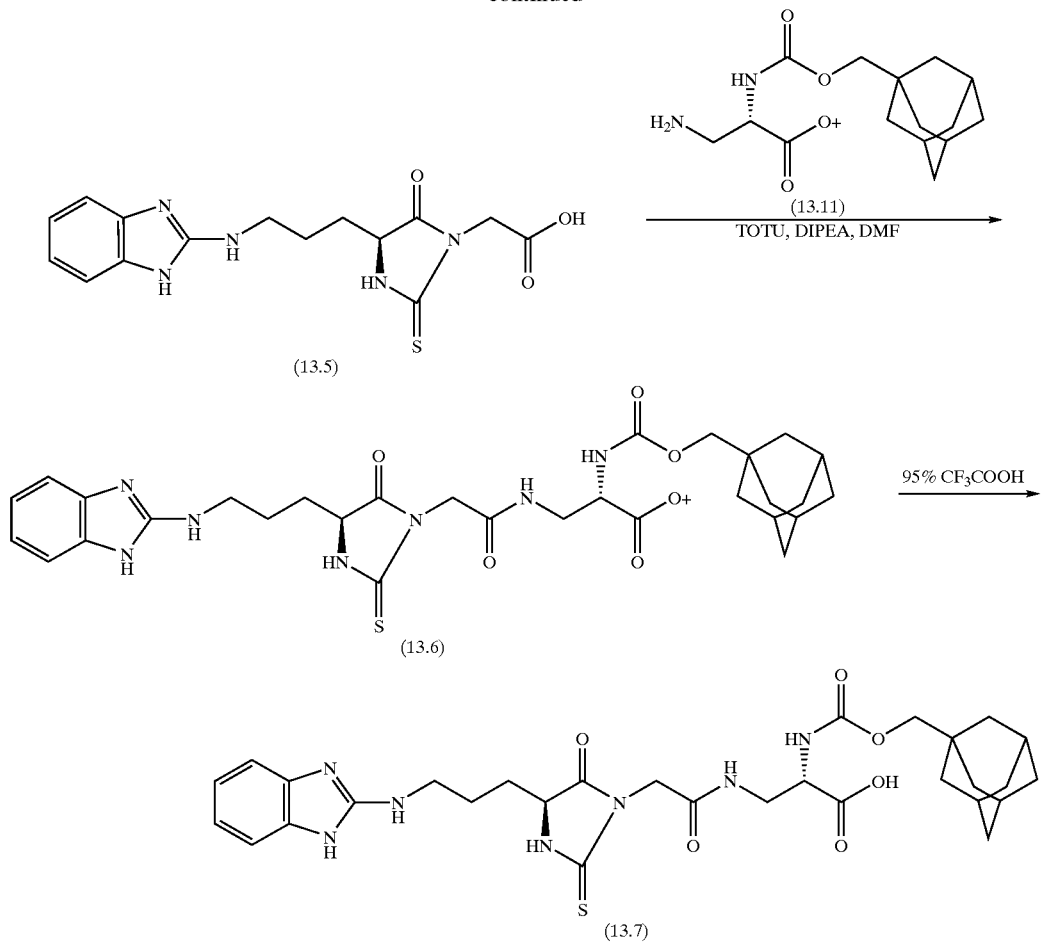

13a) Methyl 5-benzyloxycarbonylamino-(2S)-methoxycarbonylmethylamino-thiocarbonylamino-5-pentanoate (13.1)

2.62 g (20 mmol) of methyl isothiocyanatoacetate and 2.3 g (20 mmol) of N-ethylmorpholine (NEM) are added, at 0° C., to a solution of 6.32 g (20 mmol) of H-Orn(Z)-OMe×HCl (Bachem) in 40 ml of DMF. After stirring at room temperature for 20 h, the solvent is removed in vacuo and the residue is taken up in dichloromethane; the dichloromethane solution is then extracted twice with water.

After drying the organic phase over sodium sulfate, filtering and removing the solvent in vacuo, (13.1) is obtained and used directly for synthesizing (13.2).

13b) [((4S)-(3-Aminopropyl))-5-oxo-2-thioxoimidazolidin-1-yl]acetic Acid Hydrochloride (13.2)

A suspension of (13.1) in 150 ml of 6N HCl is stirred at 50° C. for 5 h. The solution is concentrated and the residue is thoroughly stirred twice with diethyl ether. After drying the residue under high vacuum and then over KOH, (13.2) is obtained and used directly for synthesizing (13.3).

13c) 2-[(4S)-(3-(3-(2-Nitrophenyl)thioureido)propyl)-5-oxo-2-thioxo-imidazolidin-1-yl]acetic Acid (13.3)

2.77 ml (20 mmol) of triethylamine are added dropwise, while cooling with ice, to a solution of (13.2) and 3.6 g (20 mmol) of 2-nitrophenyl isothiocyanate in 50 ml of DMF. The solution is left to stir at room temperature overnight, after which a further 360 mg (2 mmol) of 2-nitrophenyl isothiocyanate and 0.8 ml of triethylamine are added and the mixture is left to stir at room temperature for a further 5 h. The solvent is removed in vacuo and the residue is dissolved in ethyl acetate; the ethyl acetate phase is then washed twice with an aqueous solution of $KHSO_4/K_2SO_4$ and dried over sodium sulfate. After filtering, the ethyl acetate is removed in vacuo and the residue is chromatographed through silica gel using dichloromethane/methanol/acetic acid/water=9/1/0.1/0.1.

4.06 g (49%, based on (13.1)) of (13.3) are obtained after concentrating the product fractions.

13d) 2-[(4S)-(3-(3-(2-Aminophenyl)thioureido)propyl)-5-oxo-2-thioxo-imidazolidin-1-yl]acetic Acid (13.4)

611 mg (1.48 mmol) of (13.4) in 50 ml of a saturated, ethanolic solution of ammonia are hydrogenated at room temperature for 3 h over 600 mg of 10% Pd/C. 488 mg (87%) of (13.4) are obtained after filtering and concentrating the filtrate in vacuo.

13e) [(4S)-(3-(Benzimidazolyl-2-amino)propyl)-5-oxo-2-thioxoimidazolidin-1-yl]acetic Acid (13.5)

550 mg (2.54 mmol) of mercuric oxide and 8.1 mg of sulfur are added to a solution of 485 mg (1.27 mmol) of (13.4) in 50 ml of ethanol and the mixture is heated under reflux for 3 h. After filtering and removing the solvent in vacuo the residue is taken up in 10% acetic acid and this solution is freeze-dried. 307 mg (79%) of (13.5) are obtained as a colorless solid.

13f) tert-Butyl (2S)-(adamant-1-ylmethoxy-carbonylamino)-3-[((4S)-(3-(benzimidazolyl-2- amino)propyl)-5-oxo-2-thioxoimidazolidin-1-yl)-acetylamino]propionate (13.6)

273 mg (0.834 mmol) of TOTU and 0.28 ml of diisopropylethylamine (DIPEA) in absolute DMF are added to a solution of 290 mg (0.834 mmol) of (13.5) and 297 mg (0.834 mmol) of (13.11) (synthesis, see 13h-k). The mixture is left to stir at room temperature for 2.5 h. The solvent is removed in vacuo and the residue is taken up in ethyl acetate; the ethyl acetate phase is then extracted twice with a saturated solution of sodium hydrogen carbonate and water. After drying over sodium sulfate, the ethyl acetate is removed in vacuo and the residue is chromatographed through silica gel using dichloromethane/methanol/acetic acid/water=9.5/0.5/0.05/0.05. 46.3 mg (8%) of (13.6) are obtained after concentrating the product fractions.

13g) (2S)-Adamant-1-ylmethoxycarbonylamino)-3-[((4S)-(3-(benzimidazolyl-2-amino)propyl)-5-oxo-2-thioxoimidazolidin-1-yl)-acetylamino]propionic Acid (13.7)

38.1 mg (0.056 mmol) of (13.6) are dissolved in 2 ml of 95% trifluoroacetic acid. After 10 min at room temperature, the solution is concentrated in vacuo and the residue is purified by means of preparative HPLC (RP18). 11 mg (32%) of (13.7) are obtained after freeze-drying the product fractions.

FAB-MS: 626 (M+H)+

Synthesis of tert-butyl 3-amino-(2S)-(adamant-1-ylmethoxycarbonylamino)propionate (13.11)

The synthesis was carried out in accordance with the following reaction sequence:

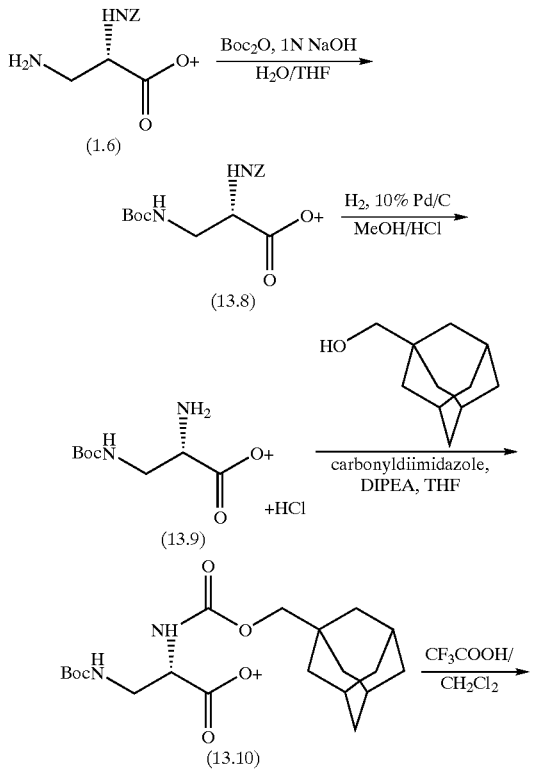

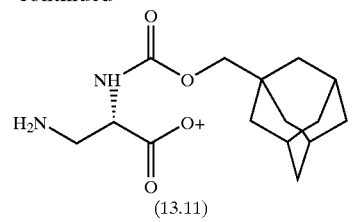

13h) tert-Butyl (2S)-benzyloxycarbonylamino-3-tert-butoxycarbonylaminopropionate (13.8)

8.9 g (40.8 mmol) of di-tert-butyl dicarbonate are added, at 0° C., to a solution of 10 g (34 mmol) of (1.6) in 600 ml of tetrahydrofuran/water=211, after which 1 N NaOH is added in portions so that the pH of the solution is between 9 and 10 (consumption of 1N NaOH: 32 ml). After stirring at room temperature for 3 h, 1 l of water is added and the mixture is extracted 3 times with diethyl ether. After drying over sodium sulfate, filtering and removing the solvent in vacuo, the residue is chromatographed through silica gel using dichloromethane/methanol=20/1. 13.19 g (98%) of (13.8) are obtained.

13i) tert-Butyl (2S)-amino-3-tert-butoxy-carbonylaminopropionate Hydrochloride (13.9)

13.1 g (33.2 mmol) of (13.8) are hydrogenated in methanol/HCl over 10% Pd/C. After 1.5 h, the mixture is filtered and the filtrate is concentrated in vacuo; 9.77 g (99%) of (13.9) are obtained as a colorless solid.

13j) tert-Butyl (2S)-(adamant-1-ylmethoxy-carbonylamino)-3-tert-butoxycarbonylaminopropionate (13.10)

A solution of 10.9 g (65.4 mmol) of (1-hydroxymethyl) adamantane and 10.6 g (65.4 mmol) of carbonyldiimidazole in 60 ml of THF is stirred at 50° C. for 1.5 h. 9.7 g (32.7 mmol) of (13.9) in 25 ml of THF and 5.6 ml (32.7 mmol) of diisopropylethylamine (DIPEA) are added and the mixture is stirred at 60° C. for 4 h and then left to stand at room temperature overnight. The solvent is removed in vacuo and the residue is chromatographed through silica gel using heptane/ethyl acetate=7/3. 8.7 g (59%) of (13.10) are obtained as a colorless oil.

13k) tert-Butyl (2S)-(adamant-1-ylmethoxy-carbonylamino)-3-aminopropionate (13.11)

A solution of 8.7 g (19.22 mmol) of (13.10) in 180 ml of trifluoroacetic acid dichloromethane=1/1 is added, after 1 min, to 1.5 ml of an ice-cold solution of NaHCO₃. The solution is extracted 3 times with dichloromethane and the dichloromethane phase is then dried over sodium sulfate. 6.35 g (94%) of (13.11) are obtained as a colorless solid after filtering and removing the solvent in vacuo.

Example 14

3-[2-((4R,S)-(3-(1H-Benzimidazol-2-ylamino)propyl)-methyl-2,5-dioxo-imidazolidin-1-yl)acetylamino]-(2S)-benzyloxycarbonylaminopropionic Acid (14.8)

The synthesis was carried out in accordance with the following reaction sequence:

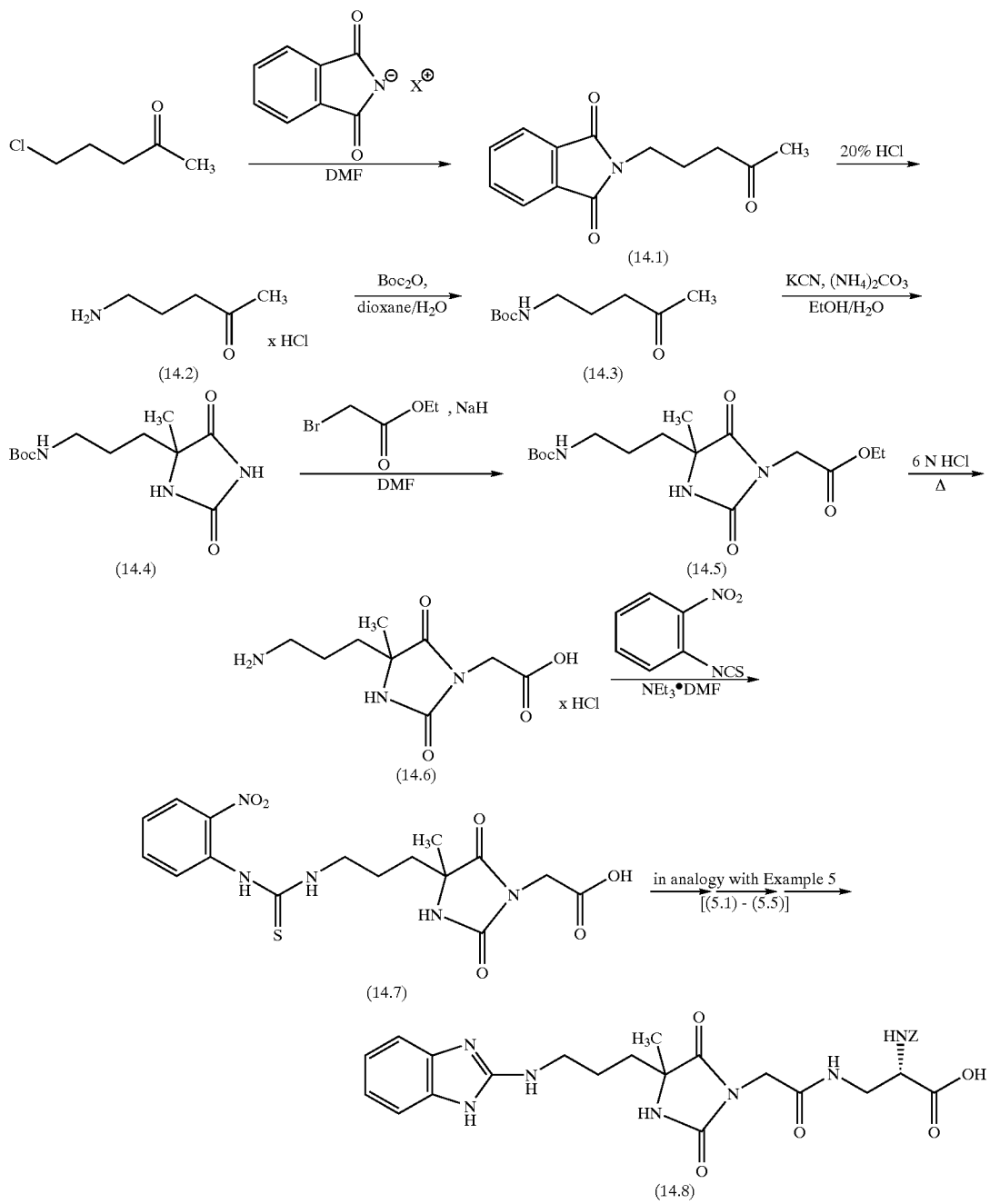

14a) 2-(4-Oxopentyl)isoindole-1,3-dione (14.1)

24.59 g (132.8 mmol) of potassium phthalimide are added to a solution of 14.3 ml (124.4 mmol) of 5-chloro-2-pentanone in 100 ml of DMF and the mixture is left to stir at room temperature for 3 h and at 60° C. for 30 h. After filtering, the filtrate is partitioned between water and dichloromethane. The phases are separated and the organic phase is washed successively with water, twice with an 0.2N solution of NaOH and water and then dried over sodium sulfate. After filtering, the solvent is removed in vacuo and the residue is chromatographed through silica gel using heptane/ethyl acetate=6/4. 9.8 g (34%) of (14.1) are obtained after concentrating the product fractions.

14b) 5-Amino-2-oxopentane Hydrochloride (14.2)

13 g (56.2 mmol) of (14.1) are dissolved in 335 ml of 20% hydrochloric acid and the solution is heated at reflux for 6 h. After standing at room temperature overnight, the mixture is filtered and the filtrate is concentrated in vacuo. A pale yellow oil of crude (14.2) is obtained, with this oil being used directly for synthesizing (14.3).

14c) 5-tert-Butoxycarbonylamino-2-oxopentane (14.3)

(14.2) (from 14b) is dissolved in 110 ml of dioxane and 55 ml of water and the solution is adjusted to a pH of 8.5 by adding 65 ml of 1N NaOH. 13.25 g (60.8 mmol) of di-tert-butyl dicarbonate are added at 0° C. and the pH of the solution is adjusted to 8.5 by repeatedly adding 1N NaOH. After stirring at room temperature for 4.5 h, dioxane is removed in vacuo and the pH of the remaining solution is adjusted to 2–3 by adding $KHSO_4/K_2SO_4$ solution; the solution is then extracted 3 times with ethyl acetate. The combined organic phases are washed with a saturated solution of sodium hydrogen carbonate and then dried over sodium sulfate. 11.1 g (99% starting from (14.1)) of (14.3) are obtained after filtering and removing the solvent in vacuo.

(14d) (4R,S)-(3-tert-Butoxycarbonylamino)propyl-4-methyl-2,5-dioxo-imidazolidine (14.4)

41.96 g (439.2 mmol) of ammonium carbonate and 4.2 g (65.1 mmol) of potassium cyanide are added to a solution of 10.06 g (50 mmol) of (14.3) in 130 ml of ethanol/water=1/1 and the mixture is heated to 55–65° C. After 5.5 h at this temperature, the pH of the reaction mixture is adjusted to 6.3 with 100 ml of 6N HCl and the mixture is then stirred for a further 2 h. The mixture is then left to stand at room temperature overnight, after which the solvent is removed in vacuo and the residue is partitioned between water and ethyl acetate. The phases are separated and the water phase is extracted twice with ethyl acetate. The combined organic phases are dried over sodium sulfate, after which the drying agent is filtered off and the solvent is removed in vacuo. 12.42 g (92%) of (14.4) are obtained as colorless crystals.

14e) Ethyl [(4R,S)-(3-tert-butoxycarbonylaminopropyl)-4-methyl-2,5-dioxo-imidazolidin-1-yl]acetate (14.5)

388 mg (16.1 mmol) of sodium hydride are added, while cooling with ice and under an argon atmosphere, to a solution of 4 g (14.7 mmol) of (14.3) in 100 ml of DMF and the mixture is stirred at room temperature for 45 min. 1.63 ml (14.7 mmol) of ethyl bromoacetate are added and the mixture is left to stir at room temperature for 3 h; the solvent is then removed in vacuo. The residue is dissolved in ethyl acetate and the ethyl acetate phase is washed twice with water. After drying over sodium sulfate and removing the solvent in vacuo, 4.98 g (95%) of (14.5) are obtained as a pale yellow oil.

14f) [(4R,S)-(3-Aminopropyl)-4-methyl-2,5-dioxoimidazolidin-1-yl]acetic Acid Hydrochloride (14.6)

4.98 g (13.9 mmol) of (14.5) are suspended in 50 ml of 6N HCl and the suspension is heated under reflux for 1 h. The reaction mixture is concentrated in vacuo and the residue is dissolved in water and freeze-dried. (14.6) is obtained as a crude product and is used directly for synthesizing (14.7).

The synthesis of (14.7), starting from (14.6), and of (14.8), starting from (14.7), is effected in analogy with the synthesis of (5.5) starting from (1.4) (see Example 5).

(14.8): ES(+)-MS: 566 $(M+H)^+$

Example 15

(2S)-Benzyloxycarbonylamino-3-[((4S)-(3-(6-methoxy-1H-benzimidazol-2-ylamino)propyl)-2,5-dioxoimidazolidin-1-yl)acetylamino]propionic Acid (15.3)

The synthesis was carried out in accordance with the following reaction sequence:

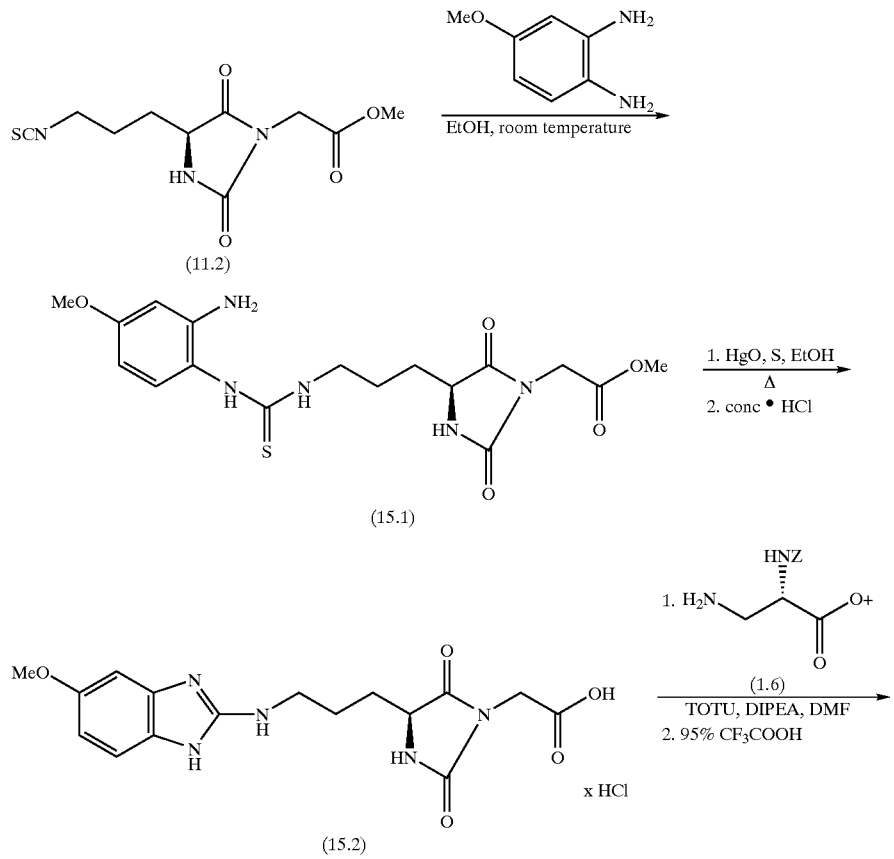

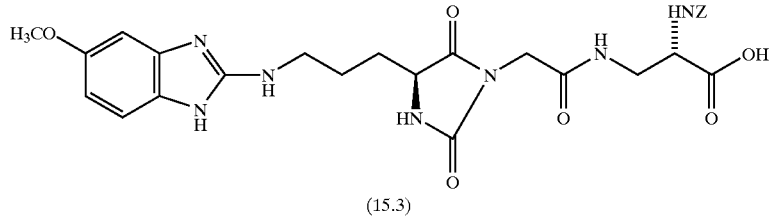

(15.3)

The starting-point for synthesizing (15.3) is (11.2), which, in analogy with the preparation of (11.3), is reacted with 4-methoxyorthophenylenediamine at room temperature to form (15.1). The latter is then, in analogy with the preparation of (11.4) and (11.5), cyclized with mercuric oxide and reacted with conc. HCl to form (15.2). (15.2) is then reacted with (1.6), as described in connection with the preparation of (11.6), and the resulting coupling product is converted into (15.3) with cleavage of the tert-butyl ester, as described in connection with the synthesis of (11.7) from (11.6).

ES(+)-MS: 582 (M+H)$^+$

Example 16

(2S)-Benzyloxycarbonylamino-3-[((4S)-(3-(5,6methoxy-1H-benzimidazol-2-ylamino)propyl)-2,5-dioxoimidazolidin-1-yl)acetylamino]propionic Acid (16.1)

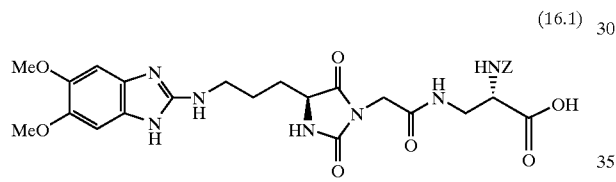

(16.1)

(16.1) is synthesized, as described in connection with the preparation of (15.3), by using 1,2dimethoxy-4,5-diaminobenzene, which is prepared from 1,2-dimethoxy-4,5-dinitrobenzene by hydrogenation over 10% Pd/C in methanol, instead of using 1-methoxy-3,4-diaminobenzene.

ES(+)-MS: 612 (M+H)$^+$

Example 17

(2S)-Benzyloxycarbonylamino-3-[((4S)-(3-(5,6-methylenedioxy-benzimidazol-2-ylamino)propyl)-2,5-dioxoimidazolidin-1-yl)acetylamino]propionic Acid (17.1)

(17.1) is synthesized, as described in connection with the preparation of (15.3), by using 1,2-methylenedioxy-4,5-diaminobenzene, which is prepared from 1,2-methylenedioxy-4,5-dinitrobenzene by hydrogenation over 10% Pd/C in methanol, instead of using 1-methoxy-3,4diaminobenzene. 1,2-Methylenedioxy-4,5-dinitrobenzene is prepared from 1,2methylenedioxy-nitrobenzene by nitration, as described by D. S. Wulfman et al., Synthesis 1978, 924.

ES(+)-MS: 624 (M+H)$^+$

Example 18

3-[2-((4S)2-(1H-Benzimidazol-2-yl)ethyl)-2,5-dioxoimidazolidin-1-yl)acetylamino]-(2S)-benzyloxycarbonylaminopropionic Acid (18.5)

The synthesis was carried out in accordance with the following reaction sequence:

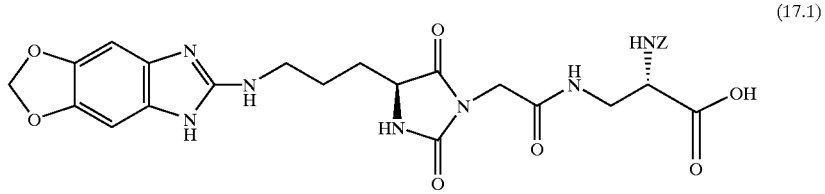

(17.1)

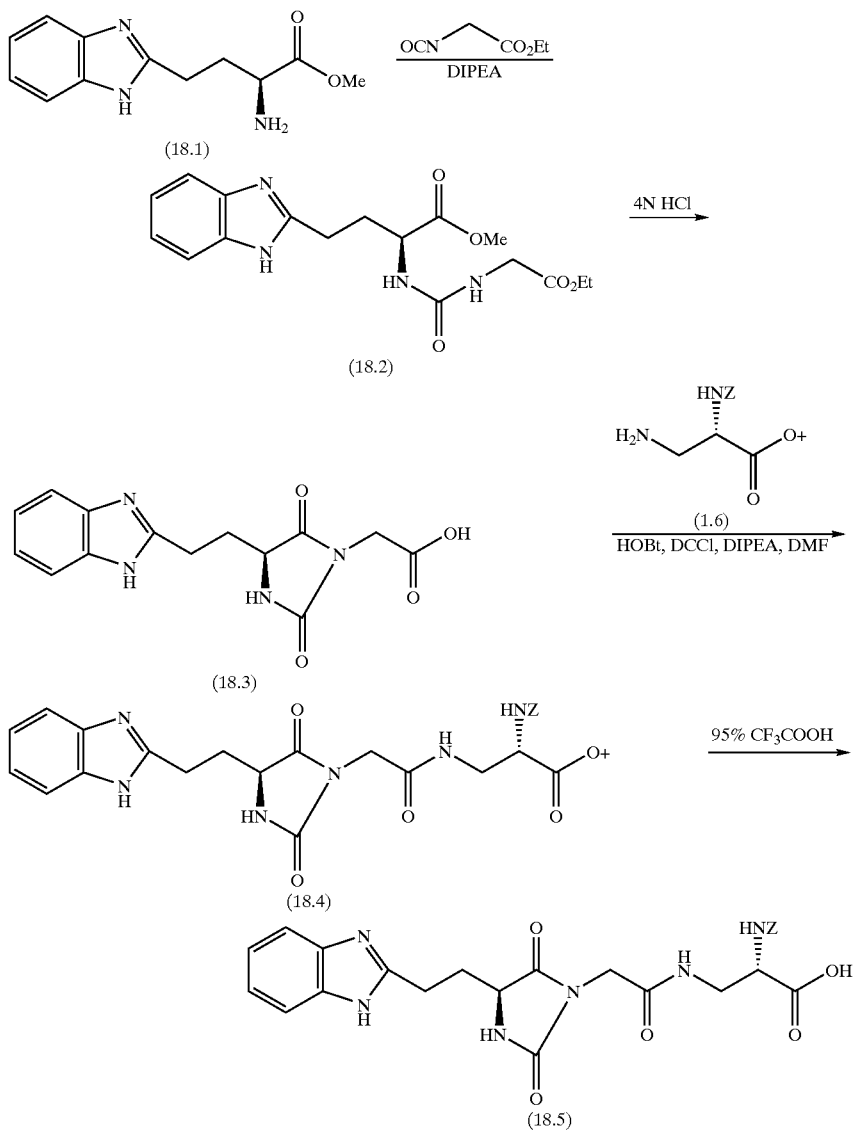

18a) Methyl (2S)-amino-4-(2-benzimidazolyl)butanoate (18.1)

(18.1) is prepared as described in Hans Lettre et al., Berichte 1951, 84, 719.

18b) Methyl (2S)-ethyloxycarbonylmethylaminocarbonylamino-4-(2-(1H-benzimidazolyl)butanoate (18.2)

3.4 ml (20 mmol) of diisopropylethylamine (DIPEA) and 2.58 g (20 mmol) of ethyl isocyanato acetate in absolute DMF are added, at 0° C., to a solution of 4.6 g (20 mmol) of (18.1). After stirring at room temperature for 16 h, the solvent is removed in vacuo and the residue is taken up in ethyl acetate; the ethyl acetate phase is then washed twice with a 10% solution of citric acid. The aqueous phase is adjusted to a pH of 10 with 2N KOH solution and extracted several times with ethyl acetate. The combined organic phases are dried over sodium sulfate, the drying agent is filtered off and the filtrate is concentrated in vacuo. 4.4 g (61%) of (18.2) are obtained.

18c) [(4S)-(2-(1H-Benzimidazol-2-yl)-ethyl)-2,5-dioxoimidazolidin-1-yl]acetic Acid (18.3)

A solution of 200 mg (0.55 mmol) of (18.2) in 4 ml of 4N HCl is stirred at room temperature for 16 h. After removing the solvent in vacuo, the residue is taken up in water and this solution is freeze-dried. 160 mg (53%) of (18.3) are obtained as a colorless solid.

18d) tert-Butyl 3-[2-((4S)-(2-(1H-benzimidazol-2-yl)ethyl)-2,5-dioxo-imidazolidin-1-yl)acetylamino]-(2S)-benzyloxycarbonylaminopropionate (18.4)

0.09 ml (0.53 mmol) of diisopropylethylamine (DIPEA) and 120 mg (0.58 mmol) of DCCl are added, at 0° C. to a solution of 160 mg (0.53 mmol) of (18.3), 72 mg (0.53 mmol) of HOBt and 156 mg (0.53 mmol) of (1.6) in 5 ml of DMF. The mixture is stirred at 0° C. for 20 min and at room temperature for 16 h. The precipitate is filtered off, the filtrate is concentrated and the residue is taken up in ethyl acetate; the ethyl acetate phase is then washed with a 10% solution of $KHCO_3$ and a saturated solution of NaCl and dried over sodium sulfate. After filtering, the solvent is removed in vacuo and the residue (18.4) is converted directly into (18.5).

18e) 3-[2-((4S)-(2-(1H-Benzimidazol-2-yl)ethyl)-2,5-dioxoimidazolidin-1-yl)-acetylamino]-(2S)-benzyloxycarbonylaminopropionic Acid (18.5)

A solution of ((18.4), crude product) in 5 ml of 95% trifluoroacetic acid is stirred at room temperature for 20 min. The solvent is removed in vacuo and the residue is dissolved in tert-butanol/water=1/1 and this solution is freeze-dried. 120 mg (44%, starting from (18.3)) of (18.5) are obtained as a pale yellow solid.

ES(+)-MS: 492 (M+H)$^+$

Example 19

(2S)-Benzyloxycarbonylamino-3-[2-((4S)-(3-guanidino-3-oxopropyl)-2,5-dioxoimidazolidin-1-yl)acetylamino] propionic Acid (19.3)

The synthesis is carried out in accordance with the following reaction sequence:

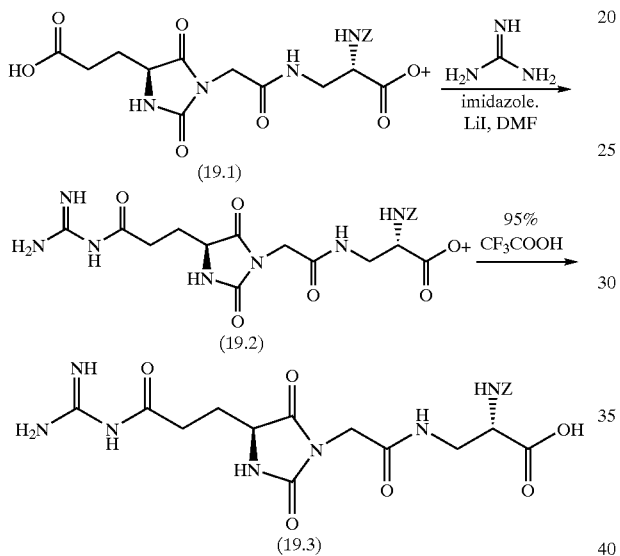

19a) tert-Butyl (2S)-benzyloxycarbonylamino-3-[((4S)-(2-carboxyethyl) -2,5dioxoimidazolidin-1-yl)acetylamino] propionate (19.1)

(19.1) is synthesized starting from L-glutamic acid in analogy with the synthesis of (7.6) from L-aspartic acid (see Example 7).

19b) tert-Butyl (2S)-benzyloxycarbonylamino-3-[2-((4S)-(3-guanidino-3-oxopropyl) -2,5-dioxoimidazolidin-1-yl)acetylamino]propionate (19.2)

12.8 mg (0.09 mmol) of lithium iodide and a solution of 500 mg (0.96 mmol) of (19.1) in 5 ml of DMF are added to a solution of 170 mg (2.88 mmol) of guanidine and 6.5 mg (0.09 mmol) of imidazole in 2 ml of DMF and the mixture is left to stir at room temperature overnight. The solvent is removed in vacuo and the residue is treated with ethyl acetate; the ethyl acetate phase is then washed with KHCO$_3$ solution and dried over sodium sulfate. After filtering, the solvent is removed in vacuo and 30 mg of (19.2, crude product) are obtained and used directly for synthesizing (19.3).

19c) (2S)-Benzyloxycarbonylamino-3-[2-((4S)-(3-guanidino-3-oxopropyl)-2,5-dioxoimidazolidin-1-yl) acetylamino]propionic Acid (19.3)

A solution of 30 mg of (19.2, crude product) in 1 ml of 95% trifluoroacetic acid is stirred at room temperature for 10 min. The solvent is removed in vacuo and the residue is purified through RP 18 by means of preparative HPLC. 9.5 mg (2%, starting from (19.1)) of (19.3) are obtained as a colorless solid after concentrating the product fractions and freeze-drying.

ES(+)-MS: 492 (M+H)$^+$

Example 20

(2S)-Benzyloxycarbonylamino-3-(2-(2,5-dioxo-(4S)-(2-(1,4,5,6-tetrahydro-pyrimidin -2-ylcarbamoyl)ethyl) imidazolidin-1-yl)acetylamino]propionic Acid (20.2)

The synthesis was carried out in accordance with the following reaction sequence:

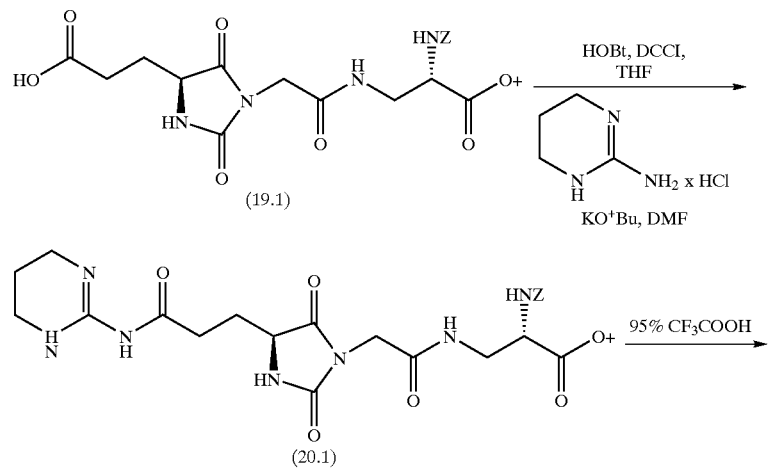

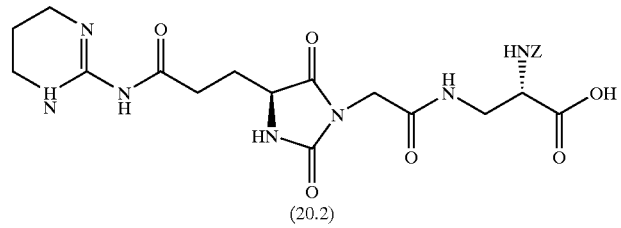

(20.2)

20a) tert-Butyl (2S)-benzyloxycarbonylamino-3-[2-(2,5-dioxo-(4S)-(2-(1,4,5,6-tetrahydropyrimidin-2-ylcarbamoyl)ethyl)imidazolidin-1-yl)acetylamino]propionate (20.1)

135 mg (1 mmol) of HOBt and 206 mg (1.1 mmol) of DCCl are added, while cooling with ice, to a solution of 506 mg (1 mmol) of (19.1) in 4 ml of absolute tetrahydrofuran and the mixture is left to stir for 30 min. This solution is then added to a solution of 136 mg (1 mmol) of 1,4,5,6-tetrahydropyrimidin-2-ylamine hydrochloride and 112 mg of potassium tert-butoxide in DMF and the mixture is left to stir at room temperature for 1 h. The solvent is removed in vacuo and the residue is triturated with diethyl ether. 90 mg (15%) of (20.1) are obtained after carrying out chromatography through silica gel using dichloromethane/methanol/acetic acid/water=911/0.1/0. 1, concentrating the product fractions and freeze-drying.

20b) (2S)-Benzyloxycarbonylamino-3-[2-(2,5-dioxo-4-(2-(1,4,5,6-tetrahydro-pyrimidin-2-ylcarbamoyl)ethyl)imidazolidin-1-yl)acetylamino]propionic Acid (20.2)

A solution of 80 mg (0.136 mmol) of (20.1) in 10 ml of 95% trifluoroacetic acid is stirred at room temperature for 20 min. The solvent is removed in vacuo and the residue is dissolved in water and this solution is freeze-dried. 70 mg (97%) of (20.2) are obtained as a colorless solid.

ES(+)-MS: 532 (M+H)$^+$

Example 21

4-[(4R,S)-(4-((1H-Benzimidazol-2-ylamino)methyl)phenyl)-4-methyl-2,5-dioxoimidazolidin-1-yl]-2-benzyloxycarbonylaminobutanoic Acid (21.7)

The synthesis was carried out in accordance with the following reaction sequence:

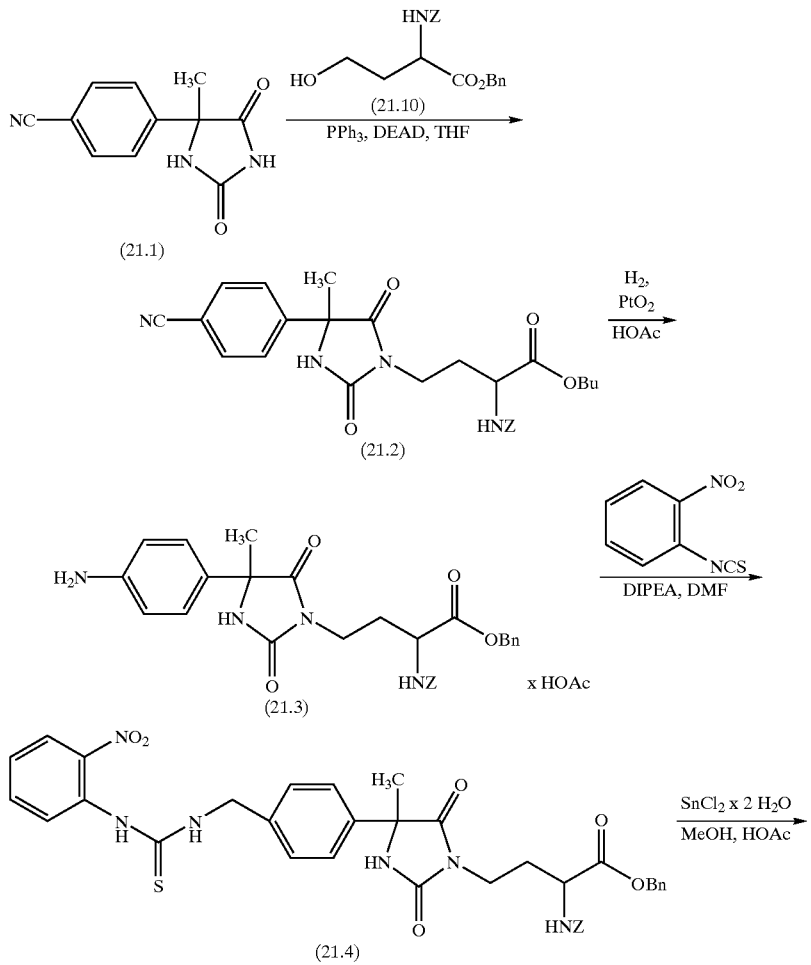

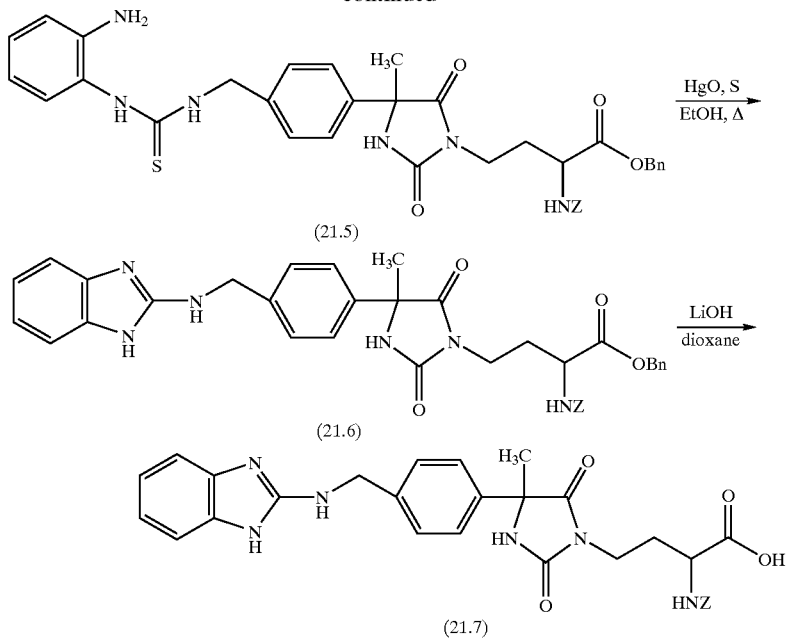

21a) 2-Benzyloxycarbonylamino-4-[(4R,S)-(4cyanophenyl)-4-methyl-2,5-dioxoimidazolidin-1-yl]butanoic Acid (21.2)

A solution of 870 mg (0.5 mmol) of diethyl azodicarboxylate (DEAD) in absolute tetrahydrofuran is added to a solution of 1.07 g (5 mmol) of (21.1) (synthesis, see WO 95/14008), 1.3 g (5 mmol) of triphenylphosphine and 1.7 g (5 mmol) of (21.10) in 20 ml of absolute tetrahydrofuran. After stirring at room temperature for 16 h, the solvent is removed in vacuo and the residue is taken up in ethyl acetate; the ethyl acetate phase is then washed with a 10% solution of citric acid and a saturated solution of NaHCO$_3$ and dried over sodium sulfate. After filtering, the solvent is removed in vacuo and the residue is chromatographed through silica gel using dichloromethane/tert-butyl methyl ether=1/1. 1.2 g (44%) of (21.2) are obtained after concentrating the product fractions.

21b) Benzyl 4-[(4R,S)-(4-aminomethylphenyl)-4-methyl-2,5-dioxoimidazolidin-1-yl]-2-benzyloxycarbonylaminobutanoate Acetic Acid Salt (21.3)

A solution of 1.2 g (2.22 mmol) of (21.2) in acetic acid is hydrogenated over 150 mg of platinum oxide. As soon as the uptake of hydrogen has come to an end (after approx. 3 h), the catalyst is filtered off, the filtrate is concentrated and the residue is purified through silica gel using dichloromethane/methanol/acetic acid/water=6/1/0. 10.1/0.1. 450 mg (34%) of (21.3) are obtained after concentrating the product fractions.

21c) Benzyl 2-benzyloxycarbonylamino-4-[(4R,S)-methyl-4-(4-(3-(2-nitro-phenyl)thioureidomethyl)phenyl)-2,5-dioxoimidazolidin-1-yl]butanoate (21.4)

135 mg (0.75 mmol) of 2-nitrophenyl isothiocyanate and 0.13 ml of diisopropylethylamine (DIPEA) are added to a solution of 410 mg (0.75 mmol) of (21.3) in 5 ml of DMF. After stirring at room temperature for 16 h, the solvent is removed in vacuo and the residue is chromatographed through silica gel using tert-butyl methyl ether. 380 mg (70%) of (21.4) are obtained.

21d) Benzyl 4-[(4R,S)-(4-(3-(2-aminophenyl)thioureamethyl)phenyl)-4-methyl-2,5-dioxoimidazolidin-1-yl]-2-benzyloxycarbonylaminobutanoate (21.5)

650 mg of SnCl$_2$×2 H$_2$O (2.9 mmol) and 3 drops of acetic acid are added to a solution of 360 mg (0.49 mmol) of (21.4) in 5 ml of methanol and the mixture is left to stir at room temperature for 16 h. After removing the solvent in vacuo, the residue is chromatographed through silica gel using dichloromethane/methanol=20/1. 280 mg (82%) of (21.5) are obtained.

(21e) Benzyl 4-[(4R,S)-(4-((1H-benzimidazol-2-ylamino)methyl)phenyl)-4-methyl-2,5-dioxoimidazolidin-1-yl]-2-benzyloxycarbonylaminobutanoate (21.6)

A mixture of 270 mg (0.38 mmol) of (21.5), 173 mg (0.8 mmol) of mercuric oxide and 3 mg of sulfur is heated under reflux for 12 h in 10 ml of ethanol. After filtering and removing the solvent in vacuo, 180 mg of (21.6, crude product) are obtained as a red-brown syrup which is converted directly into (21.7).

21f) 4-[(4R,S)-(4-((1H-benzimidazol-2-ylamino)methyl)phenyl)-4-methyl-2,5-dioxoimidazolidin-1-yl]-2-benzyloxycarbonylaminobutanoic Acid (21.7)

0.27 ml of an 1M solution of LiOH is added to a solution of 180 mg (approx. 0.27 mmol) of (21.6, crude product) in 4 ml of dioxane and the mixture is left to stir at room temperature overnight. The major part of the dioxane is removed in vacuo, the aqueous residue is adjusted to pH 5 with citric acid and the water phase is extracted with ethyl acetate. After drying over sodium sulfate, filtering and concentrating the filtrate in vacuo, the residue is chromatographed through silica gel using dichloromethane/methanol/acetic acid/water=611/0.110.1. 107 mg (49%, starting from (21.5)) of (21.7) are obtained as a colorless solid after concentrating the product fractions and freeze-drying.

ES(+)-MS: 571 (M+H)$^+$

21g) Synthesis of benzyl 2-benzyloxycarbonylamino-4-hydroxybutanoate (21.10)

The synthesis was carried out in accordance with the following reaction sequence:

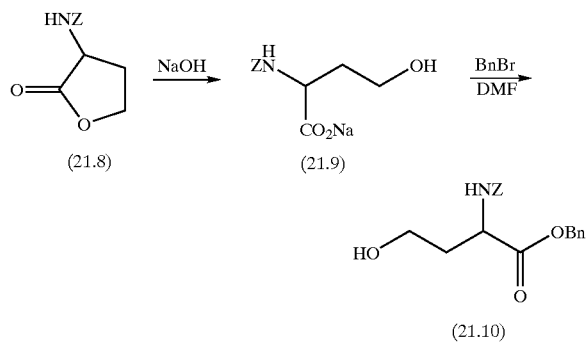

A suspension of 10 g (42 mmol) of (21.8) in 420 ml of 0.1M NaOH in ethanol is stirred at room temperature for 16 h. The reaction solution is concentrated, the residue is treated with toluene and the solvent is removed in vacuo. 130 ml of DMF and 9.34 g (54.6 mmol) of benzyl bromide are added and the mixture is left to stir at room temperature for 4 days. 2.1 liters of 1M NaHCO$_3$ solution are added and the whole is extracted 3 times with ethyl acetate. The combined ethyl acetate phases are washed with 1M NaHCO$_3$ solution and a saturated solution of NaCl and dried over magnesium sulfate. After filtering, the solvent is removed in vacuo and the residue is chromatographed through silica gel using dichloromethane/acetonitrile=20/1 to 20/6. The product fractions are concentrated and the residue is crystallized using diethyl ether/hexane. 5.4 g (38%) of (21.10) are obtained as colorless crystals.

Example 22

3-[2-((4S)-(3-(1H-Benzimidazol-2-ylamino)propyl)-2,5-dioxoimidazolidin-1-yl)acetylamino)-(2S)-(2-chlorobenzyloxycarbonylamino]propionic Acid (22.4)

The synthesis was carried out in accordance with the following reaction sequence:

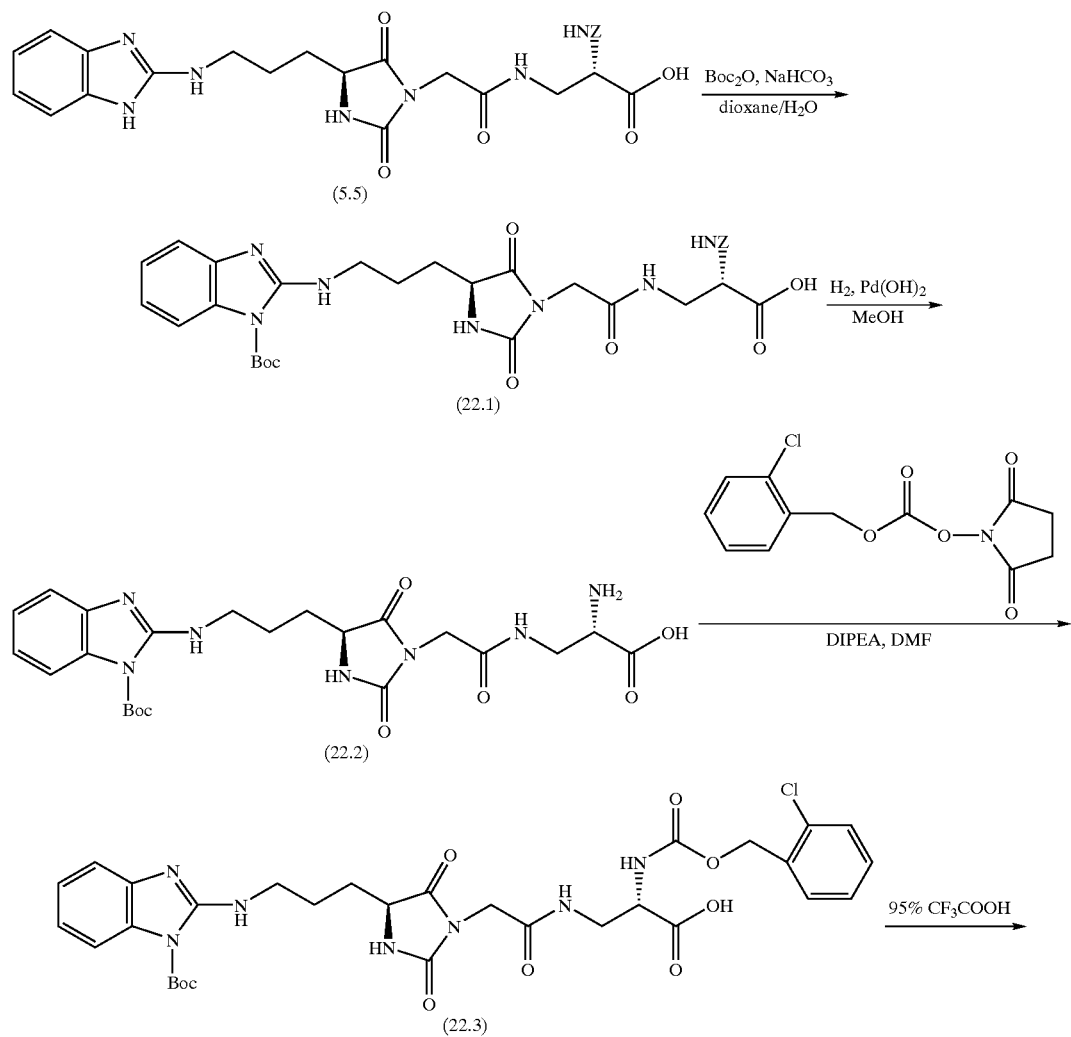

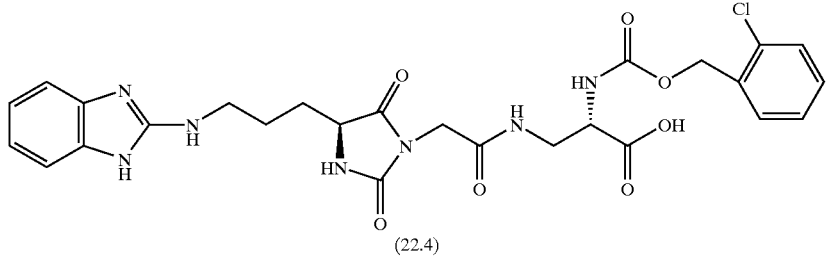

(22.4)

22a) 3-[2-((4S)-(3-(1-tert-Butoxycarbonylbenzimidazol-2-ylamino)propyl)-2,5-dioxoimidazolidin-1-yl)acetylamino]-(2S)-benzyloxycarbonylaminopropionic Acid (22.1)

168 mg (2 mmol) of NaHCO₃ and 437 mg (2 mmol) of di-tert-butyl dicarbonate are added to a solution of 551 mg (1 mmol) of (5.5) in 4 ml of dioxane/water=1/1 and the mixture is left to stir at room temperature for 16 h. The solvent is removed in vacuo and the residue is taken up in ethyl acetate; the ethyl acetate phase is then washed with a 2% solution of citric acid and a saturated solution of NaCl and dried over magnesium-sulfate. After filtering, the solvent is removed in vacuo and 614 mg (94%) of (22.1) are obtained as colorless crystals.

22b) (2S)-Amino-3-[2-((4S)-(3-(1-tert-butoxycarbonylbenzimidazol-2-yl-amino)propyl)-2,5-dioxoimidazolidin-1-yl)acetylamino]propionic Acid (22.2)

A solution of 600 mg (0.92 mmol) of (22.1) in methanol is hydrogenated over palladium hydroxide. The catalyst is filtered off, the filtrate is concentrated and the residue is subjected twice to rotary evaporation with toluene; it is then dried under high vacuum. 385 mg (81%) of (22.2) are obtained.

22c) 3-[2-((4S)-(3-(1-tert-butoxycarbonylbenzimidazol-2-ylamino)propyl)2,5-dioxoimidazolidin-1-yl)acetylamino)-(2S)-(2-chlorobenzyloxycarbonylamino] propionic Acid (22.3)

0.017 ml of diisopropylethylamine, and then a solution of 28.4 mg (0.1 mmol) of N-(2chlorobenzyloxycarbonyloxy) succinimide, are added, at 0° C., to a solution of 61.7 mg (0.12 mmol) of (22.2) in 2.5 ml of DMF and the reaction mixture is left to stir at room temperature for 16 h. The solvent is removed in vacuo and the residue is partitioned between ethyl acetate and 2% citric acid. The phases are separated and the organic phase is dried over magnesium sulfate. After filtering, concentrating the filtrate in vacuo and crystallizing the residue using diethyl ether, 36.5 mg (45%) of (22.3) are obtained as colorless crystals.

22d) 3-[2-((4S)-(3-(1H-Benzimidazol-2-ylamino) propyl)-2,5-dioxo-imidazolidin-1-yl)acetylamino)-(2S)-(2-chlorobenzyloxycarbonylamino]-propionic Acid (22.4)

A solution of 36.5 mg of (22.3) in 3 ml of 95% trifluoroacetic acid is stirred at room temperature for 1 h. The trifluoroacetic acid is removed in vacuo and the residue is subjected twice to rotary evaporation with toluene. The residue is dissolved in methanol, and (22.4) is precipitated with diethyl ether. After centrifuging, the residue is taken up in dilute acetic acid and this solution is freeze-dried. 24 mg (77%) of (22.4) are obtained as a colorless solid.

ES(+)-MS: 586 (M+H)⁺

Examples 23–33

Compounds (23) to (33) are prepared in accordance with the following reaction sequence:

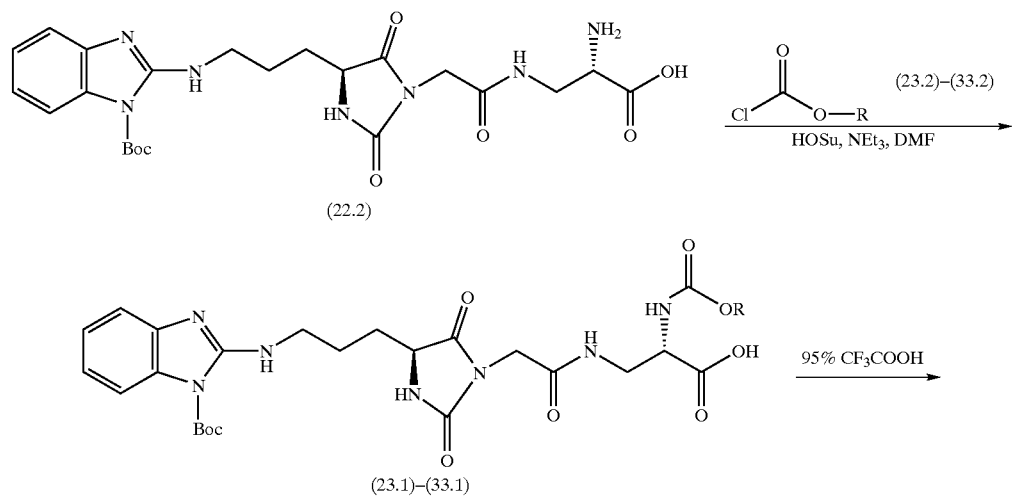

-continued

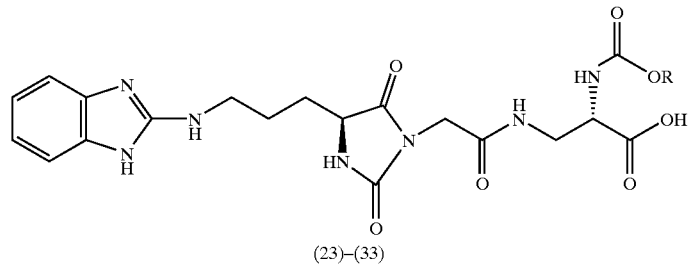

(23)–(33)

(Synthesis description, see after Example 33)

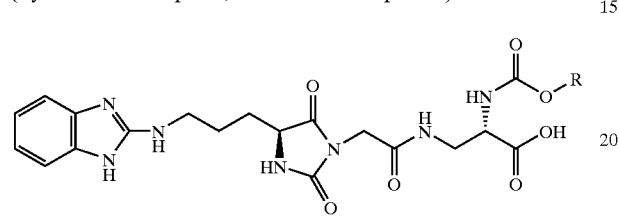

Example 23
R=

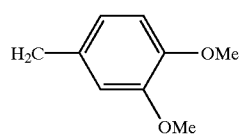

3-[2-(4S)-3-(1H-Benzimidazol-2-ylamino)propyl)-2,5-dioxoimidazolidin-1-yl)-acetylamino)2S)-(3,4-dimethoxybenzyloxycarbonylamino)propionic Acid (23)
ES(+)-MS: 612 (M+1)$^+$

Example 24
R=

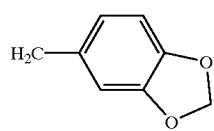

3-2((4S)-3-(1H-Benzimidazol-2-ylamino)propyl)-2,5-dioxoimidazolidin-1-yl)-acetylamino)-(2S)-(3,4-methylenedioxybenzyloxycarbonyl)propionic Acid (24)
ES(+)-MS: 624 (M+1)$^+$

Example 25
R=

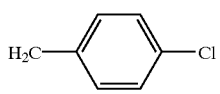

3-[2-((4S)-(3-(1H-Benzimidazol-2-ylamino)propyl)-2,5-dioxoimidazolidin-1-yl)acetylamino]-(2S)-(4-chlorobenzyloxycarbonylamino)propionic Acid (25)
ES(+)-MS: 586 (M+1)$^+$

Example 26
R=

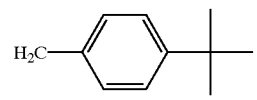

3-[2-((4S)-(3-(1H-Benzimidazol-2-ylamino)propyl)-2,5-dioxoimidazolidin-1-yl)acetylamino]-(4S)-(4-tert-butylbenzyloxycarbonylamino)propionic Acid (26)
ES(+)-MS: 608 (M+1)$^+$

Example 27
R=

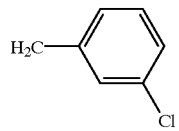

3-[2-((4S)-(3-(1H-Benzimidazol-2-ylamino)propyl)-2,5-dioxoimidazolidin-1-yl)acetylamino]-(2S)-(3-chlorobenzyloxycarbonylamino)propionic Acid (27)
ES(+)-MS: 586 (M+1)$^+$

Example 29
R=

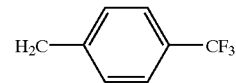

3-[2-((4S)-3-(1H-Benzimidazol-2-ylamino)propyl)-2,5-dioxoimidazolidin-1-yl)acetylamino]-(2S)-(4-trifluoromethylbenzyloxycarbonylamino)propionic Acid (29)
ES(+)-MS: 620 (M+1)$^+$

Example 30
R=

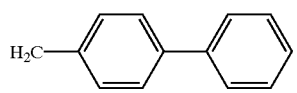

3-[2-((4S)-(3-(1H-Benzimidazol-2-ylamino)propyl)-2,5-dioxoimidazolidin-1-yl)-acetylamino]-(2S)-(4-phenylbenzyloxycarbonylamino)propionic Acid (30)
ES(+)-MS: 628 (M+1)$^+$

Example 31

R=

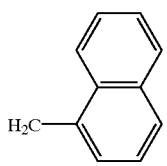

3-[2-((4S)-(3-(1H-Benzimidazol-2-ylamino)propyl)-2,5-dioxoimidazolidin-1-yl)acetylamino]-(2S)-(naphth-1-ylmethoxycarbonylamino)propionic Acid (31)

ES(+)-MS: 602 (M+1)$^+$

Example 32

R=

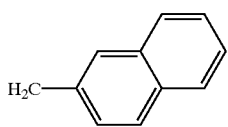

3-[2-(4S)-(3-(1H-Benzimidazol-2-ylamino)propyl)-2,5-dioxoimidazolidin-1-yl)acetylamino]-(2S)-(naphth-2-ylmethoxycarbonylamino)propionic Acid (32)

ES(+)-MS: 602 (M+1)$^+$

Example 33

R=

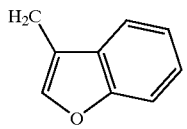

(2S)-(Benzofuran-3-ylmethoxycarbonylamino)-3-[2-((4S)-(3-(1H-benzimidazol-2-ylamino)propyl)-2,5-dioxoimidazolidin-1-yl)acetylamino]propionic Acid (33)

ES(+)-MS: 592 (M+1)$^+$ a) Preparation of the Chloroformic Esters (23.2)–(33.2)

The synthesis is effected in accordance with the following general preparation protocol:

A solution of 6 equivalents of the corresponding alcohol (HO—R) and 6 equivalents of pyridine in absolute dichloromethane is added dropwise, at 0° C., to a solution of 2.2 equivalents of bis(trichloromethyl)carbonate in absolute dichloromethane. The mixture is then left to stir at room temperature for 2 h, after which the solvent is removed in vacuo and the residue is taken up in ethyl acetate or ether; this mixture is left to stand at room temperature for 30 min and any resulting precipitate is then filtered off. After the solvent has been removed in vacuo, the residue is dried under high vacuum and used directly for synthesizing (23.1)–(33.1).

b) Preparation of the Compounds (23.1)–(33.1)

The synthesis is effected in accordance with the following general preparation protocol:

1 equivalent of the corresponding chloroformic ester (23.2)–(33.2) and 1 equivalent of diisopropylethylamine (DIPEA) are added, at 0° C., to a solution of 1 equivalent of N-hydroxysuccinimide in THF. The mixture is left to stir at 0° C. for 30 min and at room temperature for 45 min and this solution is then added to a solution of 1 equivalent of (22.2) in DMF. The mixture is left to stir at room temperature until the reaction has come to an end and the solvent is then removed in vacuo. The residue is taken up in ethyl acetate and the ethyl acetate phase is washed 2 times with an aqueous solution of citric acid (pH 3) and with a saturated solution of NaCl. After drying over sodium sulfate, filtering and removing the solvent in vacuo, the residue is chromatographed through silica gel. The compounds (23.1)–(33.1) are obtained after concentrating the product fractions.

c) Preparation of the compounds (23)–(33)

The preparation is effected from (23.1)–(33.1) by cleaving the tert-butoxycarbonyl group with 95% trifluoroacetic acid as described in connection with the preparation of (22.4) from (22.3).

Example 34

3-[8-(3-(1H-Benzimidazol-2-ylamino)propionyl)-2,4-dioxo-1,3,8-triaza-spiro[4.5]dec-3-yl]-(2S)-benzyloxycarbonylaminopropionic Acid (34.12)

The synthesis was carried out in accordance with the following reaction sequence:

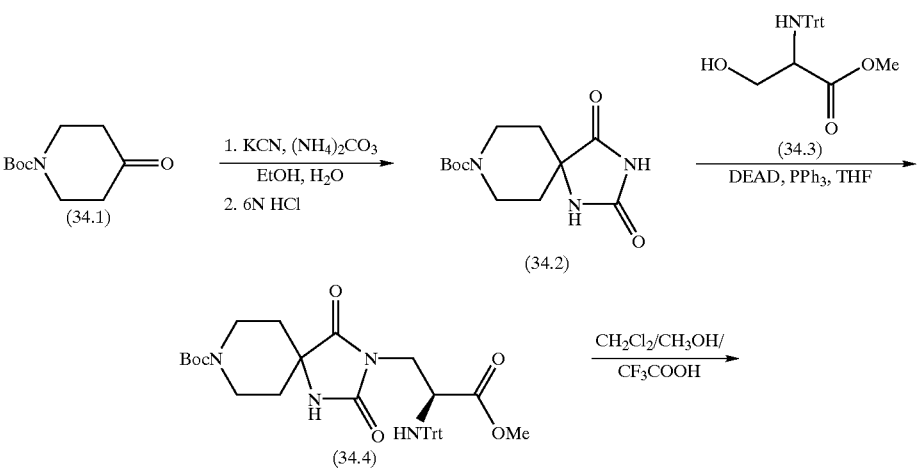

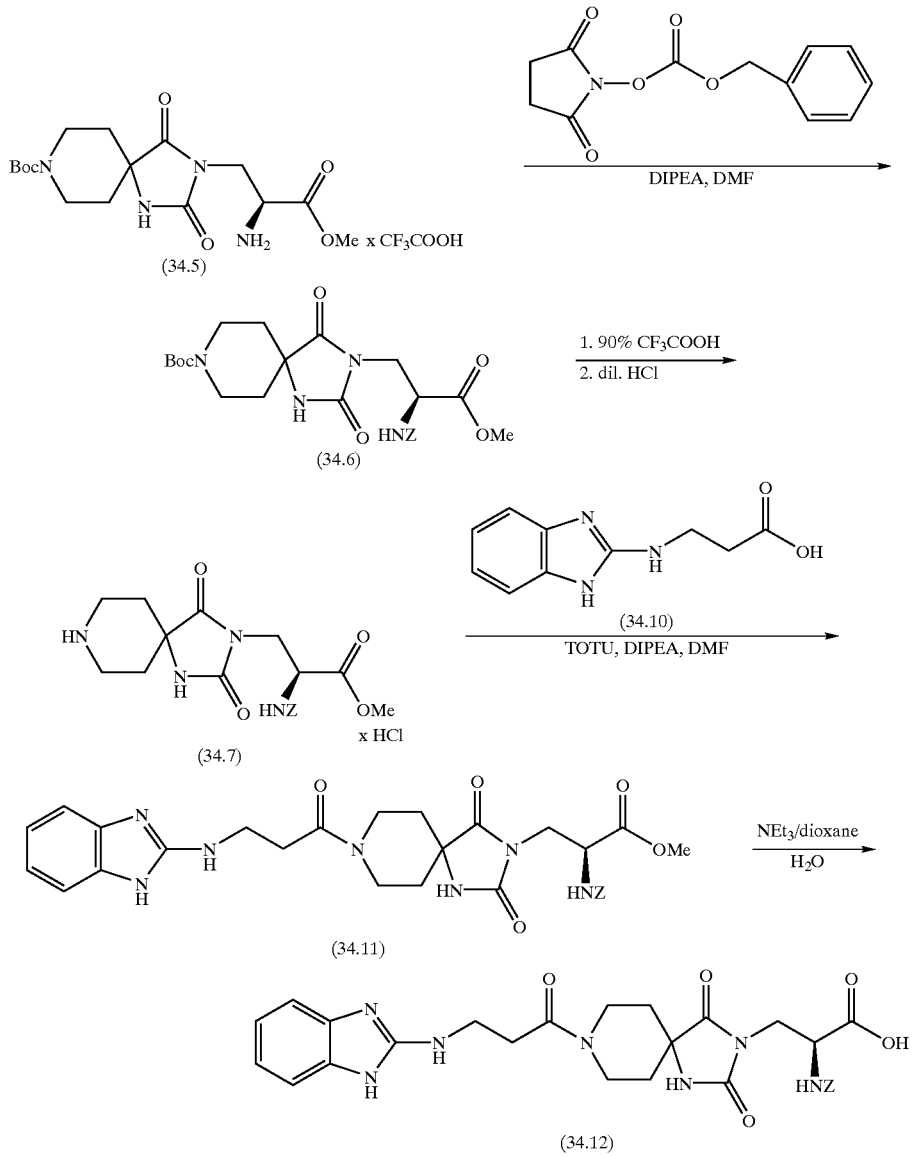

34a) tert-Butyl 2,4-dioxo-1,3,8-triazaspiro[4.5]decane-8-carboxylate (34.2)

2.12 g (32.6 mmol) of potassium cyanide are added to a solution of 5 g (25.1 mmol) of N tert-butoxycarbonyl-4-piperidone (34.1) and 24.01 g (250 mmol) of ammonium carbonate in 80 ml of EtOH/water=1/1 and the mixture is left to stir at 60° C. for 5 h. The pH is subsequently adjusted to 6.3 by adding 6N HCl and the mixture is stirred at 60° C. for a further 1.5 h. The precipitate is filtered off with suction and dried under high vacuum. 3.43 g of (34.2) are obtained as a colorless solid. A further 1.0 g of (34.2) is obtained by extracting the filtrate with dichloromethane, drying the organic phase over sodium sulfate, filtering and removing the solvent in vacuo. Total yield of (34.2): 4.43 g (66%) of colorless solid.

34b) N-Trityl-L-serine Methyl Ester (34.3)

A solution of 10.75 g (38.56 mmol) of trityl chloride is added, at 0° C., to a solution of 6 g (38.56 mmol) of L-serine methyl ester hydrochloride and 7.8 g (77.12 mmol) of triethylamine in absolute THF and this solution is left to stir at 0° C. for 4 h and then at room temperature for 2 days. The solvent is removed in vacuo and the residue is partitioned between dichloromethane and a 10% aqueous solution of citric acid. The phases are separated and the organic phase is washed with water and dried over sodium sulfate. Following filtration, the solvent is removed in vacuo and the residue is chromatographed through silica gel using heptane/ethyl acetate=6/4. 8 g (58%) of (34.3) are obtained after concentrating the product fractions.

34c) tert-Butyl 3-[2-methoxycarbonyl-(2S)-(tritylamino)ethyl]-2,4-dioxo-1,3,8-triazaspiro[4.5]decane-8-carboxylate (34.4)

A solution of 3.6 g (13.37 mmol) of (34.2) in 15 ml of absolute THF is added to a solution of 3.72 g (10.3 mmol) of (34.3) and 3.5 g (13.34 mmol) of triphenylphosphine in 20 ml of absolute THF. 2.11 ml (13.37 mmol) of diethyl azodicarboxylate (DEAD) are added to this solution and the reaction mixture is stirred at room temperature until the reaction has come to an end. The solvent is removed in vacuo and the residue is chromatographed through silica gel using heptane/ethyl acetate. 6 g (95%) of (34.4) are obtained after concentrating the product fractions.

34d) tert-Butyl 3-((2S)-amino-2-methoxy carbonylethyl)-2,4-dioxo-1,3,8-triazaspiro[4.5]decane-8-carboxylate (34.5)

A solution of 4.6 g (7.5 mmol) of (34.4) in 180 ml of dichloromethane/methanol/trifluoroacetic acid=95.5/3/1.5 is stirred at room temperature for 10 min. The reaction mixture is concentrated and the residue is chromatographed through silica gel. 3.14 g (87%) of (34.5) are obtained after concentrating the product fractions.

34e) tert-Butyl 3-((2S)-benzyloxycarbonylamino-2-methoxycarbonylethyl)-2,4-dioxo-1,3,8-triazaspiro[4.5]decane-8-carboxylate (34.6)

2.08 g (16.1 mmol) of diisopropylethylamine in 25 ml of absolute DMF are added to a solution of 3.14 g (8.48 mmol) of (34.5) and 2.11 g (8.48 mmol) of N-benzyloxycarbonyloxysuccinimide in 80 ml of absolute DMF and the mixture is left to stir at room temperature for 3 h. The solvent is removed in vacuo and the residue is chromatographed through silica gel using heptane/ethyl acetate=6/4. (34.6) is obtained after concentrating the product fractions.

34f) Methyl (2S)-benzyloxycarbonylamino-3-(2,4-dioxo-1,3,8-triazaspiro[4.5]dec-3-yl)propionate Hydrochloride (34.7)

A solution of 4.7 g (9.3 mmol) of (34.6) in 100 ml of 90% trifluoroacetic acid is left to stir at room temperature for 45 min. The trifluoroacetic acid is removed in vacuo and the residue is chromatographed through Sephadex LH 20 using water/butanol/acetic acid=43/4.3/3.5. The product fractions are concentrated and freeze-dried. 1.99 g (53%, starting from (34.5)) of (34.7) are obtained as a colorless solid after adding dilute HCl and freeze-drying once again.

34g) Methyl 3-[8-(3-(1H-benzimidazol-2-ylamino)propionyl)-2,4-dioxo-1,3,8-triazaspiro[4.5]dec-3-yl]-(2S)-benzyloxycarbonylaminopropionate (34.11)

(34.11) is synthesized by coupling (34.7) with (34.10), as described in Example 15 in connection with the synthesis of (15.3) from (15.2).

34h) 3-[8-(3-(1H-Benzimidazol-2-ylamino)propionyl)-2,4-dioxo-1,3,8-triazaspiro[4.5]dec-3-yl]-(2S)-benzyloxycarbonylaminopropionic acid (34.12)

(34.12) is synthesized by the ester cleavage of (34.11), as described in Example 3 in connection with the synthesis of (3.11) from (3.10).

ES(+)-MS: 578 (M+H)+

34i) Synthesis of (34.10)

3-(1H-Benzoimidazol-2-ylamino)propionic Acid (34.10)

(34.10) is prepared in accordance with the following reaction scheme:

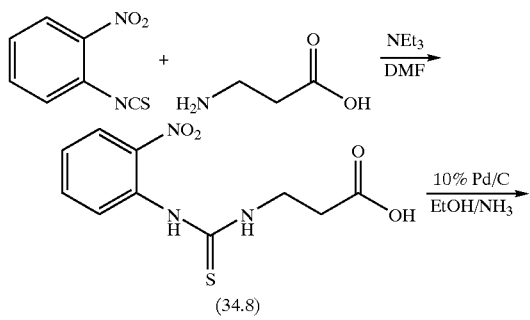

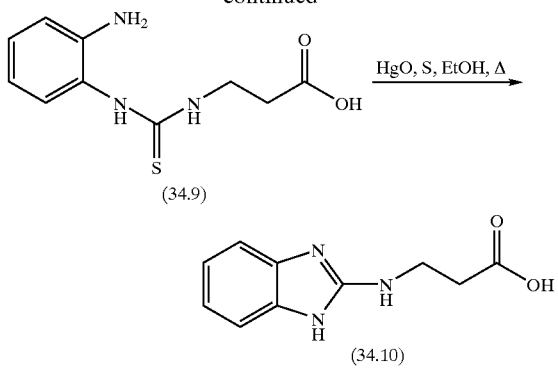

a) 3-[3-(2-Nitrophenyl)thiourea]propionic Acid (34.8)

3.8 ml (27.75 mmol) of triethylamine are added to a solution of 5 g (27.75 mmol) of 2-nitrophenyl isothiocyanate and 2.5 g (27.75 mmol) of β-alanine in 80 ml of DMF and the mixture is stirred until the reaction has come to an end. The solvent is removed in vacuo and the residue is partitioned between ethyl acetate and KHSO$_4$/K$_2$SO$_4$ solution. The phases are separated and the organic phase is dried over sodium sulfate. After filtering, the solvent is removed in vacuo and the residue is chromatographed through silica gel. 5.3 g (71%) of (34.8) are obtained after concentrating the product fractions.

b) 3-[3-(2-Aminophenyl)thioureido]propionic Acid (34.9)

5.3 g (19.7 mmol) of (34.8) in 410 ml of ammonia-saturated EtOH are hydrogenated at room temperature for 3 h over 6.44 g of 10% Pd/C. The catalyst is filtered off, the filtrate is concentrated in vacuo and the residue [1.9 g of (34.9), crude product] is used directly for synthesizing (34.10).

c) 3-(1H-Benzoimidazol-2-ylamino)propionic Acid (34.10)

A mixture composed of (34.9), 3.44 g (14.79 mmol) of mercuric oxide and 50 mg of sulfur in 40 ml of ethanol is heated under reflux for 5 h. After filtering, the filtrate is concentrated and the residue is heated to reflux for 1 h with 6N HCl; this latter solution is then freeze-dried. Fraction 1 of (34.9) is obtained. The filter residue is decocted several times with water and the combined water phases are freeze-dried. Fraction 2 of (34.9) is obtained. Fractions 1 and 2 are combined and chromatographed through Sephadex LH 20 using water/butanol/acetic acid=43/4.3/3.5. The product fractions are concentrated and freeze-dried. 340 mg (8%, starting from (34.8)) of (34.10) are obtained as a colorless solid.

Example 35

3-[2-(4(E or Z)-(3-(1H-Benzimidazol-2-ylamino)propylidene)-2,5-dioxoimidazolidin-1-yl)acetylamino]-(2S)-benzyloxycarbonylaminopropionic Acid (E-35.8) or (Z-35.8), Respectively The synthesis was carried out in accordance with the following reaction sequence:

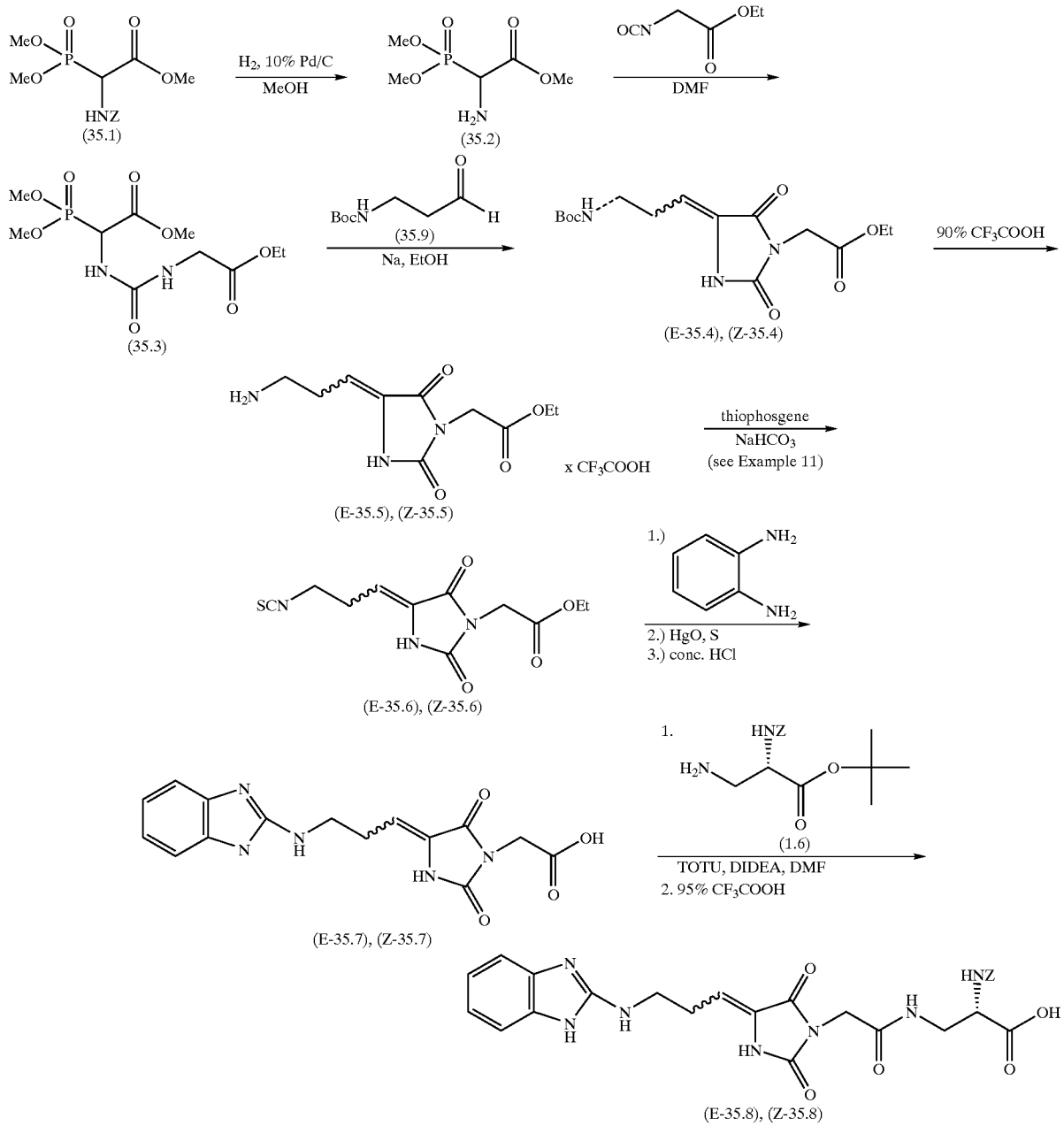

35a) Methyl 3-amino-3-(dimethoxyphosphoryl)propionate (35.2)

10 g (30.19 mmol) of Z-phosphonoglycine trimethyl ester (35.1) in 300 ml of methanol are hydrogenated over 10% Pd/C. After 1 h, the catalyst is filtered off and the filtrate is concentrated in vacuo. 4.6 g of (35.2) are obtained as a crude product which is used directly for synthesizing (35.3).

35b) Methyl 3-(dimethoxyphosphoryl)-3-(3-ethoxycarbonylmethylurea)propionate (35.3)

2.62 ml (23.4 mmol) of ethyl isocyanatoacetate are added to a solution of (35.2) in 20 ml of DMF. After 16 h at room temperature, a further 0.262 ml (2.34 mmol) of ethyl isocyanatoacetate is added and the reaction mixture is stirred at room temperature for a further 2 h. The solvent is removed in vacuo and the residue is partitioned between dichloromethane and KHSO$_4$/K$_2$SO$_4$ solution. The phases are separated and the organic phase is washed with water. After drying the organic phase over sodium sulfate, filtering and concentrating the filtrate in vacuo, 6.2 g [63%, starting from (35.1)] of (35.3) are obtained.

35c) Ethyl [4(E or Z)-(3-tert-butoxycarbonylaminopropylidene)-2,5-dioxo-imidazolidin-1-yl]acetate (E-35.4) or (Z-35.4), respectively A solution of 5.8 g (17.84 mmol) of (35.3) in 30 ml of absolute EtOH is added to a solution of 451 mg (18.8 mmol) of sodium in absolute EtOH. A solution of (35.9), prepared from β-alanine in analogy with O. P. Goel et al., Org. Synth. 1988, 67, 69, is added to the initial solution. After stirring at room temperature for 3 h, the solvent is removed in vacuo and the residue is partitioned between water and diethyl ether. The phases are separated and the organic phase is dried over sodium sulfate. After filtering, the residue is chromatographed through silica gel using dichloromethane/methanol=99/1. 2.25 g of (E- or Z-35.4) and 1.95 g of (Z- or E-35.4) are obtained. Total yield: 4.2 g (69%) of (35.4)

35d) Ethyl [4(E or Z)-(3-aminopropylidene)-2,5-dioxoimidazolidin-1-yl]acetate trifluoroacetic Acid Salt (E-35.5) or (Z-35.5), Respectively A solution of 2.25 g (6.6 mmol) of (Z- or E-35.4) in 25 ml of 90% trifluoroacetic acid is stirred at room temperature for 1 h. The trifluoroacetic acid is removed in vacuo and the residue is diluted with water and this mixture is freeze-dried. 2.2 g (94%) of (Z- or E-35.5) are obtained. In an analogous manner, 1.95 g (97%) of (E- or Z-35.5) are obtained from 1.95 g (5.71 mmol) of (E- or Z-35.4).

35e) Ethyl [4(E or Z)-(3-isothiocyanatopropylidene)-2,5-dioxoimidazolidin-1-yl]-acetate (E-35.6) or (Z-35.6), Respectively (E-35.6) or (Z-35.6) is synthesized from (E-35.5) or (Z-35.5), respectively, as described in Example 11 in connection with the synthesis of (11.2) from (11.1).

35f) [4(E or Z)-(3-(1H-Benzoimidazol-2-ylamino)propylidene)-2,5dioxo-imidazolidin-1-yl]acetic Acid Hydrochloride (E-35.6) or (Z-35.6), Respectively (E-35.7) or (Z-35.7) is synthesized from (E-35.6) or (Z-35.6), respectively, as described in Example 15 in connection with the synthesis of (15.2) from (11.2).

35g) 3-[2-(4(E or Z)-(3-(1H-Benzimidazol-2-ylamino)propylidene)-2,5-dioxo-imidazolidin-1-yl)acetylamino]-(2S)-benzyloxycarbonylaminopropionic Acid (E-35.8) or (Z-35.8), Respectively (E-35.8) or (Z-35.8) is synthesized from (E-35.7) or (Z-35.7), respectively, as described in Example 15 in connection with the synthesis of (15.3) from (15.2).

(E-35.8) or (Z-35.8): ES(+)-MS: 550 (M+H)⁺

Example 36

3-[2-(4(Z or E)-[3-(1H-Benzimidazol-2-ylamino)propylidene)-5-oxo-2-thioxo-imidazolidin-1-yl)acetylamino]-(2S)-benzyloxycarbonylaminopropionic Acid (Z-36) or (E-36), Respectively

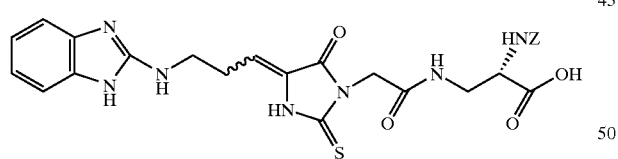

(E-36), (Z-36)

(Z-36) or (E-36) is synthesized as described in Example 35 with, in this case, (35.2) being reacted with methyl isothiocyanatoacetate instead of ethyl isocyanatoacetate. The subsequent synthesis is effected in analogy with Example 35.

(Z-36) or (E-6): ES(+)-MS: 566 (M+H)⁺

Example 37

3(4-(E/Z-(4-Guanidinocarbonylbenzylidene)-2,5-dioxoimidazolidin-1-yl)-(2S)-N-benzyloxycarbonylalanine (E/Z-37.5)

The synthesis was carried out in accordance with the following reaction sequence:

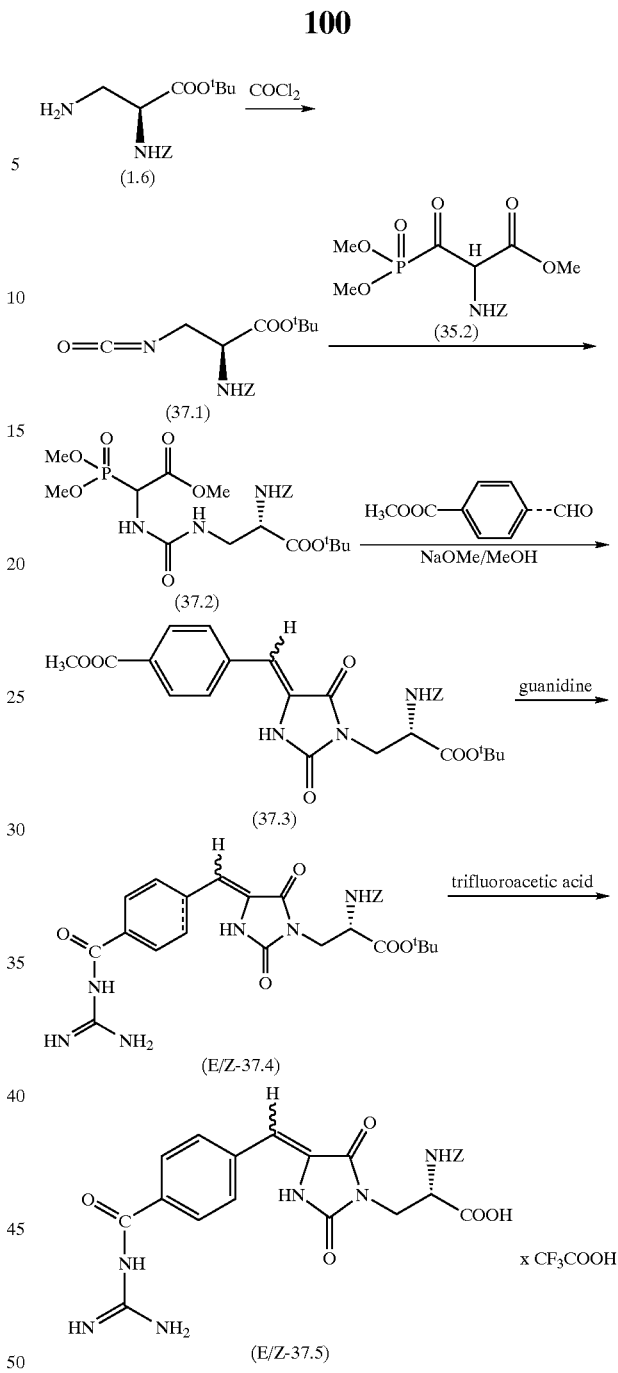

37a) 2-Isocyanato-Z-alanine tert-butyl Ester (37.1)

A solution of 2.94 g (10 mmol) of Z-Dap-O-t-Bu (1.6) in 80 ml of methylene chloride is cooled down to approx. 0° C. in an ice bath, together with 80 ml of a saturated solution of sodium bicarbonate, while being stirred vigorously. After adjusting the stirring process and separating the phases, 10.4 ml of a 1.93 molar solution of phosgene in toluene is introduced rapidly into the organic phase and this mixture is left to react to completion once again while being stirred effectively and subjected to external cooling. After a further 10 min, the phases are separated and the aqueous phase is extracted a further 2 times with 40 ml of methylene chloride on each occasion. The combined organic extracts are dried with anhydrous magnesium sulfate, filtered and freed of solvent in vacuo. Approx. 3.0 g are obtained of a colorless oil, which was used for synthesizing (37.2) without further purification.

37b) (t)-Butyl N'-(dimethoxyphosphoryl)-(methoxycarbonyl)methylureido-N-(2S)-benzyloxycarbonylamino-3-propionate (37.2)

Under a protective gas atmosphere of argon, the quantity of (37.1) obtained from 37a) is dissolved in approx. 30 ml of dichloromethane and 1.97 g of (35.2), dissolved in approx. 50 ml of dichloromethane, are added at room temperature and while stirring. The reaction is complete after approx. 2 h. The solution is washed firstly with 100 ml of a 2N solution of potassium hydrogen sulfate and then with 100 ml of water, after which the organic phase is dried with anhydrous magnesium sulfate and filtered. Approx. 4.6 g of pure (37.2) (89%) remain after removing the solvent in vacuo.

37c): (t)-Butyl E- or Z-3-(4-(4-methoxy-carbonylbenzylidene)-2,5-dioxo-imidazolidin-1-yl)-2-N-benzyloxycarbonylaminopropionate (37.3)

1.55 g (3 mmol) of (37.2) are dissolved in approx. 8 ml of methanol and 0.6 ml (approx. 3.3 mmol) of a 30% solution of sodium methoxide in methanol is added. To this are slowly added dropwise (under argon protective gas and while stirring at room temperature) 8 ml of a methanolic solution which contains 0.59 g (3.6 mmol) of methyl 4-formylbenzoate. The reaction is complete after approx. 1 h. The solution is concentrated in vacuo and the residue is taken up in ethyl acetate; this solution is washed with water, dried, filtered and concentrated. 1.6 g of an E/Z mixture of (37.3) are obtained.

The diastereomers can be separated by chromatography using ethyl acetate/n-heptane (2:1) as the eluent and silica gel as the carrier material: 0.85 g of (Z-37.3) and 0.7 g of (E-37.3) are obtained.

37d) (t)-Butyl E- or Z-3-(4-(4-guanidino-carbonylbenzylidene)-2,5-dioxo-imidazolidin-1-yl)-(2S)-N-benzyloxycarbonylaminopropionate (E- or Z-37.4, Respectively)

0.262 g (0.5 mmol) of (Z-37.3) is dissolved in 5 ml of abs. tetrahydrofuran, 0.148 g (2.5 mmol) of guanidine is added and the mixture is heated under reflux for 20 h. After removing the solvent in vacuo, the residue is chromatographed through silica gel using methanol/methylene chloride (1:10). 0.05 g of (Z-37.4) is obtained. (E-37.3) is reacted analogously, with 1,2-dimethoxyethane being used as solvent. 0.12 g of (E-37.4) is obtained.

37e) E- or Z-3-(4-(4-Guanidinocarbonylbenzylidene)-2,5-dioxoimidazolidin-1-yl)-(2S)-N-benzyloxy- carbonylaminopropionic acid trifluoroacetic Acid Salt (E- or Z-37.5, Respectively)

0.12 g of (E-37.4) is dissolved in ice-cold 90% trifluoroacetic acid (approx. 10 ml) and this solution is stirred at room temperature for 1.5 h under argon protective gas. After removing the solvent in vacuo, the residue is chromatographed through RP 18 using methanol/water. The product fractions are concentrated and 0.06 g of (E-37.5) is obtained. 0.02 g of (Z-37.5) is obtained in an analogous manner from 0.05 g of (Z-37.4).

Example 38

3-(4-E/Z-(4-(3,4,5,6-Tetrahydropyrimidin-2-yl)aminocarbonylbenzylidene)-2,5-dioxoimidazolidin-1-yl)-(2S)-N-benzyloxycarbonylalanine (E/Z-38.4)

The synthesis is carried out in accordance with the following reaction sequence:

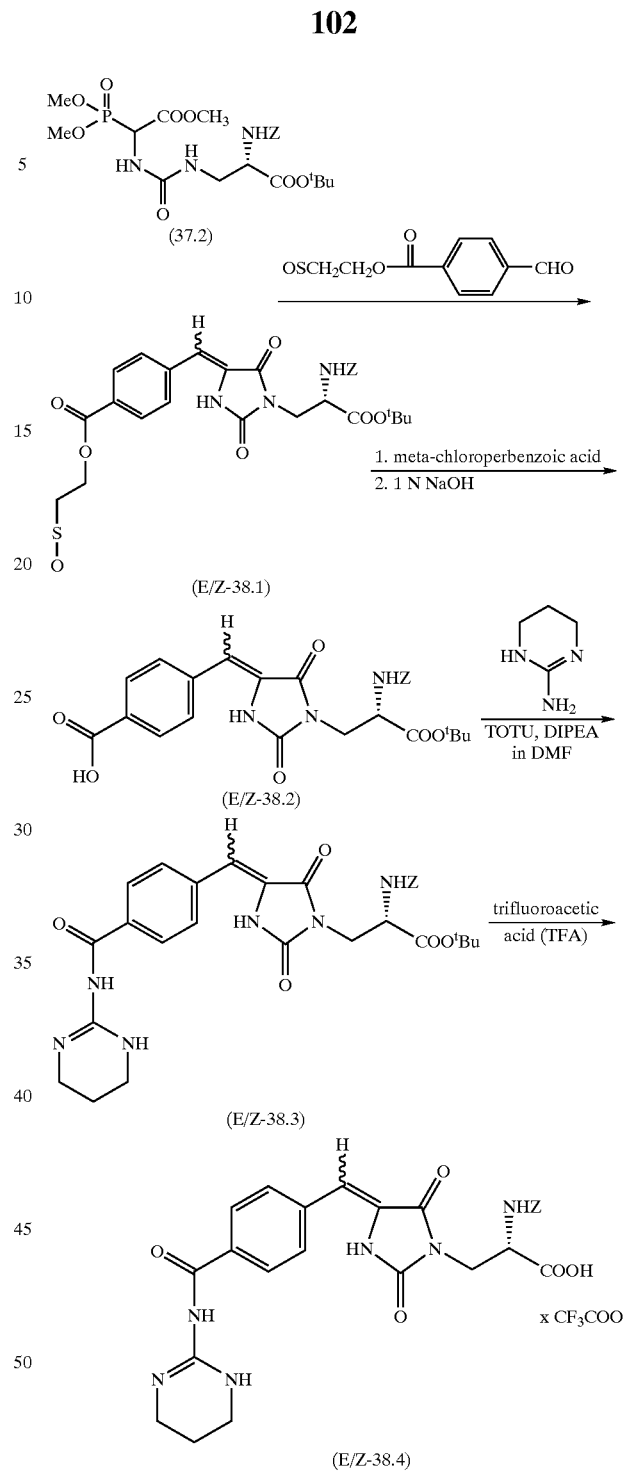

38a) tert-Butyl E- or Z-3-(4-((2-phenylthio)ethyloxycarbonylbenzylidene)-2,5-dioxoimidazolidin-1-yl)-(2S)-N-benzyloxycarbonylaminopropionate (E-or Z-38.1, Respectively)

In analogy with reaction 37c), 0.157 g of Z-38.1 and 0.1539 of (E-38.1) (total yield: approx. 91%), which can be isolated individually by chromatography, are obtained from 0.259 g (0.5 mmol) of (37.2) and 0.172 g (0.6 mmol) of (2-phenylthio)ethyl 4-formylbenzoate.

38b) tert-Butyl E- or Z-3-(4-(carboxylbenzylidene)-2,5-dioxoimidazolidin-1-yl)-2-N-benzyloxy- carbonylamino-propionate (E- or Z-38.2, Respectively)

0.155 g (0.24 mmol) of (Z-38.1) is dissolved in 5 ml of dry methylene chloride and 0.098 g (0.4 mmol) of 65% meta-chloroperbenzoic acid is added. The reaction is complete after 1.5 h. The methylene chloride solution is washed with sodium bisulfite (approx. 10% strength) and then with water. After drying over magnesium sulfate, filtering and removing the solvent, 0.15 g of the phenylsulfonylethyl ester remains, which can be introduced, without further treatment, into a mixture of 8 ml of dioxane, 1.4 ml of methanol and 0.19 ml of 1N NaOH. After 16 h, the solvents are removed in vacuo and the residue is chromatographed through silica gel using methylene chloride/methanol (95:5).

Yield: 0.033 g of (Z-38.2). 0.051 g of (E38.2) is obtained in an analogous manner from 0.157 g (0.24 mmol) of (E-38.1).

38c) tert-Butyl 3-(4-E/Z-(4-(3,4,5,6-tetrahydropyrimidin-2-yl)aminocarbonylbenzylidene)-2,5-dioxoimidazolidin-1-yl)-(2S)-N-benzyloxycarbonylaminopropionate (E/Z-38.3)

In analogy with the protocol for synthesizing 11.6 (protocol 11f), 0.05 g of (E-38.2) (0.1 mmol) and 0.01 g (0.1 mmol) of 2-amino-3,4,5,6-tetrahydropyrimidine are reacted with the equivalent quantity of TOTU (0.033 g) in dimethylformamide in the presence of diisopropylethylamine. The customary working-up yields 0.06 g of (E-38.3), which can be reacted without further purification. 0.025 g of the crude product of (Z-38.3) is obtained in the same manner from 0.03 g of (Z-38.2).

38d) 3-(4-E/Z-(4-(3,4,5,6-Tetrahydropyrimidin-2-yl) aminocarbonylbenzylidene-2,5-dioxoimidazolidin-1-yl)-(2S)-N-benzyloxycarbonylamino-propionic Acid (E/Z-38.4)

0.055 g of (E-38.3) is stirred for 2 h, while cooling with ice, in 2 ml of 90% trifluoroacetic acid. Removing the solvent in vacuo, and freeze-drying the residue, yields 0.02 g of (E-38.4). 0.012 g of (Z-38.4) is obtained in an analogous manner from 0.02 g of. (Z-38.3).

Inhibition of bone reabsorption by the novel compounds can be determined, for example, using an osteoclast reabsorption test ("PIT ASSAY"), for example in analogy with WO 95/32710. The test methods which are used to determine the antagonistic effect of the novel compounds on the $\alpha_V\beta_3$ vitronectin receptor are described below.

Test Method 1:
Inhibition of the binding of human vitronectin (Vn) to human vitronectin receptor (VnR) $\alpha_V\beta_3$: ELISA-Test.
(In the listing of the test results, test method 1 is abbreviated to Vn/VnR)

1. Purification of human vitronectin
    Human vitronectin is isolated from human plasma and purified by affinity chromatography using the method of Yatohyo et al., Cell Structure and Function, 1988, 23, 281–292.
2. Purification of human vitronectin receptor ($\alpha_V\beta_3$)
    Human vitronectin receptor is isolated from the human placenta using the method of Pytela et al., Methods Enzymol. 1987, 144, 475. Human vitronectin receptor $\alpha_V\beta_3$ can also be isolated from some cell lines (for example from 293 cells, a human embryonic kidney cell line) which are cotransfected with DNA sequences for the two subunits, $\alpha_V$ and $\beta_3$, of the vitronectin receptor. The subunits are extracted with octylglycoside and subsequently chromatographed on concanavalin A, heparin-Sepharose and S-300.

3. Monoclonal antibodies
    Murine monoclonal antibodies which are specific for the $\beta_3$ subunit of the vitronectin receptor are prepared either by the method of Newman et al., Blood, 1985, 227–232, or by a similar method. The rabbit Fab 2 anti-mouse Fc conjugate with horseradish peroxidase (anti-mouse Fc HRP) was obtained from Pel Freeze (Catalog No. 715 305-1).
4. ELISA test
    Nunc Maxisorb 96-well microtiter plates are coated, at 4° C. overnight, with a solution of human vitronectin (0.002 mg/ml, 0.05 ml/well) in PBS (phosphate-buffered sodium chloride solution). The plates are washed twice with PBS/0.05% Tween 20 and blocked by incubating them (for 60 min) with bovine serum albumin (BSA, 0.5%, RIA grade or better) in tris-HCl (50 mM), NaCl (100 mM), $MgCl_2$ (1 mM), $CaCl_2$ (1 mM), $MnCl_2$ (1 mM), pH 7. Solutions of known inhibitors and of the test substances, in concentrations of $2\times10^{-12}$–$2\times10^{-6}$ mol/l, are prepared in assay buffer [BSA (0.5%, RIA grade or better) in tris-HCl (50 mM/l), NaCl (100 mM), $MgCl_2$ (1 mM), $CaCl_2$ (1 mM), $MnCl_2$ (1 mM), pH 7]. The blocked plates are emptied and in each case 0.025 ml of this solution, which contains a defined concentration (from $2\times10^{-12}$ to $2\times10^{-6}$) of either a known inhibitor or a test substance, is added to each well. 0.025 ml of a solution of the vitronectin receptor in the test buffer (0.03 mg/ml) is pipetted into each well of the plate and the plate is then incubated at room temperature on a shaker for 60–180 min. In the meantime, a solution (6 ml/plate) of a murine monoclonal antibody which is specific for the $\beta_3$ subunit of the vitronectin receptor is prepared in the assay buffer (0.0015 mg/ml). A second rabbit antibody, which represents an anti-mouse Fc HRP antibody conjugate, is added to this solution (0.001 ml of stock solution/6 ml of the murine monoclonal anti-$\beta_3$ antibody solution) and this mixture of the murine anti-$\beta_3$ antibody and the rabbit anti-mouse Fc HRP antibody conjugate is allowed to incubate while the receptor/inhibitor incubation is in progress. The test plates are washed 4 times with PBS solution containing 0.05% Tween-20 and 0.05 ml of the antibody mixture is in each case pipetted into each well of the plate, which is then incubated for 60–180 min. The plate is washed 4 times with PBS/0.05% Tween-20 and then developed with 0.05 ml/well of a PBS solution which contains 0.67 mg/ml o-phenylenediamine and 0.012% $H_2O_2$. Alternatively, o-phenylenediamine can be used in a buffer (pH 5) which contains $Na_3PO_4$ (50 mM) and citric acid (0.22 mM). The color development is stopped with 1N $H_2SO_4$ (0.05 ml/well). The absorption of each well is measured at 492–405 nm and the data are evaluated using standard methods.

Test Method 2:
Inhibition of the binding of Kistrin to human vitronectin receptor (VnR) $\alpha_V\beta_3$: ELISA test
(In the listing of the test results, test method 2 is abbreviated to Kistrin/VnR)

1. Purification of Kistrin
    Kistrin is purified using the methods of Dennis et al., as described in Proc. Natl. Acad. Sci. USA 1989, 87, 2471–2475 and PROTEINS: Structure, Function and Genetics 1993, 15, 312–321.
2. Purification of human vitronectin receptor ($\alpha_V\beta_3$) see test method 1.
3. Monoclonal antibodies see test method 1.

4. ELISA test

The ability of substances to inhibit the binding of Kistrin to the vitronectin receptor can be elucidated using an ELISA test. For this purpose, Nunc 96-well microtiter plates are coated with a solution of Kistrin (0.002 mg/ml) in accordance with the method of Dennis et al., as described in PROTEINS: Structure, Function and Genetics 1993, 15, 312–321. The subsequent experimental implementation of the ELISA test is as described in test method1, item 4.

Test Results:

| Example | Vn/VnR IC$_{50}$ ($\mu$M) | Kistrin/VnR IC$_{50}$ ($\mu$M) |
|---|---|---|
| 1 | 0.008 | 0.02 |
| 3 |  | 0.36 |
| 4 |  | 1.66 |
| 5 |  | 0.04 |
| 7 |  | 0.58 |
| 8 |  | 0.13 |
| 18 |  | 0.81 |
| 19 |  | 0.02 |

Priority Federal Republic of Germany applications, 19610919.1, filed Mar. 20, 1996, 19626701.3, filed Jul. 3, 1996, and 19635522.2 filed Sep. 2, 1996, including the specification, any drawings, claims and abstract, are hereby incorporated by reference.

What is claimed is:

1. A compound selected from the group consisting of:

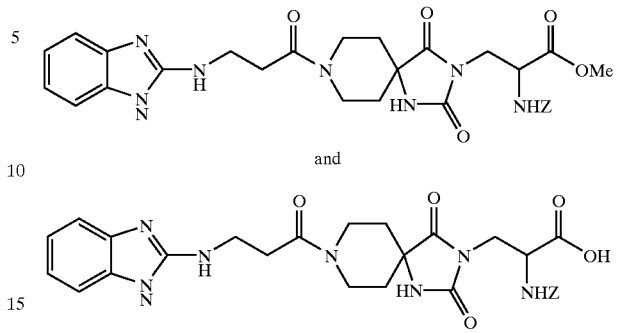

and wherein Z is benzyloxycarbonyl or a physiologically tolerated salt thereof.

2. A pharmaceutical composition comprising:
   (a) a compound as claimed in claim 1 and/or its physiologically tolerated salt thereof; and
   (b) a pharmaceutically acceptable carrier.

3. A method of treating neuropathies or retinopathies comprising administering to a patient in need thereof an effective amount of a compound as claimed in claim 1 and/or a physiologically tolerated salt thereof.

* * * * *